(12) United States Patent
Calderwood et al.

(10) Patent No.: US 6,215,001 B1
(45) Date of Patent: *Apr. 10, 2001

(54) IMIDAZOLE DERIVATIVES AS THERAPEUTIC AGENTS

(75) Inventors: David John Calderwood; Adrian John Fisher; James Edward Jeffery; Colin Gerhart Pryce Jones; Paul Rafferty, all of Nottingham (GB)

(73) Assignee: Knoll Aktiengesellschaft, Ludwigshaften (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/415,516

(22) Filed: Oct. 7, 1999

Related U.S. Application Data

(62) Division of application No. 09/050,396, filed on Mar. 31, 1998, now Pat. No. 6,031,109, which is a division of application No. 08/786,960, filed on Jan. 23, 1997, now Pat. No. 5,780,642, which is a continuation of application No. 08/578,713, filed as application No. PCT/EP94/01924 on Jun. 10, 1994, now abandoned.

(30) Foreign Application Priority Data

Jun. 22, 1993 (GB) .................................................. 9312893

(51) Int. Cl.$^7$ ...................... C07D 233/61; C07D 233/66; C07D 233/54; C07D 233/68; A61K 31/417
(52) U.S. Cl. ........................ 548/339.5; 514/399; 514/400; 548/335.5; 548/336.1; 548/338.1; 548/340.1; 548/342.1
(58) Field of Search ............................ 548/340.1, 336.1, 548/335.5, 338.1, 342.1, 339.5; 514/399, 400

(56) References Cited

U.S. PATENT DOCUMENTS 5,780,642 * 7/1998 Calderwood et al. .
6,031,109 * 2/2000 Calderwood et al. .

\* cited by examiner

Primary Examiner—Floyd D. Higel
(74) Attorney, Agent, or Firm—Keil & Weinkauf

(57) ABSTRACT

Compounds of the formula I

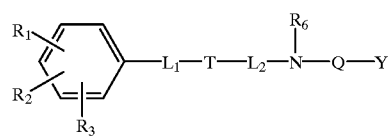

and pharmaceutically acceptable salts thereof in which $R_1$ represents hydrogen, halo, cyano, cyanoalkyl, alkyl, alkoxy, phenoxy, phenyl, alkoxycarbonyl, —$NR_{13}R_{14}$, —$N(R_{15})SO_2R16$, halogenated alkoxy, halogenated alkyl, arylalkoxy, hydroxy, phenylalkyl, alkoxycarbonylvinyl, —$S(O)_nR_7$, alkoxycarbonylalkyl, carboxyalkyl, —$CONR_{13}R_{12}$ carbamoylvinyl, —$OSO_2R_{21}$, 4,5-dihydrothiazol-2-yl, 4,4-dimethyl-2-oxazolin-2-yl or —$NR_{60}R_{61}$; or $R_1$ represents a group of formula —$(O)_z$—$L_3$G wherein z equals 0 or 1, $L_3$ represents a $C_{1-4}$ alkylene chain, G represents a group of formula a), b), c), or d): a) —$NR_{22}R_{23}$; b) —$S(O)_mR_{26}$; c) $CONR_{27}R_{28}$; d) —$OR_{29}$; $R_2$ and $R_3$ independently represent hydrogen, halo, alkyl, alkoxy, —$NR_{13}R_{14}$, halogenated alkoxy, halogenated alkyl, hydroxy, —$S(O)_nR_7$ or —$NR_{60}R_{61}$; $L_1$ represents e) a bond, or f) alkylene, cycloalkylene or cycloalkylidene; T represents a bond or O, S, SO, $SO_2$, a carbonyl group, or 1,3-dioxolan-2-ylidene; $L_2$ represents alkylene, cycloalkylene, or cycloalkylidene; $R_6$ represents hydrogen or alkyl (optionally substituted by alkoxycarbonyl or hydroxy); Q represents a $C_{1-9}$ alkylene chain (optionally substituted by alkyl or hydroxy); and Y represents an optionally substituted imidazole ring; which are antiinflammatory, antiallergic and immunodulant agents. Compositions containing these compounds and processes to make them are also disclosed.

21 Claims, No Drawings

IMIDAZOLE DERIVATIVES AS THERAPEUTIC AGENTS

This application is a divisional of application Ser. No. 09/050,396, filed Mar. 31, 1998, now U.S. Pat. No. 6,031,109, which is a divisional of application Ser. No. 08/786,960, filed Jan. 23, 1997 now U.S. Pat. No. 5,780,642, which is a file wrapper continuation of application Ser. No. 08/578,713, now abandoned, which is a 35 U.S.C. § 371 of PCT/EP 94/01924, filed on Jun. 10, 1994.

This invention relates to novel substituted imidazoles having therapeutic activity useful in treating conditions associated with inflammation, allergy or aberrant immune reactions, to therapeutic compositions containing these novel compounds and to processes for preparing these novel compounds.

It is believed that, in response to an inflammatory stimulus, phospholipase enzymes are activated leading to the release of arachidonic acid from phospholipids. Existing non-steroidal antiinflammatory agents (NSAIA) are believed to act primarily by blocking the conversion of this released arachidonic acid into prostaglandins via the cyclooxygenase pathway of the arachidonic acid cascade. Many existing NSAIA are unsuitable for use by asthmatics. We have found a series of compounds which act to block the release of arachidonic acid from phospholipids. These compounds are indicated as useful antiinflammatory compounds with a potentially broader spectrum of activity than existing NSAIA, and potentially fewer gastro-intestinal side-effects. In addition the compounds may be useful in the treatment of asthma.

Compound A is disclosed in Il Farmaco, 44 (5), 495–502, 1989 as having an inhibitory effect on platelet aggregation in vitro.

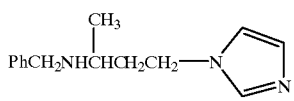

A

Compound B is disclosed as a chemical intermediate in EP 0230035. No pharmacological activity is disclosed for this compound.

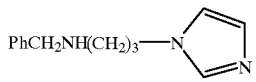

B

GB 2088888 discloses desensitizing compositions for photographic developers comprising imidazoles of formula C

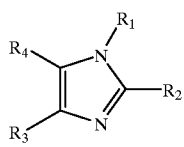

C wherein $R_1$ represents a hydrogen atom, a $C_{1-20}$ alkyl group or a $C_{6-20}$ aryl group; $R_2$ represents a hydrogen atom, a $C_{1-20}$ alkyl group, a $C_{6-20}$ aryl group, an amino group, or a $C_{1-20}$ alkylthio group; and $R_3$ and $R_4$, which may be the same or different, each represents a hydrogen atom, a $C_{1-4}$ alkyl group, or a $C_{6-20}$ aryl group; and $R_1$, $R_2$, $R_3$ and $R_4$ may be substituted. 1-(6-Benzylaminohexyl)-2-methylimidazole is disclosed. No pharmacological activity is disclosed for this compound.

More distantly related compounds of formula D

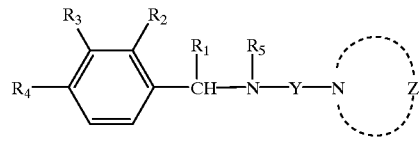

D in which the ring incorporating N and Z represents dialkylamino, morpholino or piperidino are disclosed in the Indian Journal of Pharmacology 1973, 5, 428 and Pfl. Krankh. 1975, 3, 149. These compounds are disclosed as potential central nervous system depressants. N-[2-(4-Morpholino)propyl]-α-ethyl-3,4-dichlorobenzylamine is alleged to have antiinflammatory activity but has a wide range of undesirable side-effects in mice.

Our co-pending application PCT/EP92/02899 (WO 93/13075) discloses compounds of formula E

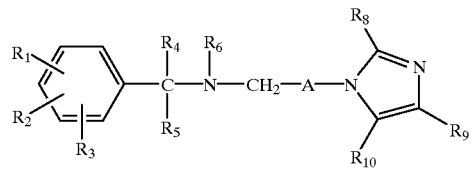

E

All compounds disclosed in that application are disclaimed from this present application in the first proviso.

The co-pending application WO 93/14070 discloses the use of compounds of formula F

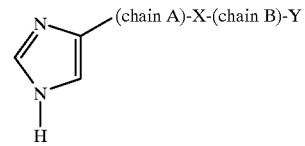

F in which chain A represents inter alia a $C_{1-6}$ hydrocarbon chain which is straight or branched; X represents inter alia —NH—; chain B represents an alkylene chain of formula $(CH_2)_n$ in which n is a number between 0 and 5 or a branched alkylene chain having from 2 to 8 carbon atoms and Y represents inter alia an aryl group such as an optionally substituted phenyl group; as antagonists of histamine $H_3$ receptors. There is no disclosure of antiinflammatory or anti-asthmatic activity for these compounds.

EP 0485890 discloses the use of compounds of formula G

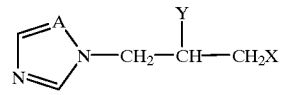

G in which A is CH or N; X is inter alia —NR$_1$R$_2$ in which R$_1$ is alkylphenyl (in which the phenyl ring is optionally substituted) inter alia, R$_2$ is hydrogen or R$_1$; and Y is OH inter alia; for the treatment and prophylaxis of systemic mycoses, protozoal, fungal and bacterial infections. All compounds disclosed in that application are disclaimed from this present application in the third proviso.

EP 081324 discloses the use of compounds of formula H

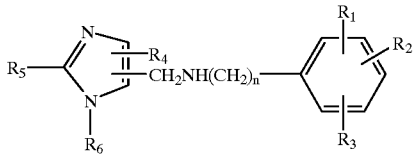

in which $R_1$, $R_2$ and $R_3$ which may be the same or different represent hydrogen, chloro, bromo, fluoro, methyl, ethyl, methoxy, amino, hydroxy or nitro;

$R_4$ is hydrogen or a $C_{1-7}$ alkyl group;

$R_5$ is hydrogen or a $C_{1-5}$ alkyl group or phenyl;

$R_6$ is hydrogen or a $C_{1-7}$ alkyl group or a substituted or unsubstituted benzyl group; and n is 0 or 1;

as diuretic agents which also have antithrombotic and antihypertensive activity. All compounds disclosed in that application are disclaimed from this present application in the second proviso (part a).

Japanese patent application no. 63-141969 (1988) discloses the use of compounds of formula J

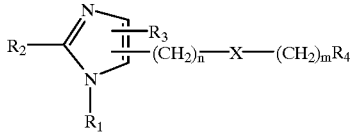

in which $R_1$ represents lower alkyl;

$R_2$ and $R_3$ represent hydrogen, lower alkyl or $SR_5$;

$R_4$ represents substituted phenyl or substituted pyridyl (wherein the substituent is hydrogen, lower alkyl or halogen);

$R_5$ represents hydrogen or lower alkyl;

X is O, S or imino (optionally substituted by lower alkyl) and m and n are 0, 1 or 2; as cerebral function improvers.

All compounds disclosed in that application are disclaimed from this present application in the second proviso (part b).

3'-(Imidazol-1-yl)-3-phenyldipropylamine is disclosed in J.A.C.S. 101, 5376 (1979). No biological activity is reported. This compound is disclaimed in the fifth proviso.

U.S. Pat. No. 4,404,387 and U.S. Pat. No. 4,338,453 disclose the use of compounds of formula K

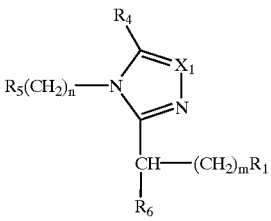

wherein $X_1$ is a) CH; or b) $C(CH_3)$; wherein m is zero, 1, 2 or 3; n is zero, 1 or 2; $R_1$ is a) 1-piperidinyl substituted at the 3 or 4 position by $R_{15}$; b) —$N(CH_3)$—$(CH_2)_p$—$R_{15}$ or c) —NH—$(CH_2)_p$—$R_{15}$ wherein p is 1, 2 or 3; $R_4$ is a) hydrogen or b) $C_{1-3}$ alkyl inter alia; $R_5$ and $R_{15}$ are the same or different and are a) 2, 3 or 4-pyridinyl or b) phenyl substituted by zero to 2 chloro, fluoro, bromo, $C_{1-3}$ alkyl or $C_{1-3}$ alkoxy or c) phenyl substituted by one trifluoromethyl and zero to one of the previous phenyl substituents, wherein $R_6$ is a) hydrogen; b) $C_{1-3}$ alkyl or c) hydroxy inter alia; as antiallergic agents. All compounds disclosed in these applications are disclaimed from the present application in the fourth proviso.

The present invention provides novel compounds of formula I

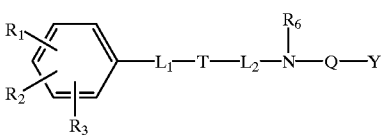

and pharmaceutically acceptable salts thereof in which $R_1$ represents hydrogen, halo, cyano, a cyano $C_{1-6}$ alkyl group, a $C_{1-12}$ alkyl group (optionally substituted by one or more hydroxy groups), a $C_{1-6}$ alkoxy group, phenoxy (optionally substituted), phenyl (optionally substituted), a $C_{2-6}$ alkoxycarbonyl group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$N(R_{15})SO_2R_{16}$ (in which $R_{15}$ represents hydrogen or $C_{1-6}$ alkyl and $R_{16}$ represents hydroxy, a $C_{1-6}$ alkyl group or optionally substituted phenyl), a halogenated $C_{1-4}$ alkoxy group, a halogenated $C_{1-4}$ alkyl group, arylalkoxy (optionally substituted), hydroxy, a phenyl $C_{1-6}$ alkyl group (optionally substituted), a ($C_{2-6}$ alkoxycarbonyl)vinyl group, a group of formula —$S(O)_nR_7$ (in which $R_7$ represents a $C_{1-6}$ alkyl group and n is 0, 1 or 2 or n is 2 and $R_7$ represents a group of formula —$N(R_{17})R_{18}$ (in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a $C_{2-6}$ alkoxycarbonyl $C_{1-6}$ alkyl group, a carboxy $C_{1-6}$ alkyl group, a carbamoyl group of formula —$CONR_{11}R_{12}$ (in which $R_{11}$ and $R_{12}$ are independently hydrogen, a $C_{1-6}$ alkyl group, a $C_{3-8}$ cycloalkyl group or optionally substituted phenyl or $R_{11}$ and $R_{12}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a carbamoylvinyl group of formula —CH=CH—CON($R_{11}$)$R_{12}$ in which $R_{11}$ and $R_{12}$ are as previously defined, a group of formula —OSO$_2$R$_{21}$ in which $R_{21}$ represents a $C_{1-6}$ alkyl group or a phenyl group (optionally substituted), 4,5-dihydrothiazol-2-yl, 4,4-dimethyl-2-oxazolin-2-yl or a group of formula —NR$_{60}$R$_{61}$ [in which $R_{60}$ represents hydrogen or a $C_{1-6}$ alkyl group and $R_{61}$ represents a $C_{1-6}$ alkanoyl group or benzoyl (optionally substituted)];

or $R_1$ represents a group of formula —(O)$_z$—L$_3$G wherein z equals 0 or 1, $L_3$ represents a $C_{1-4}$ alkylene chain optionally substituted by one or more $C_{1-4}$ alkyl groups and G represents a group of formula a), b), c), or d)

a) —NR$_{22}$R$_{23}$ in which $R_{22}$ represents hydrogen or a $C_{1-6}$ alkyl group and $R_{23}$ represents hydrogen, a $C_{1-6}$ alkyl group, a $C_{1-6}$ alkanoyl group, phenylsulphonyl (optionally substituted), benzoyl (optionally substituted), a group of formula —CONR$_{24}$R$_{25}$ (wherein $R_{24}$ represents hydrogen, a $C_{1-6}$ alkyl group or a $C_{3-6}$ cycloalkyl group and $R_{25}$ represents hydrogen, a $C_{1-6}$ alkyl group or phenyl (optionally substituted) or $R_{24}$ and $R_{25}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups);

b) —S(O)$_m$R$_{26}$ in which $R_{26}$ represents a $C_{1-6}$ alkyl group, a phenyl group (optionally substituted) and m is 0, 1 or 2 or m is 2 and $R_{26}$ represents a group of formula —N($R_{17}$)R$_{18}$ (in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups);

c) —CONR$_{27}$R$_{28}$ in which $R_{27}$ represents hydrogen or a $C_{1-6}$ alkyl group and $R_{28}$ represents hydrogen, a $C_{1-6}$ alkyl group, a $C_{3-8}$ cycloalkyl group, a phenyl $C_{1-6}$ alkyl group (in which the phenyl ring is optionally substituted), or phenyl (optionally substituted) or $R_{27}$ and $R_{28}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

d) —OR$_{29}$ in which $R_{29}$ represents a $C_{1-6}$ alkyl group, phenyl (optionally substituted), a phenyl $C_{1-6}$ alkyl group (in which the phenyl ring is optionally substituted), a $C_{1-6}$ alkanoyl group, benzoyl (optionally substituted), a $C_{1-6}$ alkylsulphonyl group, a phenylsulphonyl group (optionally substituted), or $R_{29}$ represents a group of formula —L$_4$COR$_{32}$ in which $L_4$ represents a $C_{1-4}$ alkylene chain (optionally substituted by one or more $C_{1-4}$ alkyl groups), and $R_{32}$ represents hydrogen, a $C_{1-6}$ alkyl group, a $C_{1-6}$ alkoxy group, phenyl (optionally substituted) or phenoxy (optionally substituted);

$R_2$ and $R_3$ independently represent hydrogen, halo, a $C_{1-6}$ alkyl group (optionally substituted by one or more hydroxy groups), a $C_{1-6}$ alkoxy group, an amino group of formula —NR$_{13}$R$_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a halogenated $C_{1-4}$ alkoxy group, a halogenated $C_{1-4}$ alkyl group, hydroxy, a group of formula —S(O)$_n$R$_7$ (in which $R_7$ represents a $C_{1-6}$ alkyl group and n is 0, 1 or 2 or n is 2 and $R_7$ represents a group of formula —N($R_{17}$)R$_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups) or a group of formula —NR$_{60}$R$_{61}$ [in which $R_{60}$ represents hydrogen or a $C_{1-6}$ alkyl group and $R_{61}$ represents a $C_{1-6}$ alkanoyl group, or benzoyl (optionally substituted)];

or $R_1$ and $R_2$ together with the phenyl ring to which they are attached represent a naphthyl group (optionally substituted);

or $R_2$ is attached to a position on the phenyl ring adjacent to the position of attachment of $L_1$ on the phenyl ring and —L$_1$—T—L$_2$— and $R_2$ together with the phenyl ring to which they are attached represent an indane ring which is optionally substituted;

$L_1$ represents e) a bond, or f) a $C_{1-4}$ alkylene chain, a $C_{3-6}$ cycloalkylene group, or a $C_{3-6}$ cycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups;

T represents a bond or O, S, SO, SO$_2$, a carbonyl group, or a group of formula 5)

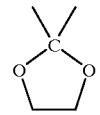

(5)

$L_2$ represents a $C_{1-4}$ alkylene chain, a $C_{3-6}$ cycloalkylene group, or a $C_{3-6}$ cycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups; and when T represents a carbonyl group $L_2$ additionally represents a $C_{1-4}$ oxyalkylene chain, a $C_{3-6}$ oxycycloalkylene group, or a $C_{3-6}$ oxycycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups;

$R_6$ represents hydrogen, a $C_{1-4}$ alkyl group (optionally substituted by one or more hydroxy groups or by a $C_{2-6}$ alkoxycarbonyl group);

Q represents a $C_{1-9}$ alkylene chain [optionally substituted by one or more hydroxy groups and/or by one or more $C_{1-4}$ alkyl groups (optionally substituted by one or more hydroxy groups) and/or optionally interrupted by oxygen or a carbonyl group];

Y represents an imidazole ring of formula (1), (2), (3) or (4)

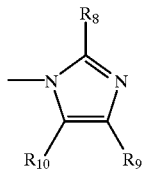

(1)

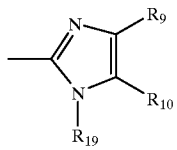

(2)

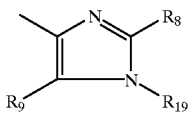

(3)

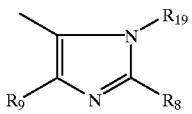

(4)

in which $R_8$ represents hydrogen, a $C_{1-6}$ alkyl group, a halogenated $C_{1-6}$ alkyl group, halo, a $C_{1-4}$ alkoxy group, a halogenated $C_{1-4}$ alkoxy group, a $C_{1-4}$ hydroxyalkyl group, phenyl (optionally substituted), benzoyl (optionally substituted), a benzoyl $C_{1-4}$ alkyl group (optionally substituted), or a phenyl $C_{1-4}$ alkyl group in which the alkyl chain is optionally substituted by one or more hydroxy groups or one or more $C_{1-4}$ alkyl 5 groups and the phenyl ring is optionally substituted;

$R_9$ and $R_{10}$ independently represent hydrogen, a $C_{1-6}$ alkyl group, halo, a halogenated $C_{1-6}$ alkyl group, a $C_{1-4}$ alkoxy group, a halogenated $C_{1-4}$ alkoxy group, phenyl (optionally substituted), a $C_{1-4}$ hydroxyalkyl group, a $C_{2-6}$ alkoxycarbonyl group, nitro, an amino group of formula $NR_{30}R_{31}$ (in which $R_{30}$ and $R_{31}$ are independently hydrogen or a $C_{1-4}$ alkyl group or $R_{30}$ and $R_{31}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a $C_{1-6}$ alkanoyloxy $C_{1-4}$ alkyl group, a cyano $C_{1-6}$ alkyl group, or a group of formula g) or h), g) —$L_5$—$NR_{40}R_{41}$ in which $L_5$ represents a $C_{1-4}$ alkylene chain (optionally substituted by one or more $C_{1-4}$ alkyl groups), $R_{40}$ represents hydrogen or a $C_{1-6}$ alkyl group, and $R_{41}$ represents hydrogen, a $C_{1-6}$ alkyl group, a group of formula $SO_2R_{42}$ [in which $R_{42}$ represents a $C_{1-6}$ alkyl group or phenyl (optionally substituted)], a group of formula $COR_{43}$ [in which $R_{43}$ represents a $C_{1-6}$ alkyl group, phenyl (optionally substituted), pyridyl (optionally substituted), thienyl (optionally substituted), furyl (optionally substituted) or pyrrolyl (optionally substituted), a $C_{1-6}$ alkoxy group, phenoxy (optionally substituted) or arylalkyl (optionally substituted)] or $R_{41}$ represents a group of formula $CONR_{44}R_{45}$ [in which $R_{44}$ represents hydrogen, a $C_{1-6}$ alkyl group or a $C_{3-6}$ cycloalkyl group and $R_{45}$ represents hydrogen, a $C_{1-6}$ alkyl group or phenyl (optionally substituted) or $R_{44}$ and $R_{45}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups]; or h) —$L_7CONR_{90}R_{91}$ in which $L_7$ represents a $C_{1-6}$ alkylene chain optionally substituted by one or more $C_{1-4}$ alkyl groups and $R_{90}$ and $R_{91}$ are independently hydrogen, a $C_{1-6}$ alkyl group or phenyl (optionally substituted) or $R_{90}$ and $R_{91}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups; and $R_{19}$ represents hydrogen, a $C_{1-6}$ alkyl group, an aryl group or an aryl $C_{1-6}$ alkyl group;

with a first proviso that when $R_1$, $R_2$ and $R_3$ independently represent hydrogen, halo, a $C_{1-6}$ alkyl group, a $C_{1-6}$ alkoxy group, phenoxy (optionally substituted by a $C_{1-4}$ alkyl group, a $C_{1-4}$ alkoxy group or halo), phenyl (optionally substituted by a $C_{1-4}$ alkyl group, a $C_{1-4}$ alkoxy group or halo), a $C_{2-6}$ alkoxycarbonyl group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a pyrrolidine ring, a morpholine ring or a piperidine ring), a halogenated $C_{1-4}$ alkoxy group, a halogenated $C_{1-4}$ alkyl group, cyano, benzyloxy (optionally substituted by a $C_{1-4}$ alkyl group, a $C_{1-4}$ alkoxy group or halo), hydroxy, a $C_{1-4}$ hydroxyalkyl group, a ($C_{2-6}$ alkoxycarbonyl)vinyl group; a group of formula —$S(O)_nR_7$ (in which $R_7$ represents a $C_{1-4}$ alkyl group and n is 0, 1 or 2), a $C_{2-4}$ carbamoylalkyl group, a $C_{2-6}$ alkoxycarbonyl $C_{1-2}$ alkyl group, a carbamoyl group of formula —$CONR_{11}R_{12}$ (in which $R_{11}$ and $R_{12}$ are independently hydrogen or a $C_{1-6}$ alkyl group) or $R_1$ and $R_2$ together with the phenyl ring to which they are attached represent a naphthyl group; and $L_1$ represents a bond; and T represents a bond; and $L_2$ represents a group of formula —$CR_4R_5$— in which $R_4$ and $R_5$ independently represent hydrogen, a $C_{1-4}$ alkyl group, phenyl (optionally substituted by a $C_{1-4}$ alkyl group, halo or a $C_{1-4}$ alkoxy group) or $R_4$ and $R_5$ together with the carbon atom to which they are attached represent a $C_{3-6}$ cycloalkyl group; and Q represents a group of formula —CH($R_t$)—A— in which A represents a $C_{1-9}$ alkylene group, which may be straight or branched and $R_t$ represents hydrogen or a $C_{1-4}$ alkyl group; and Y represents a group of formula (1)

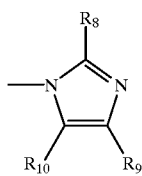

(1)

in which $R_8$ represents hydrogen, a $C_{1-6}$ alkyl group, halo, a $C_{1-4}$ alkoxy group, a $C_{1-4}$ hydroxyalkyl group, phenyl (optionally substituted by a $C_{1-4}$ alkyl group, halo or a $C_{1-4}$ alkoxy group) or benzyl (optionally substituted by a $C_{1-4}$ alkyl group, halo or a $C_{1-4}$ alkoxy group); and $R_9$ and $R_{10}$ independently represent hydrogen, a $C_{1-6}$ alkyl group, halo, a $C_{1-4}$ alkoxy group, phenyl (optionally substituted by a $C_{1-4}$ alkyl group, halo or a $C_{1-4}$ alkoxy group), a $C_{1-4}$ hydroxyalkyl group, a $C_{2-6}$ alkoxycarbonyl group, nitro, an amino group of formula $NR_{30}R_{31}$ (in which $R_{30}$ and $R_{31}$ independently represent hydrogen or a $C_{1-4}$ alkyl group), a $C_{1-6}$ alkanoyloxy $C_{1-4}$ alkyl group, or an aminomethyl group;

then $R_6$ is other than hydrogen, a $C_{1-4}$ alkyl group or an ω-hydroxy $C_{1-4}$ alkyl group;

and a second proviso that when Y is a group of formula (3) or (4) then a) when $R_1$, $R_2$ and $R_3$ independently represent hydrogen, halo, methyl, ethyl, methoxy, amino, hydroxy or nitro; and $L_1$—T—$L_2$ represents methylene; and $R_6$ represents hydrogen; and Q represents methylene; and $R_8$ represents hydrogen, a $C_{1-6}$ alkyl group or phenyl; and $R_9$ represents hydrogen or a $C_{1-6}$ alkyl group then $R_{19}$ is other than hydrogen, a $C_{1-6}$ alkyl group or optionally substituted benzyl; and b) when $R_1$, $R_2$ and $R_3$ independently represent hydrogen, halo or a $C_{1-6}$ alkyl group; and $L_1$—T—$L_2$ represents methylene or ethylene; and $R_6$ represents hydrogen or a $C_{1-6}$ alkyl group; and Q represents methylene or ethylene; and $R_8$ and $R_9$ independently represent hydrogen or a $C_{1-6}$ alkyl group; then $R_{19}$ is other than a $C_{1-6}$ alkyl group;

and a third proviso that when Y represents an imidazole group of formula (1) and $R_8$, $R_9$ and $R_{10}$ are each hydrogen, and $R_1$, $R_2$ and $R_3$ are independently hydrogen, halo, trifluoromethyl, cyano, nitro, $C_{1-10}$ alkyl, a group of formula $R_7S(O)_n$ in which $R_7$ represents a $C_{1-6}$ alkyl group and n is 0, 1 or 2; and —$L_1$—T—$L_2$— represents a $C_{1-4}$ alkylene chain; and $R_6$ represents hydrogen or a $C_{1-4}$ alkyl group; then Q does not represent the group —$CH_2$—CH(OH)—$CH_2$—;

and a fourth proviso that when Y represents a group of formula (2) and $R_1$, $R_2$ and $R_3$ independently represent hydrogen, halo, trifluoromethyl, a $C_{1-3}$ alkyl group or a $C_{1-3}$ alkoxy group; and $R_6$ represents hydrogen or methyl; and Q represents a chain of formula —$(CH_2)_m$—CH($R_k$)— in which m is 0, 1, 2 or 3 and $R_k$ is hydrogen, a $C_{1-3}$ alkyl group or hydroxy; and $R_9$ and $R_{10}$ independently represent hydrogen or phenyl and $R_{19}$ represents aryl or optionally substituted benzyl; then $L_1$—T—$L_2$ is other than methylene, ethylene or trimethylene;

and a fifth proviso that when Y represents a group of formula (1) and —$L_1$—T—$L_2$— and Q both represent trimethylene then one of $R_1$, $R_2$, $R_3$, $R_6$, $R_8$, $R_9$ and $R_{10}$ is other than hydrogen.

It will be understood that a group containing a chain of 3 or more carbon atoms may be straight or branched, for example propyl includes n-propyl and isopropyl and butyl includes n-butyl, sec-butyl, isobutyl and tert-butyl.

The term "optionally substituted" as used herein, unless immediately followed by a list of substituent groups, means optionally substituted by one or more of the following groups: halo; a halogenated $C_{1-6}$ alkyl group, e.g. trifluoromethyl; hydroxy; a $C_{1-6}$ alkyl group (optionally substituted by one or more hydroxy groups); a $C_{1-6}$ alkoxy group; a halogenated $C_{1-6}$ alkoxy group; a $C_{2-6}$ alkoxycarbonyl group; a group of formula $S(O)_zR$ in which R represents a $C_{1-6}$ alkyl group and z is 0, 1 or 2; a $C_{1-6}$ alkanoyl group; carboxy; cyano or a carbamoyl group of formula —$CONR_xR_y$ in which $R_x$ and $R_y$ independently represent a hydrogen or a $C_{1-6}$ alkyl group or $R_x$ and $R_y$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups. The term arylalkoxy means a phenyl $C_{1-6}$ alkoxy group in which the phenyl ring is optionally substituted.

The term "a saturated 3–7 membered heterocyclic ring, optionally containing sulphur, oxygen or an additional nitrogen atom, wherein the ring may be optionally substituted by one or more $C_{1-4}$ alkyl groups" includes morpholine, piperidine, pyrrolidine, thiamorpholine, piperazine, N-methylpiperazine, aziridine, azetidine and azepine.

A first group of preferred compounds of formula I is represented by formula II

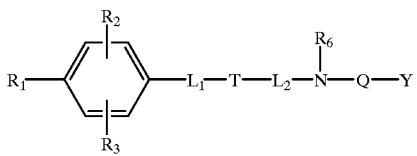

and pharmaceutically acceptable salts thereof in which $R_1$ represents hydrogen, halo, cyano, a cyano $C_{1-6}$ alkyl group, a $C_{1-12}$ alkyl group (optionally substituted by one or more hydroxy groups), a $C_{1-6}$ alkoxy group, phenoxy (optionally substituted), phenyl (optionally substituted), a $C_{2-6}$ alkoxycarbonyl group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$N(R_{15})SO_2R_{16}$ (in which $R_{15}$ represents hydrogen or $C_{1-6}$ alkyl and $R_{16}$ represents hydroxy, a $C_{1-6}$ alkyl group or optionally substituted phenyl), a halogenated $C_{1-4}$ alkoxy group, a halogenated $C_{1-4}$ alkyl group, arylalkoxy (optionally substituted), hydroxy, a phenyl $C_{1-6}$ alkyl group (optionally substituted), a ($C_{2-6}$ alkoxycarbonyl)vinyl group, a group of formula —$S(O)_nR_7$ (in which $R_7$ represents a $C_{1-6}$ alkyl group and n is 0, 1 or 2 or n is 2 and $R_7$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a $C_{2-6}$ alkoxycarbonyl $C_{1-6}$ alkyl group, a carboxy $C_{1-6}$ alkyl group, a carbamoyl group of formula —$CONR_{11}R_{12}$ (in which $R_{11}$ and $R_{12}$ are independently hydrogen, a $C_{1-6}$ alkyl group, a $C_{3-8}$ cycloalkyl group or optionally substituted phenyl or $R_{11}$ and $R_{12}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a carbamoylvinyl group of formula —CH=CH—$CON(R_{11})R_{12}$ in which $R_{11}$ and $R_{12}$ are as previously defined, a group of formula —$OSO_2R_{21}$ in which $R_{21}$ represents a $C_{1-6}$ alkyl group or a phenyl group (optionally substituted), 4,5-dihydrothiazol-2-yl, 4,4-dimethyl-2-oxazolin-2-yl or a group of formula —$NR_{60}R_{61}$ [in which $R_{60}$ represents hydrogen or a $C_{1-6}$ alkyl group and $R_{61}$ represents a $C_{1-6}$ alkanoyl group or benzoyl (optionally substituted)];

or $R_1$ represents a group of formula —$(O)_z$—$L_3G$ wherein z equals 0 or 1, $L_3$ represents a $C_{1-4}$ alkylene chain optionally substituted by one or more $C_{1-4}$ alkyl groups and G represents a group of formula a), b), c) or d)

a) —$NR_{22}R_{23}$ in which $R_{22}$ represents hydrogen or a $C_{1-6}$ alkyl group and $R_{23}$ represents hydrogen, a $C_{1-6}$ alkyl group, a $C_{1-6}$ alkanoyl group, phenylsulphonyl (optionally substituted), benzoyl (optionally substituted), a group of formula —$CONR_{24}R_{25}$ (wherein $R_{24}$ represents hydrogen, a $C_{1-6}$ alkyl group or a $C_{3-6}$ cycloalkyl group and $R_{25}$ represents hydrogen, a $C_{1-6}$ alkyl group or phenyl (optionally substituted) or $R_{24}$ and $R_{25}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups);

b) —$S(O)_mR_{26}$ in which $R_{26}$ represents a $C_{1-6}$ alkyl group, a phenyl group (optionally substituted) and m is 0, 1 or 2 or m is 2 and $R_{26}$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

c) —$CONR_{27}R_{28}$ in which $R_{27}$ represents hydrogen or a $C_{1-6}$ alkyl group and $R_{28}$ represents hydrogen, a $C_{1-6}$ alkyl group, a $C_{3-8}$ cycloalkyl group, a phenyl $C_{1-6}$ alkyl group in which the phenyl ring is optionally substituted, or phenyl (optionally substituted) or $R_{27}$ and $R_{28}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

d) —$OR_{29}$ in which $R_{29}$ represents a $C_{1-6}$ alkyl group, phenyl (optionally substituted), a phenyl $C_{1-6}$ alkyl group (in which the phenyl ring is optionally substituted), a $C_{1-6}$ alkanoyl group, benzoyl (optionally substituted), a $C_{1-6}$ alkylsulphonyl group, a phenylsulphonyl group (optionally substituted), or $R_{29}$ represents a group of formula —$L_4COR_{32}$ in which $L_4$ represents a $C_{1-4}$ alkylene chain (optionally substituted by one or more $C_{1-4}$ alkyl groups), and $R_{32}$ represents hydrogen, a $C_{1-6}$ alkyl group, a $C_{1-6}$ alkoxy group, phenyl (optionally substituted) or phenoxy (optionally substituted);

$R_2$ and $R_3$ independently represent hydrogen, halo, a $C_{1-6}$ alkyl group (optionally substituted by one or more hydroxy groups), a $C_{1-6}$ alkoxy group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a halogenated $C_{1-4}$ alkoxy group, a halogenated $C_{1-4}$ alkyl group, hydroxy, a group of formula —$S(O)_nR_7$ (in which $R_7$ represents a $C_{1-6}$ alkyl group and n is 0, 1 or 2 or n is 2 and $R_7$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups) or a group of formula —$NR_{60}R_{61}$ [in which $R_{60}$ represents hydrogen or a $C_{1-6}$ alkyl group and $R_{61}$ represents a $C_{1-6}$ alkanoyl group, or benzoyl (optionally substituted)];

or $R_1$ and $R_2$ together with the phenyl ring to which they are attached represent a naphthyl group (optionally substituted);

or $R_2$ is attached to a position on the phenyl ring adjacent to the position of attachment of $L_1$ on the phenyl ring and —$L_1$—T—$L_2$— and $R_2$ together with the phenyl ring to which they are attached represent an indane ring which is optionally substituted;

$L_1$ represents e) a bond, or f) a $C_{1-4}$ alkylene chain, a $C_{3-6}$ cycloalkylene group, or a $C_{3-6}$ cycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups;

T represents a bond or O, S, SO, $SO_2$, a carbonyl group, or a group of formula 5)

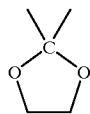

(5)

$L_2$ represents a $C_{1-4}$ alkylene chain, a $C_{3-6}$ cycloalkylene group, or a $C_{3-6}$ cycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups; and when T represents a carbonyl group $L_2$ additionally represents a $C_{1-4}$ oxyalkylene chain, a $C_{3-6}$ oxycycloalkylene group, or a $C_{3-6}$ oxycycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups;

$R_6$ represents hydrogen, a $C_{1-4}$ alkyl group (optionally substituted by one or more hydroxy groups or by a $C_{2-6}$ alkoxycarbonyl group);

Q represents a $C_{1-9}$ alkylene chain [optionally substituted by one or more hydroxy groups and/or by one or more $C_{1-4}$ alkyl groups (optionally substituted by one or more hydroxy groups) and/or optionally interrupted by oxygen or a carbonyl group];

Y represents an imidazole ring of formula (1), (2), (3) or (4)

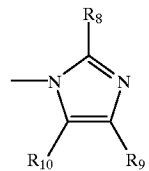

(1)

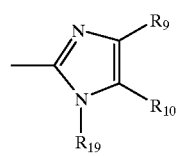

(2)

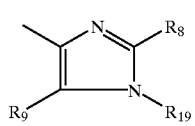

(3)

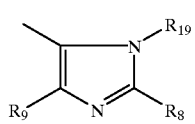

(4)

in which $R_8$ represents hydrogen, a $C_{1-6}$ alkyl group, trifluoromethyl, halo, a $C_{1-4}$ alkoxy group, a $C_{1-4}$ hydroxyalkyl group, phenyl (optionally substituted), benzoyl (optionally substituted), a benzoyl $C_{1-4}$ alkyl group (optionally substituted), or a phenyl $C_{1-4}$ alkyl group in which the alkyl chain is optionally substituted by one or more hydroxy groups or one or more $C_{1-4}$ alkyl groups and the phenyl ring is optionally substituted;

$R_9$ and $R_{10}$ independently represent hydrogen, a $C_{1-6}$ alkyl group, halo, trifluoromethyl, a $C_{1-4}$ alkoxy group, phenyl (optionally substituted), a $C_{1-4}$ hydroxyalkyl group, a $C_{2-6}$ alkoxycarbonyl group, nitro, an amino group of formula $NR_{30}R_{31}$ (in which $R_{30}$ and $R_{31}$ are independently hydrogen or a $C_{1-4}$ alkyl group or $R_{30}$ and $R_{31}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a $C_{1-6}$ alkanoyloxy $C_{1-4}$ alkyl group, a cyano $C_{1-6}$ alkyl group, or a group of formula g) or h), g) —$L_5$—$NR_{40}R_{41}$ in which $L_5$ represents a $C_{1-4}$ alkylene chain (optionally substituted by one or more $C_{1-4}$ alkyl groups), $R_{40}$ represents hydrogen or a $C_{1-6}$ alkyl group, and $R_{41}$ represents hydrogen, a $C_{1-6}$ alkyl group, a group of formula $SO_2R_{42}$ [in which $R_{42}$ represents a $C_{1-6}$ alkyl group or phenyl (optionally substituted)], a group of formula $COR_{43}$ [in which $R_{43}$ represents a $C_{1-6}$ alkyl group, phenyl (optionally substituted), pyridyl (optionally substituted), thienyl (optionally substituted), furyl (optionally substituted) or pyrrolyl (optionally substituted), a $C_{1-6}$ alkoxy group, phenoxy (optionally substituted) or arylalkyl (optionally substituted)] or $R_{41}$ represents a group of formula CONR$_{44}$R$_{45}$ [in which R$_{44}$ represents hydrogen, a C$_{1-6}$ alkyl group or a C$_{3-6}$ cycloalkyl group and R$_{45}$ represents hydrogen, a C$_{1-6}$ alkyl group or phenyl (optionally substituted) or R$_{44}$ and R$_{45}$ together with the nitrogen atom to which they are attached represent a saturated 3–7 membered heterocyclic ring, optionally containing sulphur, oxygen or an additional nitrogen atom, wherein the ring may be optionally substituted by one or more C$_{1-4}$ alkyl groups]; or h) —L$_7$CONR$_{90}$R$_{91}$ in which L$_7$ represents a C$_{1-6}$ alkylene chain and R$_{90}$ and R$_{91}$ are independently hydrogen, a C$_{1-6}$ alkyl group or phenyl (optionally substituted) or R$_{90}$ and R$_{91}$ together with the nitrogen atom to which they are attached represent a saturated 3–7 membered heterocyclic ring, optionally containing sulphur, oxygen or an additional nitrogen atom, wherein the ring may be optionally substituted by one or more C$_{1-4}$ alkyl groups; and R$_{19}$ represents hydrogen, a C$_{1-6}$ alkyl group, an aryl group or an aryl C$_{1-6}$ alkyl group.

In a preferred group of compounds of formula II, R$_1$ represents hydrogen, halo, hydroxy, cyano, a C$_{1-12}$ alkyl group (optionally substituted by one or more hydroxy groups), a C$_{1-6}$ alkoxy group, a C$_{2-6}$ alkoxycarbonyl group, phenyl (optionally substituted), a halogenated C$_{1-4}$ alkyl group, arylalkoxy (optionally substituted), a group of formula —S(O)$_n$R$_7$ (in which R$_7$ represents a C$_{1-6}$ alkyl group and n is 0; or n is 2 and R$_7$ represents a group of formula —N(R$_{17}$)R$_{18}$ (in which R$_{17}$ and R$_{18}$ independently represent hydrogen, a C$_{1-6}$ alkyl group, a C$_{3-6}$ cycloalkyl group or R$_{17}$ and R$_{18}$ together with the nitrogen atom to which they are attached represent a saturated 3–7 membered heterocyclic ring, optionally containing sulphur, oxygen or an additional nitrogen atom, wherein the ring may be optionally substituted by one or more C$_{1-4}$ alkyl groups), a carbamoyl group of formula —CONR$_{11}$R$_{12}$ (in which R$_{11}$ and R$_{12}$ are independently hydrogen, a C$_{1-6}$ alkyl group or a C$_{3-8}$ cycloalkyl group), a carbamoylvinyl group of formula —CH=CH—CON(R$_{11}$)R$_{12}$ in which R$_{11}$ and R$_{12}$ are as previously defined, a group of formula —OSO$_2$R$_{21}$ (in which R$_{21}$ represents a C$_{1-6}$ alkyl group or a phenyl group (optionally substituted)), 4,5-dihydrothiazol-2-yl, 4,4-dimethyl-2-oxazolin-2-yl, or a group of formula —NR$_{60}$R$_{61}$ [in which R$_{60}$ represents hydrogen and R$_{61}$ represents a C$_{1-6}$ alkanoyl group or benzoyl (optionally substituted)];

or R$_1$ represents a group of formula —(O)$_z$—L$_3$G wherein z equals 0 or 1, L$_3$ represents a C$_{1-4}$ alkylene chain optionally substituted by one or more C$_{1-4}$ alkyl groups and G represents a group of formula a), b), c), or d)

a) —NR$_{22}$R$_{23}$ in which R$_{22}$ represents hydrogen and R$_{23}$ represents hydrogen, phenylsulphonyl (optionally substituted), a group of formula —CONR$_{24}$R$_{25}$ (wherein R$_{24}$ represents hydrogen or a C$_{1-6}$ alkyl group and R$_{25}$ represents hydrogen or a C$_{1-6}$ alkyl group), or benzoyl (optionally substituted);

b) —S(O)$_m$R$_{26}$ in which R$_{26}$ represents a C$_{1-6}$ alkyl group or a phenyl group (optionally substituted) and m is 0, 1 or 2 or m is 2 and R$_{26}$ represents a group of formula —N(R$_{17}$)R$_{18}$ in which R$_{17}$ and R$_{18}$ independently represent hydrogen, a C$_{1-6}$ alkyl group or a C$_{3-6}$ cycloalkyl group;

c) —CONR$_{27}$R$_{28}$ in which R$_{27}$ represents hydrogen and R$_{28}$ represents hydrogen, a C$_{1-6}$ alkyl group, a C$_{3-8}$ cycloalkyl group or a phenyl C$_{1-6}$ alkyl group in which the phenyl ring is optionally substituted;

d) —OR$_{29}$ in which R$_{29}$ represents a phenyl C$_{1-6}$ alkyl group (in which the phenyl ring is optionally substituted);

R$_2$ and R$_3$ independently represent hydrogen, halo, a C$_{1-6}$ alkyl group (optionally substituted by one or more hydroxy groups), a C$_{1-6}$ alkoxy group, or a group of formula —NR$_{60}$R$_{61}$ [in which R$_{60}$ represents hydrogen or a C$_{1-6}$ alkyl group and R$_{61}$ represents benzoyl (optionally substituted)];

or R$_2$ is attached to a position on the phenyl ring adjacent to the position of L$_1$ and —L$_1$—T—L$_2$— and R$_2$ together with the phenyl ring to which they are attached represent an indane ring;

L$_1$ represents e) a bond, or f) a C$_{1-4}$ alkylene chain optionally substituted by one or more C$_{1-4}$ alkyl groups;

T represents a bond or O, S, SO, SO$_2$, a carbonyl group or a group of formula 5)

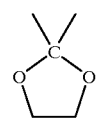

(5)

L$_2$ represents a C$_{1-4}$ alkylene chain which is optionally substituted by one or more C$_{1-4}$ alkyl groups or when T represents a carbonyl group L$_2$ additionally represents a C$_{1-4}$ oxyalkylene chain which is optionally substituted by one or more C$_{1-4}$ alkyl groups;

R$_6$ represents hydrogen, a C$_{1-4}$ alkyl group (optionally substituted by one or more hydroxy groups or by a C$_{2-6}$ alkoxycarbonyl group);

Q represents a C$_{1-9}$ alkylene chain [optionally substituted by one or more hydroxy groups];

Y represents an imidazole ring of formula (1), (2), (3) or (4)

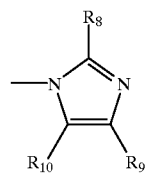

(1)

(2)

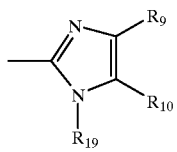

(3)

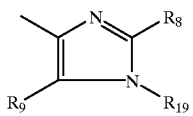

(4)

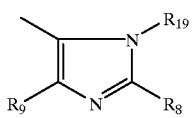

in which $R_8$ represents hydrogen, a $C_{1-6}$ alkyl group or a phenyl $C_{1-4}$ alkyl group in which the alkyl chain is optionally substituted by one or more hydroxy groups;

$R_9$ and $R_{10}$ independently represent hydrogen or a group of formula g), g) 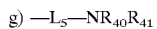 —$L_5$—$NR_{40}R_{41}$ in which $L_5$ represents a $C_{1-4}$ alkylene chain (optionally substituted by one or more $C_{1-4}$ alkyl groups), $R_{40}$ represents hydrogen or a $C_{1-6}$ alkyl group, and $R_{41}$ represents hydrogen, a group of formula $SO_2R_{42}$ [in which $R_{42}$ represents phenyl (optionally substituted)], a group of formula $COR_{43}$ [in which $R_{43}$ represents phenyl (optionally substituted)]; and $R_{19}$ represents hydrogen, a $C_{1-6}$ alkyl group, an aryl group or an aryl $C_{1-6}$ alkyl group.

A second group of preferred compounds of formula I is represented by formula IIa IIa

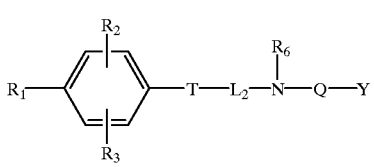

and pharmaceutically acceptable salts thereof in which $R_1$ represents hydrogen, halo, cyano, a cyano $C_{1-6}$ alkyl group, a $C_{1-12}$ alkyl group (optionally substituted by one or more hydroxy groups), a $C_{1-6}$ alkoxy group, phenoxy (optionally substituted), phenyl (optionally substituted), a $C_{2-6}$ alkoxycarbonyl group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$N(R_{15})SO_2R_{16}$ (in which $R_{15}$ represents hydrogen or $C_{1-6}$ alkyl and $R_{16}$ represents hydroxy, a $C_{1-6}$ alkyl group or optionally substituted phenyl), a halogenated $C_{1-4}$ alkoxy group, a halogenated $C_{1-4}$ alkyl group, arylalkoxy (optionally substituted), hydroxy, a phenyl $C_{1-6}$ alkyl group (optionally substituted), a ($C_{2-6}$ alkoxycarbonyl)vinyl group; a group of formula —$S(O)_nR_7$ (in which $R_7$ represents a $C_{1-6}$ alkyl group and n is 0, 1 or 2 or n is 2 and $R_7$ represents a group of formula —$N(R_{17})R_{18}$ in which $R_{17}$ and $R_{18}$ independently represent hydrogen, a $C_{1-6}$ alkyl group or optionally substituted phenyl), a $C_{2-6}$ alkoxycarbonyl $C_{1-6}$ alkyl group, a carboxy $C_{1-6}$ alkyl group, a carbamoyl group of formula —$CONR_{11}R_{12}$ (in which $R_{11}$ and $R_{12}$ are independently hydrogen, a $C_{1-6}$ alkyl group, a $C_{3-6}$ cycloalkyl group or optionally substituted phenyl or $R_{11}$ and $R_{12}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$OSO_2R_{21}$ in which $R_{21}$ represents a $C_{1-6}$ alkyl group or a phenyl group (optionally substituted), 4,5-dihydrothiazol-2-yl, 4,4-dimethyl-2-oxazolin-2-yl or a group of formula —$NR_{60}R_{61}$ [in which $R_{60}$ represents hydrogen or a $C_{1-6}$ alkyl group and $R_{61}$ represents a $C_{1-6}$ alkanoyl group or benzoyl (optionally substituted)];

a group of formula —$(O)_z$—$L_3G$ wherein z is 0, $L_3$ represents a $C_{1-4}$ alkylene chain which optionally substituted by one or more $C_{1-4}$ alkyl groups and G represents a group of formula a), b), c) or d):

a)  —$NR_{22}R_{23}$ wherein $R_{22}$ represents hydrogen or a $C_{1-6}$ alkyl group and $R_{23}$ represents hydrogen, a $C_{1-6}$ alkyl group, a $C_{1-6}$ alkanoyl group, phenylsulphonyl (optionally substituted), benzoyl (optionally substituted), a group of formula —$CONR_{24}R_{25}$ wherein $R_{24}$ represents hydrogen, a $C_{1-6}$ alkyl group or a $C_{3-6}$ cycloalkyl group and $R_{25}$ represents hydrogen, a $C_{1-6}$ alkyl group or phenyl (optionally substituted) or $R_{24}$ and $R_{25}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

b) 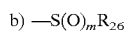 —$S(O)_mR_{26}$ in which $R_{26}$ represents a $C_{1-6}$ alkyl group, a phenyl group (optionally substituted) and m is 0, 1 or 2 or m is 2 and $R_{26}$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

c)  —$CONR_{27}R_{28}$ in which $R_{27}$ represents hydrogen or a $C_{1-6}$ alkyl group and $R_{28}$ represents hydrogen, a $C_{1-6}$ alkyl group, a $C_{3-8}$ cycloalkyl group, a phenyl $C_{1-6}$ alkyl group in which the phenyl ring is optionally substituted, or phenyl (optionally substituted) or $R_{27}$ and $R_{28}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

d) —OR$_{29}$ in which R$_{29}$ represents a C$_{1-6}$ alkyl group, phenyl (optionally substituted), a phenyl C$_{1-6}$ alkyl group (in which the phenyl ring is optionally substituted), a C$_{1-6}$ alkanoyl group, benzoyl (optionally substituted), a C$_{1-6}$ alkylsulphonyl group, a phenylsulphonyl group (optionally substituted), or R$_{29}$ represents a group of formula —L$_4$COR$_{32}$ in which L$_4$ represents a C$_{1-4}$ alkylene chain (optionally substituted by one or more C$_{1-4}$ alkyl groups), and R$_{32}$ represents hydrogen, a C$_{1-6}$ alkyl group, a C$_{1-6}$ alkoxy group, phenyl (optionally substituted) or phenoxy (optionally substituted);

or R$_1$ and R$_2$ together with the phenyl ring to which they are attached represent a naphthyl group (optionally substituted);

R$_2$ and R$_3$ independently represent hydrogen, a C$_{1-4}$ alkyl group, a C$_{1-4}$ alkoxy group, halo, a perhalo C$_{1-2}$ alkyl group, hydroxy, cyano, a C$_{2-6}$ alkoxycarbonyl group, a group of formula —S(O)$_n$R$_7$ (in which R$_7$ represents a C$_{1-6}$ alkyl group or an aryl group and n is 0, 1 or 2), a group of formula —N(R$_{15}$)SO$_2$R$_{16}$ (in which R$_{15}$ represents hydrogen or a C$_{1-6}$ alkyl group and R$_{16}$ represents hydrogen, a C$_{1-6}$ alkyl group or optionally substituted phenyl), or a group of formula —CONR$_{11}$R$_{12}$ (in which R$_{11}$ and R$_{12}$ are independently hydrogen, a C$_{1-6}$ alkyl group, a C$_{3-6}$ cycloalkyl group or optionally substituted phenyl or R$_{11}$ and R$_{12}$ together with the nitrogen to which they are attached represent a saturated 3–7 membered heterocyclic ring, optionally containing sulphur, oxygen or an additional nitrogen atom, wherein the ring may be optionally substituted by one or more C$_{1-4}$ alkyl groups);

T represents O, S, SO, SO$_2$, a carbonyl group or a group of formula (5)

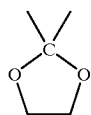

(5)

L$_2$ represents a C$_{1-4}$ alkylene chain, a C$_{3-6}$ cycloalkylene group, or a C$_{3-6}$ cycloalkylidene group, each of which is optionally substituted by one or more phenyl groups (optionally substituted), by one or more C$_{1-4}$ alkyl groups (wherein the alkyl groups are optionally substituted by one or more hydroxy groups or a C$_{2-6}$ alkoxycarbonyl group) or by one or more C$_{3-6}$ cycloalkyl groups, or when T represents a carbonyl group L$_2$ additionally represents a C$_{1-4}$ oxyalkylene chain;

R$_6$ represents hydrogen, a C$_{1-4}$ alkyl group (optionally substituted by one or more hydroxy groups or by a C$_{2-6}$ alkoxycarbonyl group);

Q represents a C$_{1-9}$ alkylene chain [optionally substituted by one or more hydroxy groups and/or by one or more C$_{1-4}$ alkyl groups (optionally substituted by one or more hydroxy groups) and/or optionally interrupted by oxygen or a carbonyl group];

Y represents an imidazole ring of formula (1), (2), (3) or (4)

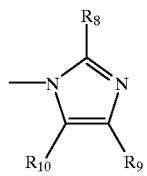
(1)

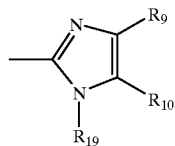
(2)

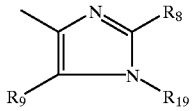
(3)

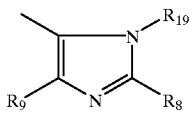
(4)

in which

R$_8$ represents hydrogen, a C$_{1-6}$ alkyl group, halo, trifluoromethyl, a C$_{1-4}$ alkoxy group, a C$_{1-4}$ hydroxyalkyl group, phenyl (optionally substituted), benzoyl (optionally substituted), a benzoyl C$_{1-4}$ alkyl group (optionally substituted), or a phenyl C$_{1-4}$ alkyl group in which the alkyl chain is optionally substituted by one or more hydroxy groups and the phenyl ring is optionally substituted;

R$_9$ and R$_{10}$ independently represent hydrogen, a C$_{1-6}$ alkyl group, halo, trifluoromethyl, a C$_{1-4}$ alkoxy group, phenyl (optionally substituted), a C$_{1-4}$ hydroxyalkyl group, a C$_{2-6}$ alkoxycarbonyl group, nitro, an amino group of formula NR$_{30}$R$_{31}$ (in which R$_{30}$ and R$_{31}$ are independently hydrogen or a C$_{1-4}$ alkyl group or R$_{30}$ and R$_{31}$ together with the nitrogen atom to which they are attached represent a saturated 3–7 membered heterocyclic ring, optionally containing sulphur, oxygen or an additional nitrogen atom, wherein the ring may be optionally substituted by one or more C$_{1-4}$ alkyl groups), a C$_{1-6}$ alkanoyloxy C$_{1-4}$ alkyl group, a group of formula —L$_5$—NR$_{40}$R$_{41}$ wherein L$_5$ represents a C$_{1-4}$ alkylene chain (optionally substituted by one or more C$_{1-4}$ alkyl groups), R$_{40}$ represents hydrogen or a C$_{1-6}$ alkyl group, and R$_{41}$ represents hydrogen, a C$_{1-6}$ alkyl group, a group of formula SO$_2$R$_{42}$ [in which R$_{42}$ represents a C$_{1-6}$ alkyl group or phenyl (optionally substituted)] or a group of formula COR$_{43}$ [in which R$_{43}$ represents a C$_{1-6}$ alkyl group, phenyl (optionally substituted), pyridyl (optionally substituted), thienyl (optionally substituted), furyl (optionally substituted) or pyrrolyl (optionally substituted), a C$_{1-6}$ alkoxy group, phenoxy (optionally substituted) or arylalkyl (optionally substituted)] or R$_{41}$ represents a group of formula CONR$_{44}$R$_{45}$ [in which R$_{44}$ represents hydrogen, a C$_{1-6}$ alkyl group or a C$_{3-6}$ cycloalkyl group and R$_{45}$ represents hydrogen, a C$_{1-6}$ alkyl group or phenyl (optionally substituted)]; and R$_{19}$ represents hydrogen, a C$_{1-6}$ alkyl group, aryl or an aryl C$_{1-6}$ alkyl group.

A preferred group of compounds of formula IIa is now given.

Preferably $R_1$ represents hydrogen, halo, a $C_{1-6}$ alkyl group (which may be substituted by one or more hydroxy groups), benzyloxy (optionally substituted), a $C_{1-4}$ alkoxy group, a $C_{1-4}$ alkylthio group, a $C_{1-4}$ perhaloalkyl group, cyano, a $C_{2-6}$ alkoxycarbonyl group, 4,5-dihydrothiazol-2-yl, or a group of formula —$OSO_2R_{21}$ in which $R_{21}$ represents a $C_{1-6}$ alkyl group or a phenyl group (optionally substituted).

More preferably $R_1$ represents hydrogen, chloro, fluoro, methyl, ethyl, t-butyl, benzyloxy, methoxy, methylthio, trifluoromethyl, cyano, methoxycarbonyl, 4,5-dihydrothiazol-2-yl or n-butylsulphonyloxy. Most preferably $R_1$ represents chloro.

Preferably $R_2$ represents hydrogen or methyl and $R_3$ represents hydrogen, a $C_{1-4}$ alkyl group, a $C_{1-4}$ alkoxy group or halo. More preferably $R_2$ represents hydrogen or methyl and $R_3$ represents hydrogen, chloro or methyl. Most preferably $R_2$ and $R_3$ represent hydrogen.

Preferably T represents O or S. More preferably T represents O.

Preferably $L_2$ represents a $C_{1-4}$ alkylene chain optionally substituted by one or more $C_{1-4}$ alkyl groups. More preferably $L_2$ represents ethylene (—$CH_2$—$CH_2$—), 1,1-dimethylethylene (—$C(CH_3)_2$—$CH_2$—), 2,2-dimethylethylene (—$CH_2$—$C(CH_3)_2$—), 1-methylethylene (—$CH(CH_3)$—$CH_2$—) or trimethylene (—$(CH_2)_3$—). Most preferably $L_2$ represents ethylene, 1,1-dimethylethylene or as 2,2-dimethylethylene.

Preferably $R_6$ represents hydrogen or a $C_{1-4}$ alkyl group (optionally substituted by one or more hydroxy groups or a $C_{2-6}$ alkoxycarbonyl group). More preferably $R_6$ represents hydrogen, methyl, methoxycarbonylmethyl or 2-hydroxyethyl. Most preferably $R_6$ represents hydrogen or methyl.

Preferably Q represents a $C_{2-6}$ alkylene chain optionally substituted by one or more hydroxy groups. More preferably Q represents trimethylene, tetramethylene, pentamethylene or 2-hydroxytrimethylene (—$CH_2$—$CH(OH)$—$CH_2$—). Most preferably Q represents trimethylene or pentamethylene.

Preferably Y represents an imidazole group of formula (1) or (2)

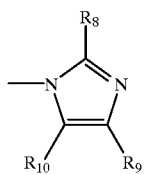

(1)

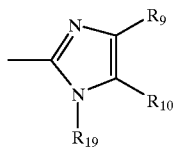

(2)

in which $R_8$ represents hydrogen or a $C_{1-4}$ alkyl group; and $R_9$ and $R_{10}$ each represent hydrogen or a group of formula —$L_5$—$NR_{40}R_{41}$ wherein $L_5$ represents a $C_{1-4}$ alkylene chain (optionally substituted by one or more alkyl groups);

$R_{40}$ represents hydrogen or a $C_{1-4}$ alkyl group and $R_{41}$ represents a group of formula $SO_2R_{42}$ [in which $R_{42}$ represents a $C_{1-6}$ alkyl group or phenyl (optionally substituted)] or a group of formula $COR_{43}$ [in which $R_{43}$ represents a $C_{1-6}$ alkyl group or phenyl (optionally substituted)]; and $R_{19}$ represents hydrogen.

More preferably Y represents a group of formula (1), $R_8$ represents hydrogen or methyl and $R_9$ and $R_{10}$ independently represent hydrogen or a group of formula —$L_5$—$NR_{40}R_{41}$ in which $L_5$ represents methylene, ethylene or trimethylene, $R_{40}$ represents hydrogen and $R_{41}$ represents phenylsulphonyl or benzoyl. More preferably $R_8$ represents hydrogen and $R_9$ and $R_{10}$ independently represent hydrogen, 2-(benzamido)ethyl or 2-(phenylsulphonylamino)ethyl. Most preferably $R_8$, $R_9$ and $R_{10}$ each represent hydrogen.

A third group of preferred compounds of formula I is represented by formula IIb

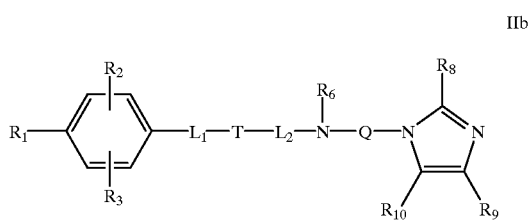

IIb and pharmaceutically acceptable salts thereof in which $R_1$ represents hydrogen, halo, cyano, a cyano $C_{1-6}$ alkyl group, a $C_{1-12}$ alkyl group (optionally substituted by one or more hydroxy groups), a $C_{1-6}$ alkoxy group, phenoxy (optionally substituted), phenyl (optionally substituted), a $C_{2-6}$ alkoxycarbonyl group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$N(R_{15})SO_2R_{16}$ (in which $R_{15}$ represents hydroxy or $C_{1-6}$ alkyl and $R_{16}$ represents hydrogen, a $C_{1-6}$ alkyl group or optionally substituted phenyl), a halogenated $C_{1-4}$ alkoxy group, a halogenated $C_{1-4}$ alkyl group, arylalkoxy (optionally substituted), hydroxy, a phenyl $C_{1-6}$ alkyl group (optionally substituted), a ($C_{2-6}$ alkoxycarbonyl)vinyl group; a group of formula —$S(O)_nR_7$ (in which $R_7$ represents a $C_{1-6}$ alkyl group and n is 0, 1 or 2 or n is 2 and $R_7$ represents a group of formula —$N(R_{17})R_{18}$ in which $R_{17}$ and $R_{18}$ independently represent hydrogen, a $C_{1-6}$ alkyl group or optionally substituted phenyl), a $C_{2-6}$ carbamoylalkyl group, a $C_{2-6}$ alkoxycarbonyl $C_{1-6}$ alkyl group, a carboxy $C_{1-6}$ alkyl group, a carbamoyl group of formula —$CONR_{11}R_{12}$ (in which $R_{11}$ and $R_{12}$ are independently hydrogen, a $C_{1-6}$ alkyl group, a $C_{3-6}$ cycloalkyl group or optionally substituted phenyl or $R_{11}$ and $R_{12}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$OSO_2R_{21}$ in which $R_{21}$ represents a $C_{1-6}$ alkyl group or a phenyl group (optionally substituted), 4,5-dihydrothiazol-2-yl, 4,4- dimethyl-2-oxazolin-2-yl or a group of formula —NR$_{60}$R$_{61}$ [in which R$_{60}$ represents hydrogen or a C$_{1-6}$ alkyl group and R$_{61}$ represents a C$_{1-6}$ alkanoyl group or benzoyl (optionally substituted)];

a group of formula —(O)$_z$—L$_3$G wherein z is 0, L$_3$ represents a C$_{1-4}$ alkylene chain optionally substituted by one or more C$_{1-4}$ alkyl groups and G represents a group of formula a), b), c) or d):

a) —NR$_{22}$R$_{23}$ wherein R$_{22}$ represents hydrogen or a C$_{1-6}$ alkyl group and R$_{23}$ represents hydrogen, a C$_{1-6}$ alkyl group, phenylsulphonyl (optionally substituted), benzoyl (optionally substituted), a group of formula —CONR$_{24}$R$_{25}$ wherein R$_{24}$ represents hydrogen, a C$_{1-6}$ alkyl group or a C$_{3-6}$ cycloalkyl group and R$_{25}$ represents hydrogen, a C$_{1-6}$ alkyl group or phenyl (optionally substituted) or R$_{24}$ and R$_{25}$ together with the nitrogen atom to which they are attached represent a saturated 3–7 membered heterocyclic ring, optionally containing sulphur, oxygen or an additional nitrogen atom, wherein the ring may be optionally substituted by one or more C$_{1-4}$ alkyl groups);

b) —S(O)$_m$R$_{26}$ in which R$_{26}$ represents a C$_{1-6}$ alkyl group, a phenyl group (optionally substituted) and m is 0, 1 or 2 or m is 2 and R$_{26}$ represents a group of formula —N(R$_{17}$)R$_{18}$ in which R$_{17}$ and R$_{18}$ independently represent hydrogen, a C$_{1-6}$ alkyl group, a C$_{3-6}$ cycloalkyl group or optionally substituted phenyl or R$_{17}$ and R$_{18}$ together with the nitrogen atom to which they are attached represent a saturated 3–7 membered heterocyclic ring, optionally containing sulphur, oxygen or an additional nitrogen atom, wherein the ring may be optionally substituted by one or more C$_{1-4}$ alkyl groups;

c) —CONR$_{27}$R$_{28}$ in which R$_{27}$ represents hydrogen or a C$_{1-6}$ alkyl group and R$_{28}$ represents hydrogen, a C$_{1-6}$ alkyl group, a C$_{3-8}$ cycloalkyl group, a phenyl C$_{1-6}$ alkyl group in which the phenyl ring is optionally substituted, or phenyl (optionally substituted) or R$_{27}$ and R$_{28}$ together with the nitrogen atom to which they are attached represent a saturated 3–7 membered heterocyclic ring, optionally containing sulphur, oxygen or an additional nitrogen atom, wherein the ring may be optionally substituted by one or more C$_{1-4}$ alkyl groups;

d) —OR$_{29}$ in which R$_{29}$ represents a C$_{1-6}$ alkyl group, phenyl (optionally substituted), a phenyl C$_{1-6}$ alkyl group (in which the phenyl ring is optionally substituted), a C$_{1-6}$ alkanoyl group, benzoyl (optionally substituted), a C$_{1-6}$ alkylsulphonyl group, a phenylsulphonyl group (optionally substituted), or R$_{29}$ represents a group of formula —L$_4$COR$_{32}$ in which L$_4$ represents a C$_{1-4}$ alkylene chain (optionally substituted by one or more C$_{1-4}$ alkyl groups), and R$_{32}$ represents hydrogen, a C$_{1-6}$ alkyl group, a C$_{1-6}$ alkoxy group, phenyl (optionally substituted) or phenoxy (optionally substituted);

or R$_2$ is attached to a position on the phenyl ring adjacent to the position of attachment of L$_1$ on the phenyl ring and —L$_1$—T—L$_2$— and R$_2$ together with the phenyl ring to which they are attached represent an indane ring which is optionally substituted; or R$_1$ and R$_2$ together with the phenyl ring to which they are attached represent a naphthyl group (optionally substituted);

R$_2$ and R$_3$ independently represent hydrogen, a C$_{1-6}$ alkyl group, a C$_{1-4}$ alkoxy group, halo, a perhalo C$_{1-2}$ alkyl group, hydroxy, cyano, a C$_{2-6}$ alkoxycarbonyl group, a group of formula —S(O)$_n$R$_7$ (in which R$_7$ represents a C$_{1-6}$ alkyl group or an aryl group and n is 0, 1 or 2), a group of formula —N(R$_{15}$)SO$_2$R$_{16}$ (in which R$_{15}$ represents hydrogen or a C$_{1-6}$ alkyl group and R$_{16}$ represents hydrogen, a C$_{1-6}$ alkyl group or optionally substituted phenyl), a group of formula —CONR$_{11}$R$_{12}$ (in which R$_{11}$ and R$_{12}$ are independently hydrogen, a C$_{1-6}$ alkyl group, a C$_{3-6}$ cycloalkyl group or optionally substituted phenyl or R$_{11}$ and R$_{12}$ together with the nitrogen to which they are attached represent a saturated 3–7 membered heterocyclic ring, optionally containing sulphur, oxygen or an additional nitrogen atom, wherein the ring may be optionally substituted by one or more C$_{1-4}$ alkyl groups) or a group of formula —NR$_{60}$R$_{61}$ [in which R$_{60}$ represents hydrogen or a C$_{1-6}$ alkyl group and R$_{61}$ represents a C$_{1-6}$ alkanoyl group, or benzoyl (optionally substituted)];

L$_1$ represents a bond, a C$_{1-4}$ alkylene chain, a C$_{3-6}$ cycloalkylene group, or a C$_{3-6}$ cycloalkylidene group, each of which is optionally substituted by one or more phenyl groups (optionally substituted), by one or more C$_{1-4}$ alkyl groups (wherein the alkyl groups are optionally substituted by one or more hydroxy groups or a C$_{2-6}$ alkoxycarbonyl group) or by one or more C$_{3-6}$ cycloalkyl groups;

T represents a bond;

L$_2$ represents a C$_{1-4}$ alkylene chain, a C$_{3-6}$ cycloalkylene group, or a C$_{3-6}$ cycloalkylidene group, each of which is optionally substituted by one or more phenyl groups (optionally substituted), by one or more C$_{1-4}$ alkyl groups (wherein the alkyl groups are optionally substituted by one or more hydroxy groups or a C$_{2-6}$ alkoxycarbonyl group) or by one or more C$_{3-6}$ cycloalkyl groups;

R$_6$ represents hydrogen, a C$_{1-4}$ alkyl group (optionally substituted by one or more hydroxy groups or by a C$_{2-6}$ alkoxycarbonyl group);

Q represents a C$_{1-9}$ alkylene chain, [optionally substituted by one or more hydroxy groups and/or by one or more C$_{1-4}$ alkyl groups (optionally substituted by one or more hydroxy groups) and/or optionally interrupted by oxygen or a carbonyl group];

R$_8$ represents hydrogen, a C$_{1-6}$ alkyl group, halo, trifluoromethyl, a C$_{1-4}$ alkoxy group, a C$_{1-4}$ hydroxyalkyl group, phenyl (optionally substituted), benzoyl (optionally substituted), a benzoyl C$_{1-4}$ alkyl group (optionally substituted), or a phenyl C$_{1-4}$ alkyl group in which the alkyl chain is optionally substituted by one or more hydroxy groups or one or more phenyl groups and the phenyl ring is optionally substituted;

R$_9$ and R$_{10}$ independently represent hydrogen, a C$_{1-6}$ alkyl group, halo, trifluoromethyl, a C$_{1-4}$ alkoxy group, phenyl (optionally substituted), a C$_{1-4}$ hydroxyalkyl group, a C$_{2-6}$ alkoxycarbonyl group, nitro, an amino group of formula NR$_{30}$R$_{31}$ (in which R$_{30}$ and R$_{31}$ are independently hydrogen or a C$_{1-4}$ alkyl group or R$_{30}$ and R$_{31}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a $C_{1-6}$ alkanoyloxy $C_{1-4}$ alkyl group, a cyano $C_{1-6}$ alkyl group, or a group of formula g) or h)

g) —$L_5$—$NR_{40}R_{41}$ wherein $L_5$ represents a $C_{1-4}$ alkylene chain (optionally substituted by one or more $C_{1-4}$ alkyl groups), $R_{40}$ represents hydrogen or a $C_{1-6}$ alkyl group, and $R_{41}$ represents hydrogen, a $C_{1-6}$ alkyl group, a group of formula $SO_2R_{42}$ [in which $R_{42}$ represents a $C_{1-6}$ alkyl group or phenyl (optionally substituted)], a group of formula $COR_{43}$ [in which $R_{43}$ represents a $C_{1-6}$ alkyl group, phenyl (optionally substituted), pyridyl (optionally substituted), thienyl (optionally substituted), furyl (optionally substituted) or pyrrolyl (optionally substituted), a $C_{1-6}$ alkoxy group, phenoxy (optionally substituted), arylalkoxy (optionally substituted) or arylalkyl (optionally substituted)] or $R_{41}$ represents a group of formula $CONR_{44}R_{45}$ (in which $R_{44}$ represents hydrogen, a $C_{1-6}$ alkyl group or a $C_{3-6}$ cycloalkyl group and $R_{45}$ represents hydrogen, a $C_{1-6}$ alkyl group or phenyl (optionally substituted)] or h) —$L_7CONR_{90}R_{91}$ in which $L_7$ represents a $C_{1-6}$ alkylene chain and $R_{90}$ and $R_{91}$ are independently hydrogen, a $C_{1-6}$ alkyl group or phenyl (optionally substituted) or $R_{90}$ and $R_{91}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups.

A preferred group of compounds of formula IIb is now given.

Preferably $R_1$ represents hydrogen, halo, hydroxy, methyl, propoxycarbonyl, benzyloxy, n-butylsulphonyloxy, phenylsulphonyloxy, 2-(phenylsulphonylamino)ethyl, 2-(benzamido)ethyl, 2-(N'-butylureido)ethyl, (3,4-dimethylphenyl)sulphonylmethyl, n-hexylsulphonylmethyl, 2-hydroxyethyl, 4-hydroxyphenyl, dipropylaminosulphonyl, 2- (benzyloxy) ethyl, N-(n-hexyl) carbamoylmethyl, N-cyclohexylcarbamoyl, N-(4-chlorobenzyl)carbamoylmethyl, N-methylcarbamoylmethyl, N-cycloheptylcarbamoylmethyl, 2-(4-cyanophenylsulphonylamino)ethyl, 2-(4-methoxyphenylsulphonylamino)ethyl, 1,1-diethyl-2-hydroxyethyl, N-n-hexylcarbamoylmethoxy, n-pentylaminosulphonylmethyl, 2-(N-(n-pentyl)carbamoyl) ethyl, 2-(3,4-dihydroxyphenylsulphonylamino)ethyl, 2- (4-[N-methylcarbamoyl)phenylsulphonylamino) ethyl, 4,4-dimethyl-2-oxazolin-2-yl and 2- (N-(n-pentyl)carbamoyl) vinyl. More preferably $R_1$ represents hydrogen, halo, 2-(phenylsulphonylamino)ethyl or N-(n-hexyl) carbamoylmethyl. Most preferably $R_1$ represents chloro, 2-(phenylsulphonylamino) ethyl or N-(n-hexyl) carbamoylmethyl.

Preferably $R_2$ and $R_3$ independently represent hydrogen, chloro, methyl, propyl, pentyl, hydroxy, methoxy, 1-hydroxypentyl or benzamido. More preferably $R_2$ and $R_3$ independently represent hydrogen or methyl. Most preferably $R_2$ and $R_3$ represent hydrogen.

Preferably T and $L_1$ represent a bond.

Preferably $L_2$ represents a group of formula —$C(R_4)$ $(R_5)$— in which $R_4$ and $R_5$ independently represent hydrogen or a $C_{1-4}$ alkyl group. More preferably $R_4$ and $R_5$ both represent hydrogen, methyl or ethyl. Most preferably $R_4$ and $R_5$ both represent methyl or ethyl.

Preferably $R_6$ represents hydrogen or a $C_{1-4}$ alkyl group. More preferably $R_6$ represents hydrogen.

Preferably Q represents a $C_{2-6}$ alkylene chain optionally substituted by a hydroxy group. More preferably Q represents a trimethylene, tetramethylene, pentamethylene or 2-hydroxytrimethylene. Most preferably Q represents trimethylene.

Preferably $R_8$ represents hydrogen, a $C_{1-4}$ alkyl group or α-hydroxybenzyl and $R_9$ and $R_{10}$ independently represent hydrogen, a $C_{1-4}$ alkyl group, a group of formula —$L_5$—$NR_{40}R_{41}$ in which $L_5$ represents methylene, ethylene or trimethylene, $R_{40}$ represents hydrogen and $R_{41}$ represents hydrogen, a $C_{1-6}$ alkyl group, phenylsulphonyl (optionally substituted), benzoyl (optionally substituted) or a $C_{1-6}$ alkanoyl group. More preferably $R_8$ represents hydrogen or methyl and one of $R_9$ and $R_{10}$ represents hydrogen and the other represents 2-(benzamido)ethyl, 2-(phenylsulphonylamino)ethyl, 2-aminoethyl, n-butylaminomethyl, 2-(4-cyanobenzamido)ethyl and 2-(4-methoxybenzamido)ethyl. Most preferably $R_8$ represents hydrogen and $R_9$ represents 2-benzamidoethyl and $R_{10}$ represents hydrogen.

In a more preferred group of compounds of formula IIb, $R_2$ and $R_3$ represent hydrogen;

—$L_1$—T—$L_2$— represents —$C(R_4)(R_5)$— in which $R_4$ and $R_5$ independently represent hydrogen or a $C_{1-4}$ alkyl group;

$R_6$ represents hydrogen or a $C_{1-4}$ alkyl group;

Q represents trimethylene or 2-hydroxytrimethylene;

Y represents a group of formula (1);

$R_8$ and $R_{10}$ represent hydrogen;

and either a) $R_1$ represents a group of formula —$(O)_z$— $L_3G$ in which z is 0 and $L_3$ represents a $C_{1-4}$ alkylene chain (optionally substituted by one or more $C_{1-4}$ alkyl groups) and G represents a group of formula —$NR_{22}R_{23}$ [in which $R_{22}$ represents hydrogen or a $C_{1-4}$ alkyl group and $R_{23}$ represents a $C_{1-6}$ alkanoyl group, phenylsulphonyl (optionally substituted) or benzoyl (optionally substituted)] or a group of formula $CONR_{27}R_{28}$ in which $R_{27}$ represents hydrogen and $R_{28}$ represents a $C_{1-6}$ alkyl group; and $R_9$ represents hydrogen or b) $R_9$ represents a group of formula —$L_5$—$N(R_{40})R_{41}$ in which $L_5$ represents a $C_{1-4}$ alkylene chain (optionally substituted by one or more $C_{1-4}$ alkyl groups), $R_{40}$ represents hydrogen or a $C_{1-4}$ alkyl group and $R_{41}$ represents hydrogen, a group of formula $SO_2R_{42}$ [in which $R_{42}$ represents a $C_{1-6}$ alkyl group or phenyl (optionally substituted)] or a group of formula $COR_{43}$ [in which $R_{43}$ represents a $C_{1-6}$ alkyl group or phenyl (optionally substituted)]; and $R_1$ represents hydrogen or chloro.

A fourth group of preferred compounds of formula I is represented by formula IIc

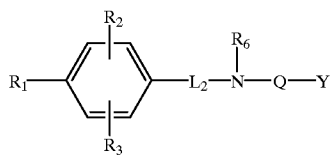

IIc and pharmaceutically acceptable salts thereof in which
$R_1$ represents hydrogen, halo, cyano, a cyano $C_{1-6}$ alkyl group, a $C_{1-12}$ alkyl group (optionally substituted by one or more hydroxy groups), a $C_{1-6}$ alkoxy group, phenoxy (optionally substituted), phenyl (optionally substituted), a $C_{2-6}$ alkoxycarbonyl group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$N(R_{15})SO_2R_{16}$ (in which $R_{15}$ represents hydrogen or $C_{1-6}$ alkyl and $R_{16}$ represents hydroxy, a $C_{1-6}$ alkyl group or optionally substituted phenyl), a halogenated $C_{1-4}$ alkoxy group, a halogenated $C_{1-4}$ alkyl group, arylalkoxy (optionally substituted), hydroxy, a phenyl $C_{1-6}$ alkyl group (optionally substituted), a ($C_{2-6}$ alkoxycarbonyl)vinyl group, a group of formula —$S(O)_nR_7$ (in which $R_7$ represents a $C_{1-6}$ alkyl group and n is 0, 1 or 2 or n is 2 and $R_7$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a $C_{2-6}$ alkoxycarbonyl $C_{1-6}$ alkyl group, a carboxy $C_{1-6}$ alkyl group, a carbamoyl group of formula —$CONR_{11}R_{12}$ (in which $R_{11}$ and $R_{12}$ are independently hydrogen, a $C_{1-6}$ alkyl group, a $C_{3-8}$ cycloalkyl group or optionally substituted phenyl or $R_{11}$ and $R_{12}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a carbamoylvinyl group of formula —CH=CH—$CON(R_{11})R_{12}$ in which $R_{11}$ and $R_{12}$ are as previously defined, a group of formula —$OSO_2R_{21}$ in which $R_{21}$ represents a $C_{1-6}$ alkyl group or a phenyl group (optionally substituted), 4,5-dihydrothiazol-2-yl, 4,4-dimethyl-2-oxazolin-2-yl or a group of formula —$NR_{60}R_{61}$ [in which $R_{60}$ represents hydrogen or a $C_{1-6}$ alkyl group and $R_{61}$ represents a $C_{1-6}$ alkanoyl group or benzoyl (optionally substituted)];
or $R_1$ represents a group of formula —(O)$_z$—$L_3$G
wherein z equals 0 or 1, $L_3$ represents a $C_{1-4}$ alkylene chain which may be substituted by one or more $C_{1-4}$ alkyl groups and G represents a group of formula a), b), c) or d)

a) —$NR_{22}R_{23}$ in which $R_{22}$ represents hydrogen or a $C_{1-6}$ alkyl group and $R_{23}$ represents hydrogen, a $C_{1-6}$ alkyl group, a $C_{1-6}$ alkanoyl group, phenylsulphonyl (optionally substituted), benzoyl (optionally substituted), a group of formula —$CONR_{24}R_{25}$ (wherein $R_{24}$ represents hydrogen, a $C_{1-6}$ alkyl group or a $C_{3-6}$ cycloalkyl group and $R_{25}$ represents hydrogen, a $C_{1-6}$ alkyl group or phenyl (optionally substituted)) or $R_{24}$ and $R_{25}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups);

b) —$S(O)_mR_{26}$ in which $R_{26}$ represents a $C_{1-6}$ alkyl group, a phenyl group (optionally substituted) and m is 0, 1 or 2 or m is 2 and $R_{26}$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), c) —$CONR_{27}R_{28}$ in which $R_{27}$ represents hydrogen or a $C_{1-6}$ alkyl group and $R_{28}$ represents hydrogen, a $C_{1-6}$ alkyl group, a $C_{3-8}$ cycloalkyl group, a phenyl $C_{1-6}$ alkyl group in which the phenyl ring is optionally substituted, or phenyl (optionally substituted) or $R_{27}$ and $R_{28}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

d) —$OR_{29}$ in which $R_{29}$ represents a $C_{1-6}$ alkyl group, phenyl a(optionally substituted), a phenyl $C_{1-6}$ alkyl group (in which the phenyl ring is optionally substituted), a $C_{1-6}$ alkanoyl group, benzoyl (optionally substituted), a $C_{1-6}$ alkylsulphonyl group, a phenylsulphonyl group (optionally substituted), or $R_{29}$ represents a group of formula —$L_4COR_{32}$ in which $L_4$ represents a $C_{1-4}$ alkylene chain (optionally substituted by one or more $C_{1-4}$ alkyl groups), and $R_{32}$ represents hydrogen, a $C_{1-6}$ alkyl group, a $C_{1-6}$ alkoxy group, phenyl (optionally substituted) or phenoxy (optionally substituted);

$R_2$ and $R_3$ independently represent hydrogen, halo, a $C_{1-6}$ alkyl group (optionally substituted by one or more hydroxy groups), a $C_{1-6}$ alkoxy group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a halogenated $C_{1-4}$ alkoxy group, a halogenated $C_{1-4}$ alkyl group, hydroxy, a group of formula —$S(O)_nR_7$ (in which $R_7$ represents a $C_{1-6}$ alkyl group and n is 0, 1 or 2 or n is 2 and $R_7$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$NR_{60}R_{61}$ [in which $R_{60}$ represents hydrogen or a $C_{1-6}$ alkyl group and $R_{61}$ represents a $C_{1-6}$ alkanoyl group, or benzoyl (optionally substituted)];

or $R_1$ and $R_2$ together with the phenyl ring to which they are attached represent a naphthyl group (optionally substituted);

or $R_2$ is attached to a position on the phenyl ring adjacent to the position of attachment of $L_2$ on the phenyl ring and $L_2$ and $R_2$ together with the phenyl ring to which they are attached represent an indane ring which is optionally substituted;

$L_2$ represents a $C_{1-4}$ alkylene chain, a $C_{3-6}$ cycloalkylene group, or a $C_{3-6}$ cycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups;

$R_6$ represents hydrogen, a $C_{1-4}$ alkyl group (optionally substituted by one or more hydroxy groups or by a $C_{2-6}$ alkoxycarbonyl group);

Q represents a $C_{1-9}$ alkylene chain [optionally substituted by one or more hydroxy groups and/or by one or more $C_{1-4}$ alkyl groups (optionally substituted by one or more hydroxy groups) and/or optionally interrupted by oxygen or a carbonyl group];

Y represents an imidazole ring of formula (2), (3) or (4)

(2)

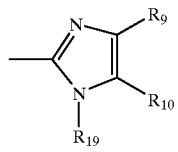

(3)

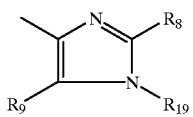

(4)

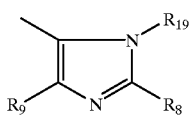

in which $R_8$ represents hydrogen, a $C_{1-6}$ alkyl group, halo, a halogenated $C_{1-6}$ alkyl group, a $C_{1-4}$ alkoxy group, a halogenated $C_{1-4}$ alkoxy group, a $C_{1-4}$ hydroxyalkyl group, phenyl (optionally substituted), benzoyl (optionally substituted), a benzoyl $C_{1-4}$ alkyl group (optionally substituted), or a phenyl $C_{1-4}$ alkyl group in which the alkyl chain is optionally substituted by one or more hydroxy groups or one or more $C_{1-4}$ alkyl groups and the phenyl ring is optionally substituted;

$R_9$ and $R_{10}$ independently represent hydrogen, a $C_{1-6}$ alkyl group, halo, a halogenated $C_{1-6}$ alkyl group, a $C_{1-4}$ alkoxy group, a halogenated $C_{1-4}$ alkoxy group, phenyl (optionally substituted), a $C_{1-4}$ hydroxyalkyl group, a $C_{2-6}$ alkoxycarbonyl group, nitro, an amino group of formula $NR_{30}R_{31}$ (in which $R_{30}$ and $R_{31}$ are independently hydrogen or a $C_{1-4}$ alkyl group or $R_{30}$ and $R_{31}$ together with the nitrogen atom to which they are attached form a pyrrolidine ring, a morpholine ring or a piperidine ring), a $C_{1-6}$ alkanoyloxy $C_{1-4}$ alkyl group, a cyano $C_{1-6}$ alkyl group, or a group of formula g) or h), g) —$L_5$—$NR_{40}R_{41}$ in which $L_5$ represents a $C_{1-4}$ alkylene chain (optionally substituted by one or more $C_{1-4}$ alkyl groups), $R_{40}$ represents hydrogen or a $C_{1-6}$ alkyl group, and $R_{41}$ represents hydrogen, a $C_{1-6}$ alkyl group, a group of formula $SO_2R_{42}$ [in which $R_{42}$ represents a $C_{1-6}$ alkyl group or phenyl (optionally substituted)], a group of formula $COR_{43}$ [in which $R_{43}$ represents a $C_{1-6}$ alkyl group, phenyl (optionally substituted), pyridyl (optionally substituted), thienyl (optionally substituted), furyl (optionally substituted) or pyrrolyl (optionally substituted), a $C_{1-6}$ alkoxy group, phenoxy (optionally substituted) or arylalkyl (optionally substituted)] or $R_{41}$ represents a group of formula $CONR_{44}R_{45}$ [in which $R_{44}$ represents hydrogen, a $C_{1-6}$ alkyl group or a $C_{3-6}$ cycloalkyl group and $R_{45}$ represents hydrogen, a $C_{1-6}$ alkyl group or phenyl (optionally substituted) or $R_{44}$ and $R_{45}$ together with the nitrogen atom to which they are attached form a pyrrolidine ring, a piperidine ring or a morpholine ring]; or h) —$L_7CONR_{90}R_{91}$ in which $L_7$ represents a $C_{1-6}$ alkylene chain and $R_{90}$ and $R_{91}$ are independently hydrogen, a $C_{1-6}$ alkyl group or phenyl (optionally substituted) or $R_{90}$ and $R_{91}$ together with the nitrogen atom to which they are attached form a pyrrolidine ring, a morpholine ring or a piperidine ring; and $R_{19}$ represents hydrogen, a $C_{1-6}$ alkyl group, an aryl group or an aryl $C_{1-6}$ alkyl group.

A first preferred group of compounds of formula IIc is now given.

Preferably $R_1$ represents hydrogen, halo, a $C_{1-8}$ alkyl group (optionally substituted by one or more hydroxy groups), a $C_{1-4}$ alkoxy group, hydroxy, a carbamoyl group of formula $CONR_{11}R_{12}$ (in which $R_{11}$ and $R_{12}$ are independently hydrogen, a $C_{1-6}$ alkyl group, a $C_{3-8}$ cycloalkyl group or optionally substituted phenyl, or $R_{11}$ and $R_{12}$ together with a nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$S(O)_nR_7$ in which n is 2, and $R_7$ represents a group of formula —$N(R_{17})R_{18}$ (in which $R_{17}$ and $R_{18}$ independently represent hydrogen, a $C_{1-6}$ alkyl group or optionally substituted phenyl), or $R_1$ represents a group of formula —$L_3G$ in which $L_3$ represents a $C_{1-4}$ alkylene chain which may be substituted by one or more $C_{1-4}$ alkyl groups and G represents a group of formula a, b or c:

a) —$NR_{22}R_{23}$ wherein $R_{22}$ represents hydrogen or a $C_{1-6}$ alkyl group and $R_{23}$ represents hydrogen or phenylsulphonyl (optionally substituted);

b) —$S(O)_mR_{26}$ in which $R_{26}$ represents a $C_{1-6}$ alkyl group and m is 0, 1 or 2;

c) —$CONR_{27}R_{28}$ in which $R_{27}$ represents hydrogen or a $C_{1-6}$ alkyl group and $R_{28}$ represents hydrogen, a $C_{1-6}$ alkyl group or phenyl (optionally substituted);

$R_2$ and $R_3$ independently represent hydrogen, halo, a $C_{1-6}$ alkyl group, or a $C_{1-6}$ alkoxy group;

$L_2$ represents a $C_{1-4}$ alkylene chain (optionally substituted by one or more $C_{1-4}$ alkyl groups);

Q represents a $C_{2-6}$ alkylene chain;

Y represents a group of formula 2);

$R_9$ and $R_{10}$ represent hydrogen; and $R_{19}$ represents hydrogen or benzyl.

A second preferred group of compounds of formula IIc is now given.

Preferably $R_1$ represents hydrogen or halo. More preferably $R_1$ represents hydrogen or chloro. Most preferably $R_1$ represents chloro.

Preferably $R_2$ and $R_3$ each represent hydrogen.

Preferably $L_2$ represents —$C(R_4)(R_5)$— in which $R_4$ and $R_5$ independently represent hydrogen, methyl or ethyl. More preferably $R_4$ and $R_5$ both represent methyl.

Preferably $R_6$ represents hydrogen or a $C_{1-4}$ alkyl group. More preferably $R_6$ represents hydrogen.

Preferably Q represents methylene, ethylene or trimethylene. More preferably Q represents ethylene.

Preferably Y represents imidazol-2-yl, or imidazol-4(5)-yl. More preferably Y represents imidazol-4(5)-yl.

A fifth group of preferred compounds of formula I is represented by formula IId

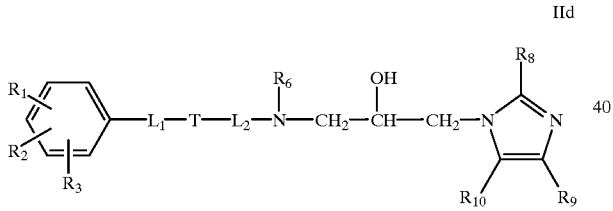

IId and pharmaceutically acceptable salts thereof in which $R_1$ represents hydrogen, halo, cyano, a cyano $C_{1-6}$ alkyl group, a $C_{1-12}$ alkyl group (optionally substituted by one or more hydroxy groups), a $C_{1-6}$ alkoxy group, phenoxy (optionally substituted), phenyl (optionally substituted), a $C_{2-6}$ alkoxycarbonyl group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a group of formula —$N(R_{15})SO_2R_{16}$ (in which $R_{15}$ represents hydrogen or $C_{1-6}$ alkyl and $R_{16}$ represents hydroxy, a $C_{1-6}$ alkyl group or optionally substituted phenyl), a halogenated $C_{1-4}$ alkoxy group, a halogenated $C_{1-4}$ alkyl group, arylalkoxy (optionally substituted), hydroxy, a phenyl $C_{1-6}$ alkyl group (optionally substituted), a ($C_{2-6}$ alkoxycarbonyl)vinyl group, a group of formula —$S(O)_nR_7$ (in which $R_7$ represents a $C_{1-6}$ alkyl group and n is 0, 1 or 2 or n is 2 and $R_7$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a $C_{2-6}$ alkoxycarbonyl $C_{1-6}$ alkyl group, a carboxy $C_{1-6}$ alkyl group, a carbamoyl group of formula —$CONR_{11}R_{12}$ (in which $R_{11}$ and $R_{12}$ are independently hydrogen, a $C_{1-6}$ alkyl group, a $C_{3-8}$ cycloalkyl group or optionally substituted phenyl or $R_{11}$ and $R_{12}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a carbamoylvinyl group of formula —CH=CH—$CON(R_{11})R_{12}$ in which $R_{11}$ and $R_{12}$ are as previously defined, a group of formula —$OSO_2R_{21}$ in which $R_{21}$ represents a $C_{1-6}$ alkyl group or a phenyl group (optionally substituted), 4,5-dihydrothiazol-2-yl, 4,4-dimethyl-2-oxazolin-2-yl or a group of formula —$NR_{60}R_{61}$ [in which $R_{60}$ represents hydrogen or a $C_{1-6}$ alkyl group and $R_{61}$ represents a $C_{1-6}$ alkanoyl group or benzoyl (optionally substituted)];

or $R_1$ represents a group of formula —$(O)_z$—$L_3G$ wherein z equals 0 or 1, $L_3$ represents a $C_{1-4}$ alkylene chain which may be substituted by one or more $C_{1-4}$ alkyl groups and G represents a group of formula a), b), c) or d)

a) —$NR_{22}R_{23}$ in which $R_{22}$ represents hydrogen or a $C_{1-6}$ alkyl group and $R_{23}$ represents hydrogen, a $C_{1-6}$ alkyl group, a $C_{1-6}$ alkanoyl group, phenylsulphonyl (optionally substituted), benzoyl (optionally substituted), a group of formula —$CONR_{24}R_{25}$ (wherein $R_{24}$ represents hydrogen, a $C_{1-6}$ alkyl group or a $C_{3-6}$ cycloalkyl group and $R_{25}$ represents hydrogen, a $C_{1-6}$ alkyl group or phenyl (optionally substituted)) or $R_{24}$ and $R_{25}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups);

b) —$S(O)_mR_{26}$ in which $R_{26}$ represents a $C_{1-6}$ alkyl group, a phenyl group (optionally substituted) and m is 0, 1 or 2 or m is 2 and $R_{26}$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), c) —$CONR_{27}R_{28}$ in which $R_{27}$ represents hydrogen or a $C_{1-6}$ alkyl group and $R_{28}$ represents hydrogen, a $C_{1-6}$ alkyl group, a $C_{3-8}$ cycloalkyl group, a phenyl $C_{1-6}$ alkyl group in which the phenyl ring is optionally substituted, or phenyl (optionally substituted) or $R_{27}$ and $R_{28}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

d) —$OR_{29}$ in which $R_{29}$ represents a $C_{1-6}$ alkyl group, phenyl (optionally substituted), a phenyl $C_{1-6}$ alkyl group (in which the phenyl ring is optionally substituted), a $C_{1-6}$ alkanoyl group, benzoyl (optionally substituted), a $C_{1-6}$ alkylsulphonyl group, a phenylsulphonyl group (optionally substituted), or $R_{29}$ represents a group of formula —$L_4COR_{32}$ in which $L_4$ represents a $C_{1-4}$ alkylene chain (optionally substituted by one or more $C_{1-4}$ alkyl groups), and $R_{32}$ represents hydrogen, a $C_{1-6}$ alkyl group, a $C_{1-6}$ alkoxy group, phenyl (optionally substituted) or phenoxy (optionally substituted);

$R_2$ and $R_3$ independently represent hydrogen, halo, a $C_{1-6}$ alkyl group (optionally substituted by one or more hydroxy groups), a $C_{1-6}$ alkoxy group, an amino group of formula —$NR_{13}R_{14}$ (in which $R_{13}$ and $R_{14}$ are independently hydrogen or a $C_{1-4}$ alkyl group or $R_{13}$ and $R_{14}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a halogenated $C_{1-4}$ alkoxy group, a halogenated $C_{1-4}$ alkyl group, hydroxy, a group of formula —$S(O)_nR_7$ (in which $R_7$ represents a $C_{1-6}$ alkyl group and n is 0, 1 or 2 or n is 2 and $R_7$ represents a group of formula —$N(R_{17})R_{18}$ in which $R_{17}$ and $R_{18}$ independently represent hydrogen, a $C_{1-6}$ alkyl group, a $C_{3-6}$ cycloalkyl group or optionally substituted phenyl or $R_{17}$ and $R_{18}$ together with the nitrogen atom to which they are attached form a pyrrolidine ring, a morpholine ring or a piperidine ring) or a group of formula —$NR_{60}R_{61}$ (in which $R_{60}$ represents hydrogen or a $C_{1-6}$ alkyl group and $R_{61}$ represents a $C_{1-6}$ alkanoyl group, or benzoyl (optionally substituted)];

or $R_1$ and $R_2$ together with the phenyl ring to which they are attached represent a naphthyl group (optionally substituted);

or $R_2$ is attached to a position on the phenyl ring adjacent to the position of attachment of $L_1$ on the phenyl ring and —$L_1$—T—$L_2$— and $R_2$ together with the phenyl ring to which they are attached represent an indane ring which is optionally substituted;

$L_1$ represents e) a bond, or f) a $C_{1-4}$ alkylene chain, a $C_{3-6}$ cycloalkylene group, or a $C_{3-6}$ cycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups;

T represents a bond or O, S, SO, $SO_2$, a carbonyl group, or a group of formula 5)

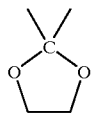

$L_2$ represents a $C_{1-4}$ alkylene chain, a $C_{3-6}$ cycloalkylene group, or a $C_{3-6}$ cycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups; and when T represents a carbonyl group $L_2$ additionally represents a $C_{1-4}$ oxyalkylene chain, a $C_{3-6}$ oxycycloalkylene group, or a $C_{3-6}$ oxycycloalkylidene group, each of which is optionally substituted by one or more phenyl groups (optionally substituted), by one or more $C_{1-4}$ alkyl groups (wherein the alkyl groups are optionally substituted by one or more hydroxy groups or a $C_{2-6}$ alkoxycarbonyl group) or by one or more $C_{3-6}$ cycloalkyl groups;

$R_6$ represents hydrogen, a $C_{1-4}$ alkyl group (optionally substituted by one or more hydroxy groups or by a $C_{2-6}$ alkoxycarbonyl group);

$R_8$ represents hydrogen, a $C_{1-6}$ alkyl group, halo, a halogenated $C_{1-6}$ alkyl group, a $C_{1-4}$ alkoxy group, a halogenated $C_{1-4}$ alkoxy group, a $C_{1-4}$ hydroxyalkyl group, phenyl (optionally substituted), benzoyl (optionally substituted), a benzoyl $C_{1-4}$ alkyl group (optionally substituted), or a phenyl $C_{1-4}$ alkyl group in which the alkyl chain is optionally substituted by one or more hydroxy groups or one or more $C_{1-4}$ alkyl groups and the phenyl ring is optionally substituted;

$R_9$ and $R_{10}$ independently represent hydrogen, a $C_{1-6}$ alkyl group, halo, a halogenated $C_{1-6}$ alkyl group, a $C_{1-4}$ alkoxy group, a halogenated $C_{1-4}$ alkoxy group, phenyl (optionally substituted), a $C_{1-4}$ hydroxyalkyl group, a $C_{2-6}$ alkoxycarbonyl group, nitro, an amino group of formula $NR_{30}R_{31}$ (in which $R_{30}$ and $R_{31}$ are independently hydrogen or a $C_{1-4}$ alkyl group or $R_{30}$ and $R_{31}$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups), a $C_{1-6}$ alkanoyloxy $C_{1-4}$ alkyl group, a cyano $C_{1\,6}$ alkyl group, or a group of formula g) or h), g) —$L_5$—$NR_{40}R_{41}$ in which $L_5$ represents a $C_{1-4}$ alkylene chain (optionally substituted by one or more $C_{1-4}$ alkyl groups), $R_{40}$ represents hydrogen or a $C_{1-6}$ alkyl group, and $R_{41}$ represents hydrogen, a $C_{1-6}$ alkyl group, a group of formula $SO_2R_{42}$ [in which $R_{42}$ represents a $C_{1-6}$ alkyl group or phenyl (optionally substituted)], a group of formula $COR_{43}$ [in which $R_{43}$ represents a $C_{1-6}$ alkyl group, phenyl (optionally substituted), pyridyl (optionally substituted), thienyl (optionally substituted), furyl (optionally substituted) or pyrrolyl (optionally substituted), a $C_{1-6}$ alkoxy group, phenoxy (optionally substituted) or arylalkyl (optionally substituted)] or $R_{41}$ represents a group of formula CONR$_{44}$R$_{45}$ [in which R$_{44}$ represents hydrogen, a C$_{1-6}$ alkyl group or a C$_{3-6}$ cycloalkyl group and R$_{45}$ represents hydrogen, a C$_{1-6}$ alkyl group or phenyl (optionally substituted) or R$_{44}$ and R$_{45}$ together with the nitrogen atom to which they are attached form a pyrrolidine ring, a piperidine ring or a morpholine ring]; or h) —L$_7$CONR$_{90}$R$_{91}$ in which L$_7$ represents a C$_{1-6}$ alkylene chain and R$_{90}$ and R$_{91}$ are independently hydrogen, a C$_{1-6}$ alkyl group or phenyl (optionally substituted) or R$_{90}$ and R$_{91}$ together with the nitrogen atom to which they are attached represent a saturated 3–7 membered heterocyclic ring, optionally containing sulphur, oxygen or an additional nitrogen atom, wherein the ring may be optionally substituted by one or more C$_{1-4}$ alkyl groups.

Preferably R$_1$ represents hydrogen, halo, C$_{2-6}$ alkoxycarbonyl group, a group of formula —S(O)$_n$R$_7$ (in which R$_7$ represents a C$_{1-6}$ alkyl group and n is 0), hydroxy, a carbamoyl group —CONR$_{11}$R$_{12}$ (in which R$_{11}$ and R$_{12}$ independently represent hydrogen, a C$_{1-6}$ alkyl group, or a C$_{3-8}$ cycloalkyl group), 4,4-dimethyl-2-oxazolin-2-yl or a group of formula L$_3$G in which L$_3$ represents a C$_{1-4}$ alkylene chain and G represents a group of formula b) or c):

b) —S(O)$_m$R$_{26}$ in which m is 2 and R$_{26}$ represents a phenyl group (optionally substituted);
c) —CONR$_{27}$R$_{28}$ in which R$_{27}$ represents hydrogen or a C$_{1-6}$ alkyl group and R$_{28}$ represents hydrogen, a C$_{1-6}$ alkyl group or a C$_{3-8}$ cycloalkyl group;

R$_2$ and R$_3$ represent hydrogen or a C$_{1-6}$ alkyl group;

L$_1$ represents a bond;

T represents oxygen or a bond;

R$_2$ represents a C$_{1-4}$ alkylene chain (optionally substituted by one or more C$_{1-4}$ alkyl groups);

R$_6$ represents hydrogen;

R$_8$ represents hydrogen;

R$_9$ and R$_{10}$ independently represent hydrogen or a group of formula —L$_5$—NR$_{40}$R$_{41}$ in which L$_5$ represents a C$_{1-4}$ alkyl chain (optionally substituted by C$_{1-4}$ alkyl groups), R$_{40}$ represents hydrogen and R$_{41}$ represents a benzoyl group (optionally substituted).

A preferred group of compounds of formula IId is now given.

Preferably R$_1$ is located at the 4-position of the phenyl ring and represents hydrogen, hydroxy, chloro, N-cyclohexylcarbamoyl, 4,4-dimethyl-2-oxazolin-2-yl, n-propoxycarbonyl, 3,4-dimethylphenylsulphonylmethyl, methylthio and N-hexylcarbamoylmethyl. More preferably R$_1$ represents chloro.

Preferably R$_2$ and R$_3$ independently represent hydrogen or a C$_{1-4}$ alkyl group.

Preferably —L$_1$—T—L$_2$— represents —C(CH$_3$)$_2$—, —C(C$_2$H$_5$)$_2$— or —O—CH$_2$—C(CH$_3$)$_2$—.

Preferably R$_8$ represents hydrogen.

Preferably R$_9$ and R$_{10}$ independently represent hydrogen or 2-(benzamido)ethyl.

Specific compounds of formula I are:
2-(4-chlorophenoxy)-3'-(imidazol-1-yl)-2-methyldipropylamine
N-[2-(4-chlorophenoxy)ethyl]-3-(imidazol-1-yl)propylamine
3-(imidazol-1-yl)-N-(2-phenoxyethyl)propylamine
2-(2-chlorophenoxy)-3'-(imidazol-1-yl)-2-methyldipropylamine
N-[2-(4-ethylphenoxy)ethyl]-3-(imidazol-1-yl)propylamine
N-[2-(3,4-dimethylphenoxy)ethyl]-3-(imidazol-1-yl)propylamine
N-[2-(4-fluorophenoxy)ethyl]-3-(imidazol-1-yl)propylamine
N-[2-(4-chlorophenoxy)ethyl]-3-(2-methylimidazol-1-yl)propylamine
3-(4-chlorophenoxy)-3'-(imidazol-1-yl)dipropylamine
N-[2-(4-benzyloxyphenoxy)ethyl]-3-(imidazol-1-yl)propylamine
N-[2-(4-chlorophenylthio)ethyl]-3-(imidazol-1-yl)propylamine
3-(4-chlorophenyl)-3'(2-methylimidazol-1-yl)-dipropylamine
2-(4-chlorophenyl)-3'-(imidazol-1-yl)-2-methyldipropylamine
3-(4-chlorophenyl)-3'-(imidazol-1-yl)dipropylamine
2-(4-chlorophenoxy)-3'-(imidazol-1-yl)dipropylamine
N-[2-(4-chlorophenoxy)ethyl]-5-(imidazol-1-yl)pentylamine
N-[2-(4-chlorophenoxy)-1,1-dimethylethyl]-3-(imidazol-1-yl)propylamine
2-(4-chlorophenylthio)-3'-(imidazol-1-yl)-2-methyldipropylamine
N-[2-(4-chlorophenylthio)-1,1-dimethylethyl]-3-(imidazol-1-yl)propylamine
N-[2-(4-chloro-2,5-xylylthio)-1,1-dimethylethyl]-3-imidazol-1-yl)propylamine
N-[2-(4-chlorophenyl)-1,1-dimethylethyl]-3-(imidazol-1-yl)propylamine
3-[4-(2-aminoethyl)imidazol-1-yl]—N-[1-(4-chlorophenyl)-1-methylethyl]propylamine
α-(1-{3-[1-(4-chlorophenyl)-1-methylethylamino]propyl}imidazol-2-yl)benzyl alcohol
3-(imidazol-1-yl)-N-{1-methyl-1-[4-(3,4-xylylsulphonylmethyl)phenyl]ethyl}propylamine
N-{1-[(hexylsulphonylmethyl)phenyl]-1-methylethyl}-3-(imidazol-1-yl)propylamine
4-{1-[3-(imidazol-1-yl)propylamino]-1-methylethyl}-N,N-dipropylbenzenesulphonamide
N-{1-[4-(2-benzyloxyethyl)phenyl]-1-methylethyl}-3-(imidazol-1-yl)propylamine
N-cyclohexyl-4-{1-[3-(imidazol-1-yl)propylamino]-1-methylethyl}benzamide
N-hexyl-4-{1-[3-(imidazol-1-yl)propylamino]-1-methylethyl}phenylacetamide
N-(4-chlorobenzyl)-4-{1-[3-(imidazol-1-yl)propylamino]-1-methylethyl}phenylacetamide
4-{2-[3-(imidazol-1-yl)propylamino]ethoxy}benzonitrile
N-{2-[2-(4-chlorophenyl)-1,3-dioxolan-2-yl]ethyl}-3-(imidazol-1-yl)propylamine
N-[1,1-dimethyl-2-(4-methylthiophenoxy)ethyl]-3-(imidazol-1-yl)propylamine
4-{1-[3-(imidazol-1-yl)propylamino]-1-propylbutyl}-phenyl-N-methylacetamide
3-(imidazol-1-yl)-N-(1,1-dimethyl-2-phenoxyethyl) propylamine
3'-(imidazol-1-yl)-3-(2-methoxyphenyl)-1,1-dimethyldipropylamine
N-cycloheptyl-4-{1-[3-(imidazol-1-yl)propylamino]-1-methylethyl}phenylacetamide 4-cyano-N-[2-(4-{1-[3-(imidazol-1-yl)propylamino]-1-methylethyl}phenyl)ethyl]benzenesulphonamide N-{2-[4-(trifluoromethyl)phenoxy]-1,1-dimethylethyl}-3-(imidazol-1-yl)propylamine N-[2-(4-fluorophenoxy)-1,1-dimethylethyl]-3-(imidazol-1-yl)propylamine 2-ethyl-2-(4-{1-[3-(imidazol-1-yl)propylamino]-1-methylethyl}phenyl)butan-1-ol N-[2-(4-{1-[3-(imidazol-1-yl)propylamino]-1-methylethyl}phenyl)ethyl]-4-methoxybenzenesulphonamide 1-[1-(4-chlorophenyl)-1-methylethylamino]-3-(imidazol-1-yl)propan-2-ol 1-(1-ethyl-1-phenylpropylamino)-3-(imidazol-1-yl)propan-2-ol (+)-1-[1-(4-chlorophenyl)-1-methylethylamino]-3-(imidazol-1-yl)propan-2-ol (−)-1-[1-(4-chlorophenyl)-1-methylethylamino]-3-(imidazol-1-yl)propan-2-ol N-hexyl-4-{1-[2-hydroxy-3-(imidazol-1-yl)propylamino]-1-methylethyl}phenylacetamide N-cyclohexyl-4-{1-[2-hydroxy-3-(imidazol-1-yl)propylamino]-1-methylethyl}benzamide 1-{1-[4-(4,4-dimethyl-2-oxazolin-2-yl)phenyl]-1-methylethylamino}-3-(imidazol-1-yl)propan-2-ol 1-(imidazol-1-yl)-3-{1-methyl-1-[4-(3,4-xylylsulphonylethyl)phenyl]ethylamino}propan-2-ol 3-(imidazol-1-yl)-1-[2-(4-methylthiophenoxy)-1,1-dimethylethylamino]propan-2-ol 1-[2-(4-chlorophenoxy)-1,1-dimethylethylamino]-3-(imidazol-1-yl)propan-2-ol 3-(imidazol-1-yl)-1-(2-phenoxy-1,1-dimethylethylamino) propan-2-ol N-[2-(1-{3-[1-(4-chlorophenyl)-1-methylethylamino]propyl}imidazol-4-yl)ethyl]benzene-sulphonamide N-[2-(1-{3-[1-(4-chlorophenyl)-1-methylethylamino]propyl}imidazol-4-yl)ethyl]benzamide N-[2-(4-{1-[3-(imidazol-1-yl)propylamino]-1-methylethyl}phenyl)ethyl]benzenesulphonamide N-[2-(4-{1-[3-(imidazol-1-yl)propylamino]-1-methylethyl}phenyl)ethyl]benzamide N-butyl-N'-[2-(4-{1-[3-(imidazol-1-yl)propylamino]-1-methylethyl}phenyl)ethyl]urea 4'-{1-[3-(imidazol-1-yl)propylamino]-1-methylethyl}biphenyl-4-ol N-(2-{1-[3-(1-ethyl-1-phenylpropylamino)propyl]imidazol-4-yl}ethyl)benzamide N-(2-{1-[3-(1-ethyl-1-phenylpropylamino)propyl]imidazol-4-yl}ethyl)-4-methoxybenzamide 4-cyano-N-(2-{1-[3-(1-ethyl-1-phenylpropylamino)propyl]imidazol-4-yl}ethyl)benzamide N-[2-(1-{3-[1-(4-chlorophenyl)-1-methylethylamino]-2-hydroxypropyl}imidazol-4-ylethyl]benzamide N-[2-(4-chlorophenoxy)ethyl]-3-(imidazol-1-yl)-N-methylpropylamine methyl N-[2-(4-chlorophenoxy)ethyl]—N-[3-(imidazol-1-yl)-propyl]glycinate 2-{N-[2-(4-chlorophenoxy)-ethyl]—N-[3-(imidazol-1-yl)propyl]amino}ethanol 4-{2-[3-(imidazol-1-yl)propylamino]ethoxy}phenyl 1-butanesulphonate N-[2-(4-chlorophenylsulphinyl)-1,1-dimethylethyl]-3-(imidazol-1-yl)propylamine N-[2-(4-chloro-2,5-xylylsulphonyl)-1,1-dimethylethyl]-3-(imidazol-1-yl)propylamine N-[2-(4-t-butylphenylsulphonyl)-1,1-dimethylethyl]-3-(imidazol-1-yl)-propylamine 4-{1-[3-(imidazol-1-yl)propylamino]-1-methylethyl}phenyl benzenesulphonate 4-{1-[3-(imidazol-1-yl)propylamino]-1-methylethyl}phenyl 1-butanesulphonate 2'-chloro-5'-{1-[3-(imidazol-1-yl)propylamino]-1-methylethyl}benzanilide propyl 4-{1-[2-hydroxy-3-(imidazol-1-yl) propylamino]-1-methylethyl}benzoate 5-(imidazol-1-yl)-N-(1,1-dimethyl-2-phenoxyethyl)pentylamine N-(2-{1-[3-(1,1-dimethyl-2-phenoxyethylamino)propyl]imidazol-4-yl}ethyl)benzamide N-(2-{1-[3-(1,1-dimethyl-2-phenoxyethylamino)propyl]imidazol-5-yl}ethyl)benzamide N-(2-{1-[3-(1,1-dimethyl-2-phenoxyethylamino)propyl]imidazol-4-yl}ethyl]benzenesulphonamide N-(2-{1-[3-(1,1-dimethyl-2-phenoxyethylamino)propyl]imidazol-5-yl}ethyl]benzenesulphonamide 2-[3-(imidazol-1-yl)propylamino]-2,2-dimethylethyl benzoate 2-[3-(imidazol-1-yl)propylamino]-2,2-dimethylethyl 4-chlorobenzoate N-[2-(4-chlorobenzyloxy)-1,1-dimethylethyl]-3-(imidazol-1-yl)propylamine N-(3-phenylpropyl)-5-(imidazol-1-yl)pentylamine 3-[4-(butylaminomethyl)imidazol-1-yl]-N-[1-(4-chlorophenyl)-1-methylethyl]propylamine 1-(4-chlorophenyl)-N-(imidazol-2-ylmethyl)-1-methylethylamine N-[1-(4-chlorophenyl)-1-methylethyl]-3-(imidazol-4(5)-yl)propylamine 1-(4-chlorophenyl)-2'-(imidazol-4(5)-yl)-1-methyldiethylamine 3-(1-benzylimidazol-2-yl)-N-[1-(4-chlorophenyl)-1-methylethyl]propylamine 3-(imidazol-2-yl)-N-(1-methyl-1-phenylethyl)propylamine N-(5-chloroindan-1-yl)-3-(imidazol-1-yl)propylamine N-[2-(4-{1-[3-(imidazol-2-yl)propylamino]-1-methylethyl}phenyl)ethyl]-4-methoxybenzenesulphonamide N-(1-ethyl-1-phenylpropyl)-3-(imidazol-2-yl)propylamine 2-(4-{1-[3-(imidazol-2-yl)propylamino]-1-methylethyl}phenyl)ethanol 4-{1-[3-(imidazol-2-yl)propylamino]-1-methylethyl}-N,N-dipropylbenzenesulphonamide 3'-(imidazol-2-yl)-3-(2-methoxyphenyl)-1,1-dimethyldipropylamine 3-(imidazol-2-yl)-N-(1,1-dimethyl-2-phenoxyethyl)propylamine 1-[1-(4-hydroxy-3-propylphenyl)-1-methylethylamino]-3-(imidazol-1-yl)propan-2-ol N-[2-(4-{1-[3-(imidazol-2-yl)propylamino-1-methylethyl}phenyl)ethyl]benzenesulphonamide 2-ethyl-2-(4-{1-[3-(imidazol-2-yl)propylamino]-1-methylethyl}phenyl)butan-1-ol N-cyclohexyl-4-{1-[3-(imidazol-2-yl)propylamino]-1-methylethyl}benzamide 4-{1-[3-(imidazol-2-yl)propylamino]-1-methylethyl}-2-propylphenol 2-(4-{1-[3-(imidazol-2-yl)propylamino]-1-methylethyl}phenyl)-N,2,2-triethylacetamide 3,4-dihydroxy-N-[2-(4-{1-[3-(imidazol-2-yl)propylamino]-1-methylethyl}phenyl)ethyl]benzenesulphonamide 4-{N-[2-(4-{1-[3-(imidazol-2-yl)propylamino]-1-methylethyl}phenyl)ethylsulphamoyl]}-N-methylbenzamide N-hexyl-4-{1-[3-(imidazol-2-yl)propylamino]-1-methylethyl}phenylacetamide 2-(4-{1-[3-(imidazol-2-yl)propylamino]-1-methylethyl}phenyl)-N-methylacetamide N-{1-[4-(hexylsulphonylmethyl)phenyl]-1-methylethyl}-3-(imidazol-2-yl)propylamine N-[2-(4-methoxyphenoxy)-1,1-dimethylethyl]-3-(imidazol-2-yl)propylamine N-[1,1-dimethyl-2-(4-methylphenoxy)ethyl]-3-(imidazol-2-yl)propylamine N-[2-(4-methoxyphenoxy)-1,1-dimethylethyl]-3-(imidazol-1-yl)propylamine N-{1,1-dimethyl-2-[4-(4,5-dihydrothiazol-2-yl)phenoxy]ethyl}-3-(imidazol-1-yl)propylamine N-hexyl-2-(4-{1-[3-(imidazol-1-yl)propylamino]-1-methylethyl}phenoxy)acetamide 4-{1-[-3-(imidazol-1-yl)propylamino]-1-methylethyl}-N-pentylcinnamamide N-[2-(4-{1-[3-(imidazol-1-yl)propylamino]-1-methylethyl}phenyl)ethyl]-4-methoxybenzenesulphonamide 2-ethyl-2-(4-{1-[3-(imidazol-1-yl)propylamino]-1-methylethyl}phenyl)butan-1-ol 3-(4-{1-[3-(imidazol-1-yl)propylamino]-1-methylethyl}phenyl)-N-pentylpropionamide 1-(4-{1-[3-(imidazol-1-yl)propylamino]-1-methylethyl}phenyl)-N-pentylmethanesulphonamide N-[1,1-dimethyl-2-(4-methylphenoxy)ethyl]-3-(imidazol-1-yl)propylamine N-[2-(4-{1-[3-(imidazol-1-yl)propylamino]-1-methylethyl}phenyl)ethyl]-3,4-dimethoxybenzenesulphonamide N-[2-(4-{1-[3-(imidazol-2-yl)propylamino]-1-methylethyl}phenyl)ethyl]-3,4-dimethoxybenzenesulphonamide 1-(2-methoxy-5-{1-[3-(imidazol-1-yl)propylamino]-1-methylethyl}phenyl)pentanol N-[1-(4-methoxy-3-pentylphenyl)-1-methylethyl]-3-(imidazol-1-yl)propylamine 4-{1-[3-(imidazol-1-yl)propylamino]-1-methylethyl}-2-pentylphenol 2-(4-{1-[3-(imidazol-1-yl)propylamino]-1-methylethyl}-2-pentylphenoxy)-N-methylacetamide 2-(4-{1-[3-(imidazol-1-yl)propylamino]-1-methylethyl}-2-pentylphenyl)-N-methylacetamide N-(2-{1-[3-(1-ethyl-1-phenylpropylamino)-2-hydroxypropyl]imidazol-4-yl}ethyl)benzamide 4-{N-[2-(4-{1-[3-(imidazol-1-yl)propylamino]-1-methylethyl}phenyl)ethyl]sulphamoyl)benzamide 3,4-dihydroxy-N-[2-(4-{1-[3-(imidazol-1-yl)propylamino]-1-methylethyl}phenyl)ethyl]benzenesulphonamide 4-{N-[2-(4-{1-[3-(imidazol-1-yl)propylamino]-1-methylethyl}phenyl)ethylsulphamoyl]}-N-methylbenzamide methyl 4-{2-[3-(imidazol-1-yl)propylamino]-2-methylpropoxymethyl}benzoate or pharmaceutically acceptable salts thereof, in the form of individual enantiomers, racemates or other mixtures of enantiomers.

The compounds of formula I may form organic or inorganic salts, for example, the compounds of formula I may form acid addition salts with inorganic or organic acids, e.g. hydrochloric acid, hydrobromic acid, fumaric acid, tartaric acid, citric acid, sulphuric acid, hydriodic acid, phosphoric acid, maleic acid, acetic acid, succinic acid, benzoic acid, pamoic acid, palmitic acid, dodecanoic acid and acidic amino acids such as glutamic acid. Some compounds of formula I may form base addition salts, for example, with alkalis for example sodium hydroxide, or with aminoacids for example, lysine or arginine. It will be appreciated that such salts, provided they are pharmaceutically acceptable may be used in therapy in place of the corresponding compounds of formula I. Such salts are prepared by reacting the compound of formula I with a suitable acid or base in a conventional manner. Such salts may also exist in form of solvates (for example, hydrates).

It will be appreciated by those skilled in the art that certain compounds of formula I contain one or more chiral centres. Thus, compounds in which $R_4$ and $R_5$ are not identical contain a chiral centre. Certain of the substituents $R_1$, $R_2$, $R_3$, $R_4$, $R_5$, $R_6$, $R_8$, $R_9$ and $R_{10}$ may also contain at least one chiral centre, for example when $R_1$, $R_2$, $R_3$, $R_4$, $R_5$, $R_6$, $R_8$, $R_9$ or $R_{10}$ is sec-butyl. Compounds of formula I in which Q represents —CH$_2$—CH(OH)—CH$_2$— contain a chiral centre.

When a compound of formula I contains a single chiral centre it may exist in two enantiomeric forms. The present invention includes individual enantiomers and mixtures of those enantiomers. The enantiomers may be obtained by methods known to those skilled in the art. Such methods typically include resolution via formation of diastereoisomeric salts or complexes which may be separated, for example, by crystallisation; resolution via formation of diastereoisomeric derivatives or complexes which may be separated, for example, by crystallisation, gas-liquid or liquid chromatography; selective reaction of one enantiomer by reaction with an enantiomer-specific reagent, for example, enzymatic esterification, oxidation or reduction, followed by separation of the modified and unmodified enantiomers; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, a further step will subsequently be required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example, chromatography or crystallisation and the individual enantiomers within each pair may be separated as described above. The present invention includes each diastereoisomer of compounds of formula I and mixtures thereof.

Certain compounds of formula I may exist in more than one crystal form and the present invention includes each crystal form and mixtures thereof. Certain compounds of formula I may also exist in the form of solvates, for example hydrates, and the present invention includes each solvate and mixtures thereof.

The present invention also provides pharmaceutical compositions comprising a therapeutically effective amount of a compound of formula I together with a pharmaceutically acceptable diluent or carrier. Such pharmaceutical compositions may be used in the treatment of inflammatory and/or allergic diseases. These compositions may also be used in treatment of diseases.

As used hereinafter, the term "active compound" denotes a compound of formula I. In therapeutic use the active compound may be administered orally, rectally, parenterally, topically, ocularly, aurally, nasally, intravaginally or to the buccal cavity, to give a local and/or a systemic effect. The active compounds may be administered in a prophylactic manner. Thus the therapeutic compositions of the present invention may take the form of any of the known pharmaceutical compositions for such methods of administration. The compositions may be formulated in a manner known to those skilled in the art so as to give a controlled release, for example rapid release or sustained release, of the compounds of the present invention. Pharmaceutically acceptable carriers suitable for use in such compositions are well known in the art of pharmacy. The compositions of the invention suitably contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, granules, syrups and aqueous or oily suspensions. The excipients used in the preparation of these compositions are the excipients known in the pharmacists' art.

Tablets may be prepared from a mixture of the active compound with fillers, for example, lactose or calcium phosphate, disintegrating agents, for example maize starch, lubricating agents, for example magnesium stearate, binders for example microcrystalline cellulose or polyvinyl pyrrolidone and other optional ingredients known in the art to permit tableting the mixture by known methods. The tablets may, if desired, be coated using known methods and excipients which may include enteric coating using for example hydroxypropylmethylcellulose phthalate.

The tablets may be formulated in a manner known to those skilled in the art so as to give a sustained release of the compounds of the present invention. Such tablets may if desired be provided with enteric coatings by known methods, for example by the use of cellulose acetate phthalate.

Similarly capsules, for example hard or soft gelatin capsules containing the active compound with or without added excipients, may be prepared by known methods and, if desired, provided with enteric coatings in a known manner. The contents of the capsule may be formulated using known methods to give sustained release of the active compound. Enteric coated compositions of the invention may be advantageous, depending on the nature of the active compound. The tablets and capsules may conveniently each contain 1–1000 mg (for example 10 mg, 50 mg, 100 mg, 200 mg, 400 mg, 600 mg or 800 mg) of the active compound. Other compositions for oral administration include, for example, aqueous suspensions containing the compound of formula I in an aqueous medium in the presence of a non-toxic suspending agent such as sodium carboxymethylcellulose, and oily suspensions containing a compound of the present invention in a suitable vegetable oil, for example sunflower oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such adminstration, for example suppositories with hard fat, semi-synthetic glycerides or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the active compound is dispersed so that it is held in contact with the skin in order to administer the compound of formula I transdermally. Alternatively the active compound may be dispersed in a cream, gel or ointment base or applied in the form of a spray.

Compositions of the invention suitable for inhalation via the mouth and/or the nose are the known pharmaceutical forms for such administration, for example aerosols, nebulised solutions or powders. Metered dose systems, known to those skilled in the art, may be used.

Compositions suitable for application to the buccal cavity include slow dissolving tablets, troches, chewing gum, gels, pastes, powders, mouthwashes or rinses.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be a) liquid such as an oily solution or suspension of the compound to be infused for example in the form of a very sparingly water-soluble derivative such as a dodecanoate salt or b) solid in the form of an implanted support for example a synthetic resin or waxy material for the compound to be infused. The support may be a single body containing all the compound or a series of several bodies each containing part of the compound to be delivered.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients, for example; a) an analgesic (e.g. in treatment of rheumatoid arthritis), b) a $\beta 2$ agonist (e.g. in treatment of asthma) and c) a non-sedating antihistamine (e.g. in treatment of other allergic conditions).

The pharmaceutical compositions containing a therapeutically effective amount of a compound of formula I may be used to treat inflammatory and/or allergic conditions in human beings. In such treatment the amount of the compound of formula I administered per day is in the range 0.1 to 3000 mg. Specific compounds which may be incorporated into the compositions of this invention are the novel compounds disclosed above.

The therapeutic activity of compounds of formula I has been demonstrated by means of tests on standard laboratory animals. Such tests include, for example, the oral administration of the compounds to rats in which an inflammatory condition is induced. Thus, compounds of formula I are useful for the treatment of inflammatory conditions in mammals. Whilst the precise amount of active compound administered will depend on a number of factors, for example the age of the patient, the severity of the condition and the past medical history and always lies within the sound discretion of the administering physician, a suitable dose for enteral administration to mammals, including humans, is generally within the range 0.01–80 mg/kg/day, more usually 0.2–40 mg/kg/day given in single or divided doses. For parenteral administration, a suitable dose is generally within the range 0.01–80 mg/kg/day, more usually 0.2–40 mg/kg/day given in single or divided doses or by continuous infusion. Oral administration is preferred.

Compounds of formula I and pharmaceutically acceptable salts thereof are indicated for use as medicaments and in particular in the treatment of inflammatory and/or allergic conditions for example musculoskeletal disorders for example: rheumatoid arthritis, osteo-arthritis, systemic lupus erythematosus, muscle trauma, gout, ankylosing spondylitis, tendonitis and bursitis; respiratory disorders for example: asthma and rhinitis; gastrointestinal disorders for example: gastritis, Crohn's disease, ulcerative colitis and other inflammatory diseases of the bowel; diseases of the oral cavity for example: periodontitis and gingivitis; cutaneous disorders for example: psoriasis, urticaria, allergic skin diseases, burns, ocular inflammation and iritis; or Alzheimer's disease. Compounds of formula I and salts thereof may also be useful as analgesics and/or anti-pyretic agents.

Accordingly, in another aspect, the present invention also includes a method of treating inflammatory and/or allergic conditions in a mammal in need of such treatment comprising the administration of a therapeutically effective amount of a compound of formula I (including the compounds of the second, third, fourth and fifth provisos).

While the precise mechanism of action of the compounds of formula I is unknown at present, it is believed that the pharmacological effects arise from the ability of these compounds to inhibit the release of arachidonic acid from phospholipids. Consequently, in a preferred aspect, the present invention provides a method of treating inflammatory and/or allergic conditions comprising the administration of a therapeutically effective amount of an arachidonic acid release inhibitor of formula I (including the compounds of the second, third, fourth and fifth provisos).

In yet another aspect, the present invention provides the use of a compound of formula I (including the compounds of the second, third, fourth and fifth provisos) in the manufacture of a medicament for use in the treatment of an inflammatory and/or allergic condition.

The compounds of formula I are indicated for use as immunomodulatory agents, and are generally immunosuppressants, but some compounds, in certain disease states, may exhibit immunostimulant activity. The compounds according to the invention are useful in the treatment of diseases resulting from an aberrant immune reaction. Thus the pharmaceutical compositions containing a therapeutically effective amount of a compound of formula I may be used to treat diseases with an immunological association for example tissue rejection, such as kidney rejection; autoimmune diseases, such as thyroiditis and type 1 diabetes; cutaneous disorders, such as contact sensitivity and eczema; neoplasia, such as melanoma; and HIV infection.

In such treatment the amount of the compound of formula I administered per day will be such as to give a therapeutic effect and is generally in the range 0.1 to 2000 mg, preferably 1 to 500 mg.

Accordingly, in another aspect, the present invention also includes a method of treating diseases with an immunological association in a mammal in need of such treatment, comprising the administration of a therapeutically effective amount of a compound of formula I (including the compounds of the second, third, fourth and fifth provisos).

The compounds of the present invention are advantageous as it is expected that they will provide an improvement to existing therapies and combine high efficacy with a low incidence of side-effects. Other preferred compounds are those which are expected to have minimal undesirable CNS side-effects as determined by a lack of significant activity in the Porsolt test [Porsolt et al, 1977, Arch. Int. Pharmacodyn. Ther. 229; 326–337; Heal, Luscombe and Martin, 1992, in Central serotonin receptors and psychotropic drugs, (ed. Marsden and Heal) Oxford; Blackwell Scientific Publications] for example.

Processes for the preparation of compounds of formula I will now be described. These processes form a further aspect of the present invention.

Compounds of formula I in which $R_6$ represents hydrogen may be prepared by reacting an imine of formula III

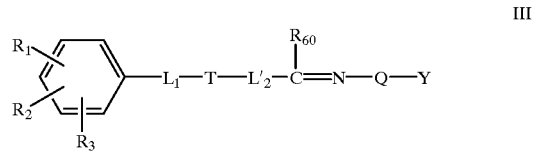

in which $R_1$, $R_2$, $R_3$, $L_1$, T, Q and Y are as previously defined and $—L_2'—C(R_{60})=$ represents a group which on reduction gives $L_2$, with a reducing agent, for example sodium borohydride, in the presence of an inert organic liquid, preferably a solvent for the compound of formula III, e.g. an alcohol, at a temperature in the range 0–150° C., at atmospheric pressure.

Compounds of formula III may be prepared by condensing a compound of formula IV

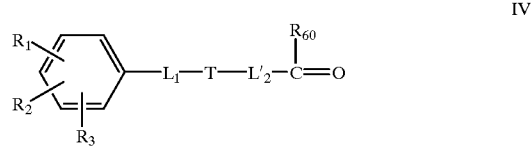

in which $R_1$, $R_2$, $R_3$, $L_1$, T, and $—L_2'—C(R_{60})=$ are as previously defined, with a compound of formula V $$H_2N—Q—Y \qquad \qquad V$$

by heating the two compounds at a temperature in the range 0–200° C. preferably in the range 15–150° C. optionally in the presence of an inert organic liquid which is preferably a solvent for the reactants. Compounds of formula I may be prepared in a two-stage, one-pot process by reacting a compound of formula IV with a compound of formula V by heating at a temperature in the range 0–200° C. and then reducing the intermediate obtained directly for example using sodium borohydride in the presence of an inert organic liquid which is preferably a solvent for the reactants, for example an alcohol, at a temperature in the range 0–150° C., at atmospheric pressure.

Compounds of formula I may also be prepared in a one stage process by reacting a compound of formula IV with a compound of formula V in the presence of a reducing agent for example sodium cyanoborohydride, in the presence of an inert organic liquid, preferably a solvent for the reactants, e.g. an alcohol, at a temperature in the range 0–150° C., at atmospheric pressure.

Compounds of formula I in which $R_6$ represents hydrogen may be prepared by reacting an imine of formula VI

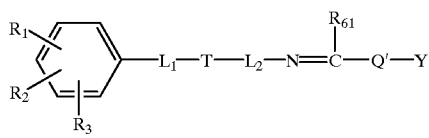

VI in which $R_1$, $R_2$, $R_3$, $L_1$, T, $L_2$ and Y are as previously defined and $=C(R_{61})-Q'-$ represents a group which on reduction gives Q, with a reducing agent, for example sodium borohydride, in the presence of an inert organic liquid which is preferably a solvent for the compounds of formula VI, for example an alcohol, at a temperature in the range 0–200° C., at atmospheric pressure. Compounds of formula VI may be prepared by condensing a compound of formula VII

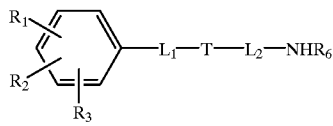

VII in which $R_1$, $R_2$, $R_3$, $L_1$, T and $L_2$ are as previously defined and $R_6$ represents hydrogen, with a compound of formula VIII

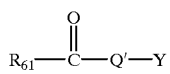

VIII in which $R_{61}$, Q' and Y are as previously defined, for example by heating the two compounds at a temperature in the range of 0–200° C. preferably in the range 15–150° C. optionally in the presence of an inert organic liquid which is preferably a solvent for the reactants e.g. an alcohol or acetonitrile, at atmospheric pressure optionally in the presence of a dehydrating agent, for example molecular sieves. It will be appreciated by those skilled in the art that it may be desirable to protect a nitrogen atom of the imidazole ring where Y represents a group of formula (2), (3) or (4) before this reaction, followed by removal of the protecting group after the reaction. An example of a suitable protecting group is benzyl.

Compounds of formula I may be prepared in a two-stage, one-pot process by reacting a compound of formula VII, in which $R_6$ represents hydrogen, with a compound of formula VIII, for example by heating the two compounds at a temperature in the range of 0–200° C., preferably in the range 15–150° C., optionally in the presence of an inert organic liquid which is preferably a solvent for the reactants e.g. an alcohol or acetonitrile, optionally in the presence of a dehydrating agent, for example molecular sieves, and then reducing the intermediate obtained directly by reaction with a reducing agent, for example sodium borohydride, in the presence of an inert organic liquid which is preferably a solvent for the reactants, for example an alcohol, at a temperature in the range 0–150° C., at atmospheric pressure.

Compounds of formula I may be prepared in a one stage process by reacting a compound of formula VII, in which $R_6$ represents hydrogen, with a compound of formula VIII in the presence of a reducing agent, for example sodium cyanoborohydride, in the presence of an inert organic liquid which is preferably a solvent for the reactants, for example an alcohol, at a temperature in the range 0–150° C., at atmospheric pressure.

Compounds of formula I may be prepared by reacting a compound of formula IX

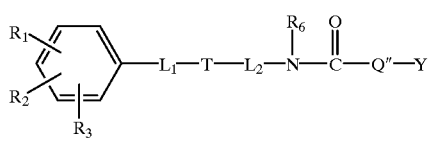

IX in which $R_1$, $R_2$, $R_3$, $L_1$, T, $L_2$, $R_6$ and Y are as previously defined and $-C(O)-Q''-$ represents a group which on reduction gives Q, with a reducing agent for example borane or lithium aluminium hydride, optionally in the presence of an inert organic liquid which is preferably a solvent for the compound of formula IX, for example an ether, at a temperature in the range 0–200° C., preferably 15–150° C., at atmospheric pressure.

Compounds of formula I may be prepared by reacting a compound of formula X

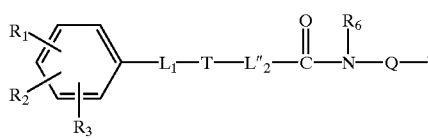

X in which $R_1$, $R_2$, $R_3$, $L_1$, T, $R_6$ Q and Y are as previously defined and $-L_2''-CO-$ represents a group which on reduction gives $L_2$, with a reducing agent, for example borane or lithium aluminium hydride, optionally in the presence of an inert organic liquid which is preferably a solvent for the compound of formula X, for example an ether, at a temperature in the range 0–200° C., preferably 15–150° C. at atmospheric pressure.

Compounds of formula I may be prepared by reacting a compound of formula XI

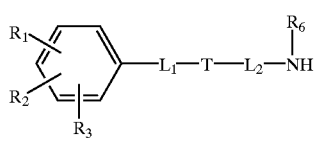

XI in which $R_1$, $R_2$, $R_3$, $L_1$, T, $L_2$ and $R_6$ are as previously defined with a compound of formula XII

Z-Q-Y        XII in which Z represents a leaving group for example chloro or bromo, optionally in the presence of a base, e. g.

triethylamine, in the presence of an inert organic liquid which is preferably a solvent for the reactants, at a temperature in the range 0–200° C.

Compounds of formula I in which $R_6$ represents hydrogen may be prepared by deprotecting compounds of formula XIII

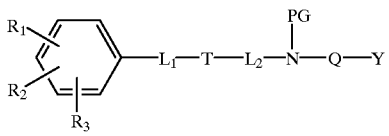

XIII in which $R_1$, $R_2$, $R_3$, $L_1$, T, $L_2$, Q and Y are as previously defined and PG represents an amine protecting group. Examples of suitable protecting groups for amines and methods for their addition and removal may be found in the textbook "protective Groups in Organic Synthesis" by T. W. Greene, John Wiley and Sons, 1981, e.g. formyl or acetyl.

Compounds of formula I in which Q represents a group of formula -$CH_2$-CH(OH)-$CH_2$- and Y represents a group of formula (1) may be prepared by reacting a compound of formula XVII
in which $R_1$, R $R_3$, $L_1$, T, $L_2$ and $R_6$ are as previously defined, with a compound of formula XXVII

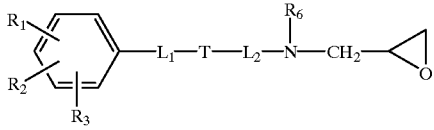

XVII in which $R_1$, $R_2$, $R_3$, $L_1$, T, $L_2$ and $R_6$ are as previously defined, with a compound of formula XXVII

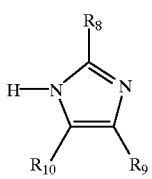

XXVII in which $R_8$, $R_9$ and $R_{10}$ are as previously defined at a temperature in the range 0–250° C., preferably in the range 50–150° C., optionally in the presence of an organic liquid, preferably a solvent for the reactants, for example tetrahydrofuran, N,N-dimethylformamide or an alcohol, optionally in the presence of a base, for example sodium hydride, at atmospheric pressure.

Compounds of formula I in which $L_1$ is other than a bond and T represents oxygen may be prepared by reacting a compound of formula XXXI

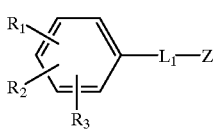

XXXI in which Z is a leaving group, for example chloro or bromo, with a compound of formula XXXII

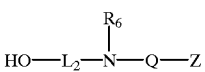

XXXII for example at a temperature in the range −50 to 250° C. preferably in the range 50–150° C., preferably in the presence of a base, for example sodium hydride, preferably in the presence of an inert organic liquid which is preferably a solvent for XXXI and XXXII, for example dimethylacetamide.

Compounds of formula I in which T represents a carbonyl group may be prepared by condensing a compound of formula XXXIII

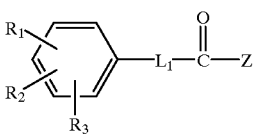

XXXIII in which Z represents a leaving group for example bromo, chloro, alkoxy, hydroxy with a compound of formula XXXII

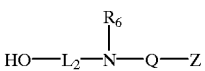

XXXII in which $L_2$, $R_6$, Q and Y are as defined previously, for example at a temperature in the range −50 to 250° C., preferably in the range −10 to 150° C., preferably in the presence of a base, for example triethylamine, and preferably in the presence of an inert organic liquid which is preferably a solvent for XXXII and XXXIII e.g. dichloromethane.

Compounds of formula I in which $R_6$ is a group other than hydrogen may be prepared by alkylation of a corresponding compound of formula I in which $R_6$ is hydrogen, for example using reductive alkylation for example using an aldehyde or a ketone in the presence of a reducing agent for example sodium borohydride.

Compounds of formula I in which $R_1$, $R_2$, $R_3$, $R_6$, $R_8$, $R_9$ or $R_{10}$ represents a hydroxyalkyl group may be prepared by reducing a compound of formula I in which $R_1$, $R_2$, $R_3$, $R_6$, $R_8$, $R_9$ or $R_{10}$, respectively, represents an alkoxycarbonyl group or an alkoxycarbonylalkyl group by methods known to those skilled in the art, for example using borane or lithium aluminium hydride.

Certain compounds of formula I may be converted into other compounds of formula I by functional group modifications known to those skilled in the art. For example hydroxy groups may be esterified to give carboxylic acid esters or sulphonic acid esters, amines may be acylated or sulphonylated or reacted with isocyanates to give ureas and certain functional groups may be oxidised or reduced e.g. alcohols may be oxidised to ketones; and esters, aldehydes and ketones may be reduced to alcohols.

Compounds of formula I in which one of the substituents $R_1$, $R_2$, $R_3$, $R_9$ or $R_{10}$ represents an aminoalkyl group may be prepared by reacting a compound of formula I in which the corresponding substituent is a cyanoalkyl group of appropriate length with a reducing agent for example lithium aluminium hydride or borane, in the presence of an organic liquid which is preferably a solvent for the starting material, e.g. tetrahydrofuran, at a temperature in the range 0–250° C.

Compounds of formula I in which $R_1$, $R_2$, $R_3$, $R_9$ or $R_{10}$ represents an aminoalkyl group may also be prepared by reacting a compound of formulae IX or X in which the corresponding substituent represents a cyanoalkyl group with a reducing agent, for example borane, in the presence of an organic liquid which is preferably a solvent for the starting material, e.g. tetrahydrofuran, at a temperature in the range 0–250° C.

It will be appreciated by those skilled in the art that compounds of formula I may be prepared by deprotecting compounds which are similar to compounds of formula I but have one or more substituents in a protected form. Methods of protecting and deprotecting functional groups are known to those skilled in the art and a reference is given earlier. Three examples are now given.

Compounds of formula I in which Y represents a group of formula (2) in which $R_{19}$ represents hydrogen may be prepared by deprotecting a compound of formula I in which Y represents a group of formula 2a

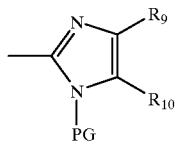

2a in which PG represents a protecting group for example when PG represents benzyl it may be removed by hydrogenation, for example by transfer hydrogenation using a proton source e.g. ammonium formate, a hydrogenation catalyst e.g. palladium on charcoal and an inert organic liquid which is preferably a solvent for the starting material, e.g. an alcohol e.g. ethanol, at a temperature in the range 0–250° C.

Compounds of formula I in which $R_1$, $R_2$ or $R_3$ represents a $C_{1-12}$ alkyl group substituted by a hydroxy group may be prepared by deprotecting a compound of formula I (for example by ether cleavage) in which $R_1$, $R_2$ or $R_3$ represents a $C_{1-12}$ alkyl group in which the hydroxyl group is protected, for example as a silyl ether.

Compounds or formula I in which $R_1$, $R_2$ or $R_3$ represents an ester may be prepared by deprotecting compounds of formula I in which $R_1$, $R_2$ or $R_3$ represents an ester protecting group, for example where the protecting group is 4,4-dimethyl-2-oxazolin-2-yl by reacting with the alcohol moiety of the desired ester in the presence of an acid e.g. sulphuric acid, and water.

Compounds of formula IV are commercially available or may be prepared by methods known to those skilled in the art, for example, those described in Comprehensive Organic Chemistry, Vol.1, (Edited by J. F. Stoddart) Published by Pergammon Press, 1979.

Compounds of formula V may be prepared by hydrolysis of a compound of formula XIV,

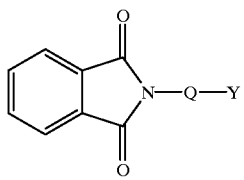

XIV for example in the presence of aqueous hydrochloric acid, or by reacting a compound of formula XIV with hydrazine.

Compounds of formula VII are commercially available or may be prepared by methods known to those skilled in the art, for example, those described in Comprehensive Organic Chemistry, Vol.2, (Edited by I. O. Sutherland) Published by Pergammon Press, 1979. Preferably compounds of formula VII, in which $R_6$ represents hydrogen, may be prepared by rearranging an amide of formula XXV

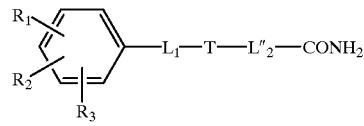

XXV in which $L_2''$-$CONH_2$ represents a group which on rearrangement gives $L_2NH_2$, for example by Hofmann rearrangement.

Compounds of formula VII, in which $R_6$ represents hydrogen, may be prepared by reacting compounds of formula XXVI

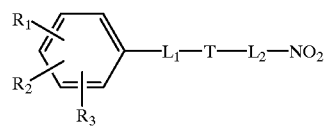

XXVI with a reducing agent, for example hydrogen in the presence of a catalyst or iron in the presence of an acid.

Compounds of formula VII in which $R_6$ is hydrogen and in which $L_2$ has two alkyl groups on the carbon adjacent to the nitrogen may be prepared by reacting a compound of formula XXXIV

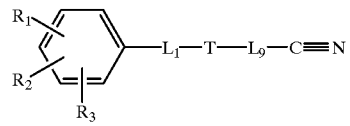

XXXIV in which $R_1$, $R_2$, $R_3$, $L_1$ and T are as previously defined and (-$L_9$-C=N) represents a group which gives -$L_2$-$NHR_6$ (as defined immediately above) after the reaction, with an alkyllithium reagent in the presence of a cerium (III) salt, for example cerium (III) chloride, at a temperature in the range −100 to 30° C., following the procedure described. in J. Org. Chem. 1992, 57, 4521–4527.

Compounds of formula VIII may be prepared by deprotecting a compound of formula XXIX

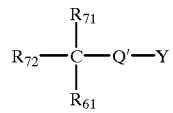

XXIX in which -$CR_{71}R_{72}$- represents a protected carbonyl group, as known to those skilled in the art, for example -$C(OC_2H_5)_2$-, by methods known to those skilled in the art, for example by hydrolysis. Compounds of formula VIII in which Y represents a group of formula (3) or (4) may be prepared by the method described in J. Med. Chem. 1981, Vol.24, p1139.

Compounds of formula IX in which Y represents an imidazole of formula (1) may be prepared by reacting a compound of formula XV

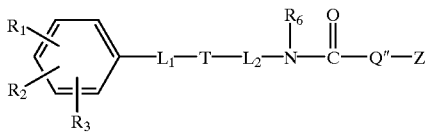

XV in which Z represents a leaving group, for example, halo, preferably bromo or chloro, with a compound of formula XXVII

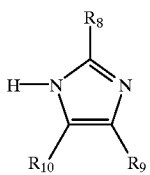

XXVII or an alkali metal salt thereof for example by heating, preferably in the presence of a solvent.

Compounds of formula IX in which Q" represents -(CH$_2$)$_2$- may be prepared by the reaction of a compound of formula XVI

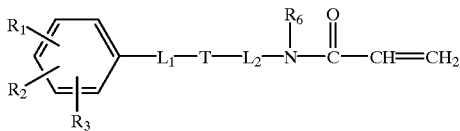

XVI with a compound of formula XXVII in the presence of a catalyst (e.g. N-benzyltrimethylammonium hydroxide) and optionally in the presence of an organic liquid which is preferably a solvent for the starting materials for example pyridine or 1,4-dioxane, at a temperature in the range 50–200° C., preferably 80–150° C.

Compounds of formula IX may be prepared by reacting a compound of formula VII with a compound of formula X.CO.Q".Y, in which X represents a leaving group for example chloro, optionally in the presence of a base, for example triethylamine. Compounds of formula X.CO.Q".Y may be prepared by methods known to those skilled in the art.

Compounds of formula X may be prepared by reacting compounds of formula XVIII

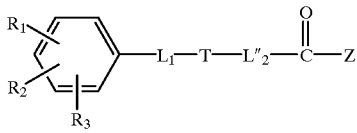

XVIII wherein Z is a leaving group, for example halo or hydroxy, preferably chloro, with a compound of formula R$_6$-NH-Q-Y which may be prepared from compounds of formula V by methods known to those skilled in the art.

Compounds of formula XI and XII may be prepared by methods known to those skilled in the art.

Compounds of formula XIII in which Y represents a group of formula (1) may be prepared by reacting a compound of formula XIX

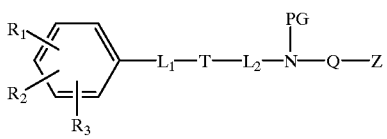

XIX in which Z represents a leaving group (for example halo) with a compound of formula XXVII or a salt thereof, for example by heating.

Compounds of formula XIII in which Y represents a group of formula (1) may be prepared by reacting a compound of formula XX

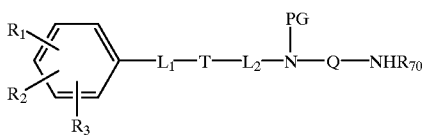

XX in which R$_{70}$ represents hydrogen or formyl with an —>idazole-forming synthon, for example as described in Advances in Heterocyclic Chemistry, Vol.12, 103 (1970) published by Academic Press.

Compounds of formula XIII may be prepared by reacting a compound of formula XXIII

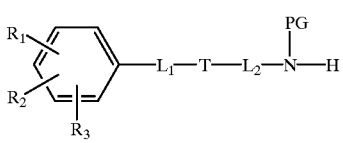

XXIII with a compound of formula X-Q-Y in which X represents a leaving group for example halo. Compounds of formula XIII may be prepared by reacting a compound of formula XXIII with a compound of formula X-CO-Q'-Y, in which -CO-Q'- represents a group which on reduction gives Q, followed by reduction. Compounds of formula X-Q-Y and X-CO-Q'-Y may be prepared by methods known to those skilled in the art.

Compounds of formula XIV may be prepared by reacting a compound of formula XXI

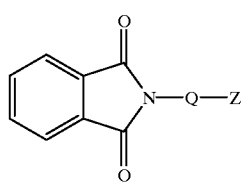

XXI in which Z is a leaving group for example halo, preferably chloro or bromo with a compound of formula XXVII or a salt thereof.

Compounds of formula XV may be prepared by reacting a compound of formula VII with an acyl halide of formula X.CO.Q".Z in which Z is a leaving group for example halo, preferably chloro, and X represents a leaving group, for example halo, in the presence of a base, for example triethylamine.

Compounds of formula XVI may be prepared by reacting a compound of formula VII with a compound of formula

XXII

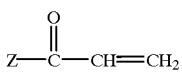

XXX

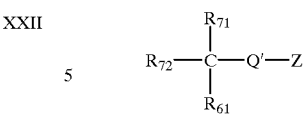

wherein Z is a leaving group for example halo, preferably chloro.

Compounds of formula XVII may be prepared from compounds of formula VII by methods analogous to those described in Tetrahedron, 1967, 2123.

Compounds of formula XIX may be prepared by reacting a compound of formula XXIII with a compound of formula X-Q-Z in which X represents a leaving group and Z represents a leaving group with the proviso that X is more labile than Z. Compounds of formula X-Q-Z may be prepared by methods known to those skilled in the art.

Compounds of formula XIX may be prepared by reacting a compound of formula XXIII with a compound of formula X-CO-Q'-Z followed by reduction. Compounds of formula X-CO-Q'-Z in which X and Z represent leaving groups for example halo may be prepared by methods known to those skilled in the art.

Compounds of formula XX in which $R_{70}$ represents formyl may be prepared from compounds of formula XX in which $R_{70}$ represents hydrogen by methods known to those skilled in the art.

Compounds of formula XX in which $R_{70}$ represents hydrogen may be prepared by hydrolysis of compounds of formula XXIV

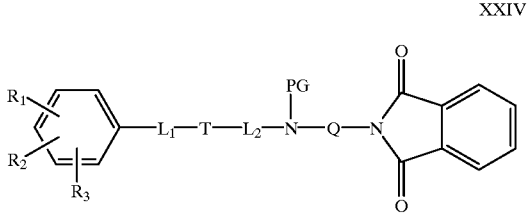

by methods known to those skilled in the art.

Compounds of formula XXIII may be prepared from compounds of formula VII in which $R_6$ represents hydrogen by methods known to those skilled in the art.

Compounds of formula XXIV may be prepared by reacting a compound of formula XXIII with a compound of formula XXI by methods known to those skilled in the art.

Compounds of formula XXV may be prepared by hydrolysing compounds of formula XXVIII

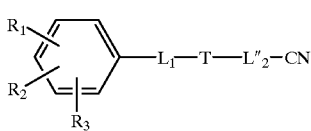

for example using a) an acid, or b) a base optionally in the presence of an oxidising agent e.g. hydrogen peroxide.

Compounds of formula XXIX may be prepared by methods known to those skilled in the art, for example when Y represents a group of formula 1) by reacting a compound of formula XXVII with a compound of formula XXX in which $R_{61}$, $R_{71}$ and $R_{72}$ are as described previously, and Z represents a leaving group, for example halo.

Compounds of formulae XXVII, XVIII, XXI, XXII, XXVI, XXVIII, XXX, XXXI, XXXII and XXXIII are commercially available or may be prepared by methods known to those skilled in the art.

Certain compounds of formulae IV, V, VI, VII, and VIII are known but it will be apparent to those skilled in the art that the novel compounds may be prepared in a similar manner to the preparation of known compounds of said formulae.

Certain of the intermediate compounds of formulae III–XXVII are believed to be novel compounds. All novel compounds herein are claimed as a further aspect of the invention.

Compounds of formulae II, IIa, IIb, IIc and IId may be prepared in a similar manner to compounds of formula I.

It will be appreciated by those skilled in the art that in cases where a substituent is identical with, or similar to, a functional group which has been modified in one of the above processes that these substituents will require protection before the process is undertaken, followed by deprotection after the process. Otherwise competing side-reactions will occur. Alternatively, another of the processes described above, in which the substituent does not interfere, may be used.

The compounds of formula I are antiinflammatory agents and may show therapeutic activity at a dose of 200 mg/kg or lower in standard laboratory animals. The therapeutic activity of compounds of formula I has been demonstrated by one or both of the following tests A and B.

Test A was carried out in the following way:
Inhibition of Arachidonic Acid Release from Zymosan Stimulated Macrophages Female MF1 mice (weighing 20 to 25 g) were killed using a rising concentration of $CO_2$. The mice were laid on their backs and the abdomens wiped with 70% alcohol. The skin was pulled back, exposing the peritoneal wall. Medium A (5 ml) (see below) was injected into the peritoneal cavity of each mouse followed by approximately 1 ml of air using a 20 ml syringe and a 21G×40 mm needle in order to form a suspension of macrophage cells. The medium and cells were then removed using a 19G×40 mm needle. The resulting suspension was returned to a sterile beaker kept on ice. The extracts from all the mice were pooled and this pooled cell suspension was counted using a Coulter counter and adjusted to a final cell count of $1-1.3\times10^6$ cells/ml prior to labelling with [$^3$H]-arachidonic acid. Typically five mice provided sufficient cells for each multiwell plate.

Sufficient [$^3$H]-arachidonic acid in ethanol to give a final concentration of 1.6 μCi/ml (equivalent to 40 LCi/plate) was blown to dryness under nitrogen. The arachidonic acid was then resuspended in 1 or 2 ml of the cell suspension which was then mixed with the remainder of the cell suspension in a centrifuge bottle. The labelled cell suspension was then plated out into sterile plastic 96 flat-bottomed well plates (250 μl per well) and incubated overnight at 37° C. in a moist atmosphere of 5% $CO_2$, 95% air.

The following day, non-adherent cells were removed by washing 3 times with sterile phosphate buffered saline (PBS). The adherent peritoneal macrophages were then cultured for a further 24 hours in the presence or absence of drugs, in medium B (see below) at 370 in a 5% $CO_2$ atmosphere in order to measure the effects of drugs on the spontaneous release of arachidonic acid in the absence of stimulus. After this incubation, supernatants were removed to give media I and stored in sealed multi-well plates at 4° C. prior to scintillation counting. Drugs which potentiated spontaneous release of arachidonic acid (125% of controls) were deemed to be toxic at the concentration at which this phenomenon occurred. The supernatants were replaced by fresh medium C containing fresh drug and a stimulus. Three drugs were tested at six concentrations (100, 50, 20, 10, 5 and 1 $\mu$M) in replicates of four on each plate. The other wells contained controls consisting of a positive control (e.g. dexamethasone), medium (B) only and medium C only.

Incubation was then continued for a further 5 hours, whereupon the supernatants were collected to give media 2 and the adherent cells washed with PBS. The cells were then lysed with 100 $\mu$l of 0.1% TRITON® X100 in a 0.1% solution of bovine serum albumin in 0.9% saline and mechanically disrupted to give cell lysates.

These supernatants (media 2) and cell lysates (Cells) were also stored in sealed multi-well plates at 4° C. prior to scintillation counting. 200 $\mu$l aliquots of media, or 100 $\mu$l aliquots of cells were counted using 2 ml of OPTIPHASE "HIGH SAFE" (Trademark of LKB) as scintillant.

Calculation of results

The percentage of arachidonic acid released was calculated using the mean values for each group of 4 wells in the following equation.

$$\% \text{ Release} = \frac{\text{cpm in media 2}}{\text{cpm in media 2} + \text{cpm in cell lysate}} \times 100$$

cpm = counts per minute

The value for the arachidonic acid release in the absence of stimulus (spontaneous, cpm of media 2) from cells which had been exposed to neither stimulus nor drug was subtracted from all equivalent values (cpm media 2, stimulated with or without drug) to give the net stimulated release. The percentage inhibition of arachidonic acid release caused by a drug may then be calculated using the following equation.

$$\% \text{ Inhibition} = 100 - \frac{\text{net stimulated release in presence of drug} \times 100}{\text{net stimulated release in absence of drug}}$$

Compounds of formula I were tested at six concentrations (100, 50, 20, 10, 5 and 1 $\mu$M) and $IC_{50}$ values calculated. Compounds with $IC_{50}$ values $\leq 100$ $\mu$M are considered to be active. Advantageous compounds have an $IC_{50}$ value $<50$ $\mu$M.

Medium A (for peritoneal lavage)

To a sterile 100 ml measuring cylinder was added:—40 ml TC199 with Earle's salts (tenfold concentrate) (ICN); 4 ml heat inactivated swine serum (ICN); 10 ml sodium bicarbonate (7.5% in sterile water); 0.4 ml antibiotics solution (60 mg/ml benzylpenicillin+100 mg/ml streptomycin) and 0.72 ml heparin (5000 U/ml). This mixture was transferred to sterile flask and made up to 400 ml with sterile water.

Medium B (for cell culture)

To a sterile 250 ml measuring cylinder was added:—65 ml TC 199 (tenfold concentrate) with Earle's salts (ICN); 6.5 ml heat inactivated swine serum; 16.25 ml sodium bicarbonate (7.5% in sterile water); 0.65 ml antibiotics solution as above and 65 mg glutamine. This mixture was transferred to a sterile beaker and made up to 650 ml with sterile water.

Medium C=medium B+stimulant (zymosan)

The zymosan stimulant was prepared as follows:—zymosan (200 mg) (supplied by Sigma) was added to PBS (20 ml). The mixture was boiled for 30 minutes and the volume restored to 20 ml with water. The zymosan was harvested by centrifugation at 500×g for 5 minutes, washed twice by resuspension in PBS (10 ml) and centrifugation. After the final separation, the zymosan was resuspended in 20 ml PBS and stored as 1 ml aliquots at −20° C.

650 ml medium B containing 15 ml zymosan=12.5 particles per cell was made up and then stored in 3 ml aliquots in a freezer.

Test B was carried out in the following way:

Carrageenan-induced rat paw oedema test

Female rats, weight range 125–150 g were fasted overnight. One of the hind legs of each animal was marked with a line at the connection between the cuboid/navicular and calcaneus/talus bones. Groups of six rats were orally dosed at 10 ml/kg, in random order, with a given dose of the test compound given as a solution or suspension in 10% (w/v) aqueous acacia solution.

One hour after dosing, 0.1 ml of 1% (w/v) sterile carrageenan $\lambda$ in normal saline was injected deeply into the plantar surface of the marked hind foot of each rat. The volume of the foot (up to the marked line) was measured immediately after injection using duplicate water displacement readings. Three hours after injection the foot volume was measured again and the percentage increase in foot volume relative to the initial reading was calculated.

The increase in foot volume (i.e. the degree of oedema) in drug treated animals when compared with that in the drug untreated control gave the degree of inhibition of paw oedema by the drug.

Compounds were considered to be active in this test if they produced a 20% or greater inhibition of paw oedema in at least two out of three tests after oral dosing at 100 mg/kg. Statistical significance was assessed using the Student's t test for single dose studies and Dunnett's test for multiple dose studies. More advantageous compounds were active in both Tests A and B.

| Final product of Example | Test A $IC_{50}$ $\mu$M |
| --- | --- |
| 1 | 20 |
| 2 | 26 |
| 3 | 30 |
| 4 | 29 |
| 5 | 17 |
| 6 | 20 |
| 7 | 39 |
| 8 | 14 |
| 9 | 50 |
| 10 | 36 |
| 11 | 37 |
| 12 | 7 |
| 13 | 9 |
| 14 | 6 |
| 15 | 27 |
| 16 | 7 |
| 17 | 12 |
| 18 | 20 |
| 19 | 8 |
| 20 | 4 |
| 21 | 8 |
| 22 | 26 |
| 23 | 7 |
| 24 | 22 |
| 25 | 11 |
| 26 | 10 |
| 27 | 70 |
| 28 | 25 |
| 29 | 15 |
| 30 | 20 |
| 31 | 74 |
| 32 | 9 |
| 33 | 32 |

| Final product of Example | Test A IC$_{50}$ $\mu$M |
|---|---|
| 34 | 76 |
| 35 | 47 |
| 36 | 60 |
| 37 | 49 |
| 38 | |
| 39 | 0.2 |
| 40 | 0.3 |
| 41 | 10 |
| 42 | 9 |
| 43 | 92 |
| 44 | 120 |
| 45 | 170 |
| 46 | 80 |
| 47 | 64 |
| 48 | 70 |
| 49 | 70 |
| 50 | 49 |
| 51 | 87 |
| 52 | 23 |
| 53 | 99 |
| 54 | 7 |
| 55 | 7 |
| 56 | 8 |
| 57 | 21 |
| 58 | 20 |
| 59 | 8 |
| 60 | 17 |
| 61 | 9 |
| 62 | 14 |
| 63 | 14 |
| 64 | 32 |
| 65 | 88 |
| 66 | 24 |
| 67 | 20 |
| 68 | 100 |
| 69 | 50 |
| 70 | 84 |
| 71 | 23 |
| 72 | 24 |
| 73 | 25 |
| 74 | 82 |
| 75 | 26 |
| 76 | 16 |
| 77 | 12 |
| 78 | 92 |
| 79 | 20 |
| 80 | 13 |
| 81 | 65 |
| 82 | 17 |
| 83 | 90 |
| 84 | 15 |
| 85 | 47 |
| 86 | 3 |
| 87 | 25 |
| 88 | 28 |
| 108 | 100 |
| 109 | 33 |

In Test B the final products of Examples 2, 3, 4, 7, 8, 15, 64 and 88 were active at a dose of 100 mg/kg.

The most advantageous compounds of formula I were active in Tests A and B and also in the following test. Carrageenon-induced pleurisy in rats was carried out as described by Ackerman et al. J. Pharmacol. Exp. Therap. 180, 215, 588–595. Migrating leukocytes were harvested by lavage of the thoracic cavity 72 h after injection of 0.3 ml 1% λ.carrageenan in sterile isotonic saline. Test compounds were administered p.o. at the time of challenge and 24 h and 48 h thereafter.

In this test the final products of Examples 1, 2, 15, 16, 17, 29, 56, 64, 85 and 88 were active at 10 mg/kg and the final products of Examples 43 and 60 were active at 3 mg/kg or lower.

Especially advantageous compounds of formula I were active in the tests above and also in the late phase of the following test. Early and late phase bronchoconstriction in guinea-pigs following antigen challenge was determined by a variation of the method described by Hutson et al. Am. Rev. Respir. Dis. 1988, 137, 548–557. Guinea-pigs were sensitised by a single i.p. injection of 10 $\mu$g ovalbumin and challenged 15 to 17 days later by exposure to aerosolized antigen (4%) for five minutes, following pretreatment with mepyramine to prevent anaphylaxis. Changes in lung function were determined by whole body plethysmography at various times after challenge. Test compounds were administered p.o. 24 h and 2 h prior to challenge.

The therapeutic activity of the preferred compounds of the present invention has also been demonstrated by an in vitro mixed lymphocyte reaction which is an in vitro correlate of in vivo cellular immune reactivity. A mixed lymphocyte reaction (MLR) occurs when lymphocytes from two genetically dissimilar individuals, or inbred strains of mice are cultured together. An MLR results in the activation and proliferation of lymphocytes, which is measured by the incorporation of radiolabelled thymidine into the cellular DNA synthesised during cell division. A 'one-way' MLR is used to determine the immunosuppressive activity of test compounds in vitro. In this reaction one population of spleen cells serves as the stimulator cells and is treated with mitomycin C to prevent cell division. Spleen cells from a second allogeneic population (responder cells) are untreated and when mixed with the stimulator cells are able to undergo division which is measured. The degree of proliferation is measured in the presence and absence of test compound to assess the immunosuppressive activity of the compound.

The techniques for carrying out lymphocyte proliferation assays including MLRs are well known, eg Bradley, pages 156–166, in Mishell and Shiigi, Eds. Selected Methods in Cellular Immunology (Freeman, San Francisco, 1980); and Battisto et al, methods in Enzymology 1987; 150: 83–91. Various slight modifications of these techniques are in use and that used herein is described in Gibb, Webber and Bowen, J Immunological Methods 1985; 81: 107–113. The immunomodulant activity of the preferred compounds was determined in a mixed lymphocyte reaction (Test C) in the following manner:

Mixed Lymphocyte Reaction

Cell suspensions obtained from the spleens of female BALB/c and C57BL/6 strain mice of between 6 and 9 weeks of age were used as sources of responder and stimulator cells respectively. The mice were killed using a rising concentration of $CO_2$ and the spleens removed aseptically and teased using a scalpel and forceps to produce a single cell suspension in Hanks balanced salt solution (HBSS). The suspensions were filtered through cell strainers (Falcon), sedimented by centrifugation and resuspended in Tris-buffered ammonium chloride pH 7.2 (medium D) to lyse the erythrocytes. The cells were sedimented again and washed twice in HBSS before resuspending in complete RPMI 1640 tissue culture medium (medium E). The C57BL/6 cells were resuspended to 9 mls per spleen and a solution of mitomycin C at 400 $\mu$g/ml in medium E added to give a final concentration of 40 $\mu$g/ml. After incubation of the C57BL/6 cells at 37° C. for 30 minutes in an atmosphere of 5% $CO_2$ and 95% air, the cells were sedimented and washed 3 times in medium E. Both cell suspensions were diluted in medium E to 5×10$^6$ cells/ml. 100 $\mu$l of each of the responder and stimulator cell suspensions were aliquoted into the wells of 96 well flat bottom microtitre plates containing 50 $\mu$l of test compound at an appropriate dilution (initially 50 $\mu$M diluted in medium E from a stock solution at 100 mM in dimethyl sulphoxide) giving a final test compound concentration of 10 $\mu$M (final dilution) Compounds active at this concentration were tested at further final dilution of 1 $\mu$M, 0.1 $\mu$M and 0.01 $\mu$M to determine the concentration of test compound which causes 50% inhibition of the immune response (IC50). After four days of culture at 37° C. in a humidified atmosphere of 5% $CO_2$ and 95% air, 1 μCi of tritiated thymidine in 20 μl of medium E was added to each well and the plates incubated for a further 24 hours. Cells were then harvested onto Inotech G7 glass fibre filter mats using an Inotech cell harvester. The filters were transferred to vials to which 2 mls of Packard Emulsifier-Safe scintillation fluid was added and the radioactivity from the incorporated thymidine was counted in a Packard liquid scintillation counter.

The counts per minute (CPM) reflect the degree of lymphocyte proliferation. The data were analysed to determine the percentage inhibition of lymphocyte proliferation by the test compound. Compounds were deemed active if they reproducibly inhibited proliferation by >50% in the absence of toxicity at a concentration of <10 μM.

Medium D (for erythrocyte lysis)
Stock solutions
0.17M Tris. Tris base (20.6 g) was dissolved in distilled water (900 ml) and the pH adjusted to 7.65 with dilute hydrochloric acid. The volume was made up to 1000 ml with distilled water.
90.16M Ammonium chloride: Ammonium chloride (8.3 g) was dissolved in distilled water (1000 ml).
Working solutions
The Tris stock solution (10 ml) and ammonium chloride stock solution (90 ml) were mixed, the pH adjusted to 7.2 with dilute hydrochloric acid and the solution filter sterilised.
Medium E (for cell culture)
RPMI 1640 tissue culture medium containing 2.0 g/l sodium bicarbonate (ICN FLOW) supplemented with 5–10% serum supplement (foetal calf serum, Sigma or Nu-Serum, Collaborative Biomedical Products) 2 mM L-glutamine (ICN FLOW), 50 IU/ml penicillin (ICN FLOW), 50 μg/ml streptomycin (ICN FLOW) and $5\times10^5$M 2-mercaptoethanol (SIGMA).

MLR data were expressed as the percentage inhibition of lymphocyte proliferation caused by the test compound, calculated by the formula $$\% \text{ inhibition} = 100 - \frac{\text{test} \times 100}{\text{control}}$$

where:
control=CPM thymidine incorporation by responder cells mixed with stimulator cells in the absence of compound
test=CPM thymidine incorporation by responder cells mixed with stimulator cells in the presence of test compound.

The final products of the Examples listed below were active at a final concentration of 10 μM in at least two out of three tests. The final concentration of test compound which causes 50% inhibition of the immune response ($IC_{50}$ μM) for each compound is given below.

| Example | 8 | 16 | 17 | 19 | 87 |
|---|---|---|---|---|---|
| $IC_{50}$ | 2.4 | 2.8 | 5.9 | 1.7 | 5.8 |

The invention is illustrated by the following non-limitative Examples in which compositions of mixed solvents are given by volume. Novel compounds were characterised by one or more of the following: elemental analysis, nuclear magnetic resonance (nmr), infra-red and mass spectroscopy. Temperatures are given in degrees Celsius. The abbreviations HPLC (high performance liquid chromatography), THF (tetrahydrofuran), DMF (dimethylformamide), ATEt (Amount), Vol (Volume), Temp (Temperature), Ex (Example), IMS (industrial methylated spirit), c (concentration in grams of sample per 100 ml of solution), s (singlet), d (doublet), t (triplet), br (broad) and m (multiplet) have been used in the Examples.

EXAMPLE 1 a) A mixture of 2-(4-chlorophenoxy)-2-methylpropionic acid (15.0 g) and thionyl chloride (70 ml) was boiled under reflux for 1 hour. The thionyl chloride was distilled off and the residue distilled under vacuum to give 2-(4-chlorophenoxy) -2-methylpropionyl chloride, b.p. 84–87° C. at 0.07 mbar. A solution of this chloride (14.17 g) in dichloromethane (50 ml) was added dropwise to a mixture of 1-(3-aminopropyl)imidazole (7.63 g), triethylamine (6.78 g) and dichloromethane (100 ml) at below 0° C. with stirring. After the addition, the mixture was allowed to warm up to ambient temperature and stirred at this temperature for 2 hours. Saturated aqueous sodium bicarbonate solution (100 ml) was added and the mixture stirred for 1 hour. The mixture was separated and the aqueous layer was washed with dichloromethane. The combined organic layers were dried and evaporated to give a solid which was recrystallised from ethyl acetate to give 2-(4-chlorophenoxy)-N-[3-(imidazol-1-yl)propyl ]-2-methylpropionamide, m.p. 83–84° C.

b) A mixture of the amide from a) (8.04 g), dry THF (175 ml) and borane/THF (103.5 ml, 1.0 M solution) was boiled under reflux for 2.5 hours. The solvent was removed by evaporation and the residue heated under nitrogen at 100° C. for 1 hour. Hydrochloric acid (1 M; 40 ml) was added and the mixture heated at 95° C. for a further 1.5 hours. The reaction mixture was basified with aqueous sodium hydroxide (5 M) and extracted with ethyl acetate to give an oil which was distilled to give 2-(4-chlorophenoxy)-3'-(imidazol-1-yl) -2-methyldipropylamine, b.p. 160–170° C. at 0.01 mbar.

EXAMPLES 2–14

In a similar manner to Example 1a, a compound of formula XVIII in which Z is chloro (prepared in a similar manner to Example 1a) was reacted with a compound of formula V, in which $R_6$ is hydrogen, Y represents an imidazole of formula (1) and Q is as shown in Table 1, to give compounds of formula X in which $R_6$ is hydrogen. The substituents on XVIII and V and the amount of each material used are shown in Table 1. Compounds of formula X, in which $R_6$ represents hydrogen and Y represents an imidazole of formula (1), were reduced to give compounds of formula I in a similar manner to Example 1b. The groups $R_1$, $R_2$, $R_3$, $-L_1-T-L_2$"- and Q and the amounts of the reactants are shown in Table 2.

The compounds of formula X in Examples 9a and 10a were prepared in a different manner as indicated and then reduced as in Example 1b.

TABLE 1

| Ex | XVIII R₁ R₂ R₃ | L₁-T-L₂" | Wt (g) | V Q | R₈ | R₉ | R₁₀ | Wt (g) | Et₃N (ml) | CH₂Cl₂ (ml) | Total Notes on Product |
|---|---|---|---|---|---|---|---|---|---|---|---|
| 2a | 4-Cl | OCH₂ | 12.5 | (CH₂)₃ | H | H | H | 7.6 | 9.3 | 150 | m.p.114–116° C. |
| 3a | H | OCH₂ | 11.9 | (CH₂)₃ | H | H | H | 8.7 | 9.8 | 175 | oil |
| 4a | 2-Cl | OC(CH₃)₂ | 10.0 | (CH₂)₃ | H | H | H | 5.9 | 7.0 | 130 | oil |
| 5a | 4-C₂H₅ | OCH₂ | 40.4 | (CH₂)₃ | H | H | H | 24.3 | 31.1 | 450 | oil |
| 6a | 3,4-(CH₃)₂ | OCH₂ | 4.8 | (CH₂)₃ | H | H | H | 3.3 | 4.0 | 45 | oil |
| 7a | 4-F | OCH₂ | 17.0 | (CH₂)₃ | H | H | H | 12.5 | 14.6 | 250 | oil |
| 8a | 4-Cl | OCH₂ | 5.1 | (CH₂)₃ | CH₃ | H | H | 3.5 | 3.8 | 60 | m.p.123–124° C. |
| 11a | 4-Cl | SCH₂ | 20.3 | (CH₂)₃ | H | H | H | 12.2 | 14.6 | 260 | oil |
| 12a | 4-Cl | CH₂CH₂ | 4.9 | (CH₂)₃ | CH₃ | H | H | 3.3 | 3.7 | 60 | m.p.104–106° C. |
| 13a | 4-Cl | C(CH₃)₂ | 16.6 | (CH₂)₃ | H | H | H | 9.6 | 11.7 | 188 | oil |
| 14a | 4-Cl | CH₂CH₂ | 4.9 | (CH₂)₃ | H | H | H | 3.0 | 3.7 | 40 | oil |

TABLE 2

| Ex | R₁ R₂ R₃ | L₁-T-L₂" | X Q | R₈ | R₉ | R₁₀ | Wt (g) | BH₃/THF Vol/ml | THF Vol/ml | Notes |
|---|---|---|---|---|---|---|---|---|---|---|
| 2b | 4-Cl | OCH₂ | (CH₂)₃ | H | H | H | 7.34 | 103.5 | 175 | |
| 3b | H | OCH₂ | (CH₂)₃ | H | H | H | 15.2 | 320 | 175 | |
| 4b | 2-Cl | OC(CH₃)₂ | (CH₂)₃ | H | H | H | 12.4 | 162 | 225 | |
| 5b | 4-C₂H₅ | OCH₂ | (CH₂)₃ | H | H | H | 11.5 | 162 | 275 | |
| 6b | 3,4-(CH₃)₂ | OCH₂ | (CH₂)₃ | H | H | H | 2.57 | 35 | 60 | |
| 7b | 4-F | OCH₂ | (CH₂)₃ | H | H | H | 9.70 | 142 | 300 | 1 |
| 8b | 4-Cl | OCH₂ | (CH₂)₃ | CH₃ | H | H | 4.0 | 54 | 140 | |
| 9b | 4-Cl | O(CH₂)₂ | (CH₂)₃ | H | H | H | 3.5 | 47 | 120 | |
| 10b | 4-PhCH₂O | OCH₂ | (CH₂)₃ | H | H | H | 10.0 | 110 | 300 | 1 |
| 11b | 4-Cl | SCH₂ | (CH₂)₃ | H | H | H | 23.1 | 300 | 250 | |
| 12b | 4-Cl | CH₂CH₂ | (CH₂)₃ | CH₃ | H | H | 4.6 | 60 | 104 | |
| 13b | 4-Cl | C(CH₃)₂ | (CH₂)₃ | H | H | H | 11.1 | 145 | 250 | |
| 14b | 4-Cl | CH₂CH₂ | (CH₂)₃ | H | H | H | 6.9 | 94 | 160 | |

1 The initial product was treated as described in Example 2c to give the hydrochloride salt.

The products obtained in Table 2 were as follows:

EXAMPLE 2b

N-[2-(4-Chlorophenoxy)ethyl]-3-(imidazol-1-yl)propylamine, b.p. 165–175° C. at 0.03 mbar.

EXAMPLE 2c

The product from Example 2b (3.8 g) was dissolved in ether (100 ml) and treated with ethereal hydrogen chloride to give a sticky white solid. The supernatant liquid was decanted off, and the solid triturated with fresh ether (150 ml). The mixture was left to stand overnight. The ether was decanted of f and the solid treated with propan-2-ol (150 ml). The mixture was boiled under reflux for 10 minutes and a small amount of insoluble material filtered off and discarded. The filtrate was cooled slowly to 0° C. whereupon a solid crystallised out. The solid was dried under vacuum at 50° C. to give N-[2-(4-chlorophenoxy)ethyl]-3-(imidazol-1-yl)propylamine hydrochloride, m.p. 172–174° C.

EXAMPLE 3b 3-(Imidazol-1-yl)-N-(2-phenoxyethyl)propylamine, b.p. 155–160° C. at 0.07 mbar.

EXAMPLE 4b 2-(2-Chlorophenoxy)-3'-(imidazol-1-yl)-2-methyldipropylamine, b.p. 165–175° C. at 0.07 mbar.

EXAMPLE 5b

N-[2-(4-Ethylphenoxy)ethyl]-3-(imidazol-1-yl)propylamine, b.p. 165–175° C. at 0.07 mbar.

EXAMPLE 6b

N-[2-(3,4-Dimethylphenoxy)ethyl]-3-(imidazol-1-yl)propylamine, b.p. 200° C. at 0.4 mbar.

EXAMPLE 7b

N-[2-(4-Fluorophenoxy)ethyl]-3-(imidazol-1-yl)propylamine dihydrochloride, m.p. 172–173° C.

EXAMPLE 8b

N-[2-(4-Chlorophenoxy)ethyl]-3-(2-methylimidazol-1-yl)propylamine, b.p. 165–175° C. at 0.07 mbar.

EXAMPLE 9b 3-(4-Chlorophenoxy)-3'-(imidazol-1-yl)dipropylamine, b.p. 180–185° C. at 0.13 mbar.

EXAMPLE 10b

N-[2-(4-Benzyloxyphenoxy)ethyl]-3-(imidazol-1-yl)propylamine dihydrochloride hydrate, m.p. 141–142.5° C.

EXAMPLE 11b

N-[2-(4-Chlorophenylthio)ethyl]-3-(imidazol-1-yl)propylamine, b.p. 170–175° C. at 0.03 mbar.

EXAMPLE 12b 3-(4-Chlorophenyl)-3'-(2-methylimidazol-1-yl) dipropylamine, b.p. 165° C. at 0.03 mbar.

EXAMPLE 13b 2-(4-Chlorophenyl)-3'-(imidazol-1-yl)-2-methyldipropylamine dihydrochloride, m.p. 200–201° C.

EXAMPLE 14b 3-(4-Chlorophenyl)-3'-(imidazol-1-yl)dipropylamine, b.p. 160–165° C. at 0.03 mbar.

EXAMPLE 9a

A solution of 3-(4-chlorophenoxy)propionic acid (5.0 g, prepared from 4-chlorophenol by the process described in J.A.C.S. 1923, 2708 for the conversion of phenol into 3-phenoxypropionic acid) in THF (90 ml) was treated with 1,1'-carbonyldiimidazole (4.05 g) at room temperature with stirring. The mixture was stirred at ambient temperature for two hours. 1-(3-Aminopropyl)imidazole (3.12 g) was added and the mixture was stirred at ambient temperature for 18 hours. The solvent was distilled off and the residue was dissolved in dichloromethane, washed with water, dried and then evaporated to give a solid which was recrystallised from ethyl acetate to give 3-(4-chlorophenoxy)-N-[3-(imidazol-1-yl)propyl]propionamide, m.p. 114–115.5° C.

EXAMPLE 10a 1,1'-Carbonyldiimidazole (16.2 g) was added to a stirred suspension of 4-benzyloxyphenoxyacetic acid (25.8 g) in dry THF (350 ml) and the mixture was stirred at ambient temperature for 2 hours. 1-(3-Aminopropyl)imidazole (12.5 g) was added and the mixture was stirred for a further 18 hours. The mixture was filtered and the filtrate evaporated to give a residue which was treated as in Example 9a to give 2-(4-benzyloxyphenoxy)-N-[3-(imidazol-1-yl)propyl] acetamide m.p. 112–113° C.

EXAMPLE 15 a) A mixture of DL-2-(4-chlorophenoxy)propionic acid (20.1 g) and thionyl chloride (130 ml) was boiled under reflux for 75 minutes. Excess thionyl chloride was distilled off and the residue was dried under high vacuum for 30 minutes. The resulting acid chloride was dissolved in dichloromethane (100 ml) and added drop-wise to a stirred solution of 1-(3-aminopropyl)imidazole (12.5 g) and triethylamine (11.1 g) in dichloromethane (200 ml) at 0C. The mixture was left to stand at ambient temperature for 18 hours. Saturated sodium bicarbonate solution (100 ml) was added and the mixture stirred for 30 minutes. The organic layer was separated, dried and evaporated. The residue was dissolved in ethyl acetate and extracted with 5 M hydrochloric acid. The combined acid extracts were basified and extracted with ethyl acetate. This organic extract was washed with water, dried and evaporated to give an oil which was purified by chromatography on silica using dichloromethane/methanol (9:1) as the mobile phase to give 2-(4-chlorophenoxy)-N-[3-(imidazol-1-yl)propyl] propionamide as an oil.

b) A solution of the amide from a) (6.10 g) in dry THF 185 ml) was added to a stirred suspension of lithium aluminium hydride (1.51 g) in THF (170 ml) under nitrogen. The mixture was boiled under reflux for 5 hours. On cooling, water (2.0 ml), 5M sodium hydroxide (2.0 ml) and water (6.0 ml) were added dropwise and the mixture stirred for 30 minutes. The mixture was filtered and filtrate evaporated to give an oil. The oil was dissolved in ethyl acetate, washed with water, dried and evaporated to give an oil which was converted into a hygroscopic hydrochloride. This was recrystallised from propan-2-ol, the solid obtained was dissolved in the minimum volume of hot absolute alcohol and precipitated with ether to give 2-(4-chlorophenoxy)-3'-(imidazol-1-yl)dipropylamine dihydrochloride, m.p. 195–197° C.

EXAMPLE 16 a) 1,1'-Carbonyldiimidazole (6.48 g) was added to a solution of 4-chlorophenoxyacetic acid (7.46 g) in THF (144 ml) at ambient temperature. The mixture was stirred for 2 hours and then 1-(5-aminopentyl)imidazole (6.1 g) was added. The mixture was stirred at ambient temperature for 18 hours and then worked up as described in Example 9a to give an oil which was purified by flash chromatography on silica using ethyl acetate/methanol/ triethylamine, 18:2:1 as the mobile phase to give 2-(4-chlorophenoxy)-N-[5-(imidazol-1-yl)pentyl]acetamide as an oil.

b) A mixture of the product from a) above (5.0 g), dry THF (108 ml) and borane/THF (64 ml, 1.0 M solution) was boiled under reflux for 2.5 hours. The mixture was worked up as described in Example 1b to give an oil which was not distilled but was dissolved in ether, filtered and the filtrate treated with ethereal hydrogen chloride to give a solid which was collected by filtration and then recrystallised from propan-2-ol to give N-[2-(4-chlorophenoxy)ethyl]-5-(imidazol-1-yl)pentylamine dihydrochloride hemihydrate, m.p. 124–126° C.

EXAMPLE 17 a) A mixture of N-[2-(4-chlorophenoxy)-1,1-dimethylethyl]acrylamide (4.5 g), imidazole (1.24 g), benzyltrimethylammonium hydroxide (0.62 ml of a 40% solution in methanol, Triton®B) and 1,4-dioxane (40 ml) was heated at 95° C. for 7 hours. The solvent was removed under reduced pressure and the residue was dissolved in dichloromethane. This solution was extracted with 5M hydrochloric acid. The combined acid extracts were basified with 10M sodium hydroxide solution and extracted with dichloromethane to give N-[2-(4-chlorophenoxy)-1,1-dimethylethyl]-3-(imidazol-1-yl)propionamide.

b) A mixture of the propionamide from a) (5.26 g), dry THF (110 ml) and borane/THF (67 ml, 1.0 M solution) was boiled under reflux for 2.5 hours, then treated in a similar manner to Example 1b and extracted with dichloromethane to give an oil which was dissolved in ether and treated with ethereal hydrogen chloride to give a solid which was recrystallised from propan-2-ol/ether (2:1) to give N-[2-(4-chlorophenoxy)-1,1-dimethylethyl]-3-(imidazol-1-yl) propylamine dihydrochloride, m.p. 155–156° C.

EXAMPLES 18–23

Compounds of formula XVI, in which $R_6$ represents hydrogen and $R_1$, $R_2$, $R_3$ and (-$L_1$-T-$L_2$-) are as defined in Table 3, were reacted with compounds of formula XXVII, in which $R_8$, $R_9$ and $R_{10}$ are as defined in Table 3, in a similar manner to Example 17a, as summarised in Table 3, to give compounds of formula IX in which Q represents -$(CH_2)_2$-.

Compounds of formula IX in which Q represents -$(CH_2)_2$- were reduced, in a similar manner to Example 17b, as summarised in Table 4 to give compounds of formula I. In examples 22b and 23b additional reduction of the substituent $R_8$ and $R_9$, respectively, occurred.

TABLE 3

| | ACRYLAMIDE XVI | | | IMIDAZOLE XXVII | | | | S Vol | Tr Vol | | |
|---|---|---|---|---|---|---|---|---|---|---|---|
| Ex | $R_1R_2R_3$ | $L_1$-T-$L_2$ | Wt/g | $R_8$ | $R_9$ | $R_{10}$ | Wt/g | ml | ml | T | W |
| 18a | 4-Cl | S-C(CH$_3$)$_2$-CH$_2$ | 6.50 | H | H | H | 1.63 | 50 | 0.57 | 5 | |
| 19a | 4-Cl | S-CH$_2$-C(CH$_3$)$_2$ | 5.90 | H | H | H | 1.49 | 46 | 0.52 | 5 | 1 |
| 20a | a | S-CH$_2$-C(CH$_3$)$_2$ | 1.95 | H | H | H | 0.45 | 15 | 0.20 | 4 | |
| 21a | 4-Cl | CH$_2$-C(CH$_3$)$_2$ | 6.00 | H | H | H | 1.77 | 60 | 0.39 | 16 | |
| 22a | 4-Cl | C(CH$_3$)$_2$ | 8.30 | H | b | H | 3.95 | 80 | 1.0 | 4.5 | |
| 23a | 4-Cl | C(CH$_3$)$_2$ | 6.69 | c | H | H | 6.41 | 100 | 2.0 | 168 | 2 | a = 2,5-dimethyl-4-chloro
c = COPh
T = Reflux Time (Hours)
S = 1,4-dioxane
b = CH$_2$CN;
W = Work Up Procedure
Tr = Triton B

TABLE 4

| | IX | | | | | | BOR Vol | THF Vol | | |
|---|---|---|---|---|---|---|---|---|---|---|
| Ex | $R_1R_2R_3$ | $L_1$-T-$L_2$ | $R_8$ | $R_9$ | $R_{10}$ | Wt/g | ml | ml | T | W |
| 18b | 4-Cl | S-C(CH$_3$)$_2$-CH$_2$ | H | H | H | 5.44 | 64.3 | 111 | 1.5 | |
| 19b | 4-Cl | S-CH$_2$-C(CH$_3$)$_2$ | H | H | H | 3.60 | 42.5 | 84 | 2.5 | |
| 20b | a | S-CH$_2$-C(CH$_3$)$_2$ | H | H | H | 1.80 | 25.0 | 40 | 3.5 | |
| 21b | 4-Cl | CH$_2$-C(CH$_3$)$_2$ | H | H | H | 4.58 | 60.0 | 110 | 3.0 | |
| 22b | 4-Cl | C(CH$_3$)$_2$ | H | b | H | 4.96 | 60.0 | 110 | 4.0 | |
| 23b | 4-Cl | C(CH$_3$)$_2$ | c | H | H | 1.30 | 16.5 | 25 | 2.5 | 1 | a = 2,5-dimethyl-4-chloro
c = COPh
W = Work Up Procedure
b = CH$_2$CN;
T = Reflux Time (Hours)
BOR = 1.0M BH$_3$/THF Notes to Table 3

1. Product recrystallised from cyclohexane/ethyl acetate.
2. After boiling for 3 days, pyridine (10 ml) was added and the mixture boiled for a further 4 days. The product was purified by flash column chromatography on silica.

Notes to Table 4

1. An oil was obtained after treatment with ethereal hydrogen chloride. The oil was basified and extracted into ethyl acetate to give the product.

The products prepared in Table 4 are listed below:

EXAMPLE 18

2-(4-Chlorophenylthio)-3'-(imidazol-1-yl)-2-methyldipropylamine dihydrochloride, m.p. 174–175.5° C.

EXAMPLE 19

N-[2-(4-Chlorophenylthio)-1,1-dimethylethyl]-3-(imidazol-1-yl)propylamine dihydrochloride, m.p. 209–211° C. (from propan-2-ol/ethanol).

EXAMPLE 20

N-[2-(4-Chloro-2,5-xylylthio)-1,1-dimethylethyl]-3-(imidazol-1-yl)propylamine dihydrochloride, m.p. 211–214° C. (from ethanol/ethyl acetate).

EXAMPLE 21

N-[2-(4-Chlorophenyl)-1,1-dimethylethyl]-3-(imidazol-1-yl)propylamine dihydrochloride, m.p. 225–227° C. (after trituration with ether).

EXAMPLE 22

3-[4-(2-Aminoethyl)imidazol-1-yl]-N-[1-(4-chlorophenyl)-1-methylethyl]propylamine trihydrochloride, m.p. 250–251° C. (after trituration with propan-2-ol).

EXAMPLE 23

α-(1-{3-[1-(4-Chlorophenyl)-1-methylethylamino]propyl}-imidazol-2-yl)benzyl alcohol as an oil not distilled.

EXAMPLE 24

A solution of 3-(imidazol-1-yl)propionaldehyde diethyl acetal, (2.5 g, prepared as described in DE 2,842,759, by reacting imidazole with 3-chloropropionaldehyde diethyl acetal in the presence of sodium hydride) in 5M hydrochloric acid (10 ml) was left to stand at ambient temperature overnight. The solution was basified with solid sodium bicarbonate, sodium chloride was added and the mixture extracted with chloroform. The combined chloroform extracts were concentrated under reduced pressure at ambient temperature to give a solution of 3-(imidazol-1-yl)propionaldehyde in a small volume of chloroform. This aldehyde was dissolved in acetonitrile (20 ml). 1-Methyl-1-

[4-(3,4-xylylsulphonylmethyl)phenyl]-ethylamine(2.0 g) and molecular sieves type 4A, (1.0 g) were added to this solution and the mixture was stirred at ambient temperature overnight. The mixture was filtered. The filtrate was evaporated under reduced pressure to give a residue which was dissolved in absolute ethanol (20 ml). Sodium borohydride (1.4 g) was added to the solution and the mixture was boiled under reflux for 3 hours. The mixture was evaporated to dryness. Dilute sodium hydroxide solution was added to the residue and the mixture extracted with ethyl acetate to give an oil which was purified by flash chromatography on silica, using ethyl acetate/triethylamine (98:2) as the mobile phase to elute unreacted starting material and then ethyl acetate/methanol (9:1) to elute the product as an oil which was dissolved in ether and acidified with ethereal hydrogen chloride. The precipitate was collected by filtration and recrystallised from propan-2-ol containing a small amount of water to give 3-(imidazol-1-yl)-N-{1-methyl-1-[4-(3,4-xylylsulphonylmethyl)-phenyl]ethyl}propylamine dihydrochloride hydrate, m.p. 150° C.

EXAMPLES 25–42

In a similar manner to Example 24, compounds of formula VII in which $R_6$ is hydrogen were reacted with 3-(imidazol-1-yl)propionaldehyde prepared from the diethyl acetal [VIII in Table 5] in acetonitrile in the presence of molecular sieves type 4A (MS) to give compounds of formula VI which were reduced with sodium borohydride to give compounds of formula I as summarised in Table 5. The values of the substituents on VII are given in Table 5. The crude product was purified by flash column chromatography on silica using ethyl acetate/triethylamine (9:1) as the mobile phase with increasing amounts of methanol, unless otherwise stated. As is obvious from the name of the product obtained, in certain cases the conversion of the product into the hydrochloride salt was omitted.

Notes to Table 5

1. The crude product was purified by distillation under high vacuum (b.p. 190–200° C. at 0.06 mbar) and then treated with ethereal hydrogen chloride.
2. The reaction of amine VII with the aldehyde VIII was carried out in ethanol. The crude product was purified by distillation under high vacuum (b.p. 150–170° C. at 0.04 mbar).
3. As in note 1 (b.p. 185–190° C. at 0.03 mbar).
4. The oil obtained on work-up was treated with ethereal hydrogen chloride to give a hygroscopic hydrochloride salt which was basified and extracted to give the product as the free base.
5. As in note 2 (b.p. 180° C. at 0.07 mbar).
6. The crude product oil was dissolved in ether and a solution of maleic acid (4.0 g) in ether was added. The gum obtained after decanting off the solvent was recrystallised from acetone to give the solid product.

The compounds prepared in Examples 25–42 were as follows:

EXAMPLE 25

N-{1-[4-(Hexylsulphonylmethyl)phenyl]-1-methylethyl}-3-(imidazol-1-yl)propylamine dihydrochloride, m.p. 124–125° C.

EXAMPLE 26

4-{1-[3-(Imidazol-1-yl)propylamino]-1-methylethyl}-N,N-dipropylbenzenesulphonamide, m.p. 104–106° C.

EXAMPLE 27

N-{1-[4-(2-Benzyloxyethyl)phenyl]-1-methylethyl}-3-(imidazol-1-yl)propylamine as an oil

TABLE 5

| | | Reaction (a) | | | | Reaction (b) | | |
|---|---|---|---|---|---|---|---|---|
| | AMINE VII | | | VIII | MS | EtOH | NaBH$_4$ | |
| EX | R$_1$R$_2$R$_3$ | -L$_1$-T-L$_2$- | Wt/g | Wt/g | Wt/g | Vol/ml | Wt/g | Note |
| 25 | 4-C$_6$H$_{13}$SO$_2$CH$_2$ | —C(CH$_3$)$_2$— | 3.50 | 4.67 | 1.50 | 38.0 | 2.62 | |
| 26 | 4-(C$_3$H$_7$)$_2$NSO$_2$ | —C(CH$_3$)$_2$— | 2.40 | 4.40 | 2.10 | 30.0 | 0.76 | |
| 27 | 4-BzO(CH$_2$)$_2$ | —C(CH$_3$)$_2$— | 3.00 | 1.36 | 3.00 | 25.0 | 0.86 | |
| 28 | a | —C(CH$_3$)$_2$— | 2.50 | 5.71 | 2.50 | 50.0 | 0.84 | |
| 29 | 4-C$_6$H$_{13}$NHCO | —C(CH$_3$)$_2$— | 0.46 | 0.71 | 0.40 | 10.0 | 0.21 | |
| 30 | b | —C(CH$_3$)$_2$— | 0.60 | 0.81 | 0.40 | 10.0 | 0.24 | |
| 31 | 4-CN | —O—CH$_2$—CH$_2$— | 3.40 | 8.00 | 7.00 | 50.0 | 1.60 | 1 |
| 32 | 4-Cl | c | 14.7 | 8.00 | — | 30.0 | 4.77 | 2 |
| 33 | 4-CH$_3$S | —O—CH$_2$—C(CH$_3$)$_2$— | 2.50 | 8.10 | 6.00 | 50.0 | 1.20 | 3 |
| 34 | d | O—C(C$_3$H$_7$)$_2$— | 0.35 | 0.66 | 0.40 | 15.0 | 0.17 | |
| 35 | H | —O—CH$_2$—C(CH$_3$)$_2$— | 2.1 | 8.00 | 6.00 | 50.0 | 1.20 | 4 |
| 36 | 2-OCH$_3$ | —(CH$_2$)$_2$—C(CH$_3$)$_2$— | 3.96 | 8.10 | 6.00 | 50.0 | 3.12 | 5 |
| 37 | e | —C(CH$_3$)$_2$— | 1.00 | 1.49 | 0.8 | 30.0 | 0.44 | |
| 38 | f | —C(CH$_3$)$_2$— | 1.00 | 1.25 | 0.7 | 30.0 | 0.37 | |
| 39 | 4-CF$_3$ | —O—CH$_2$—C(CH$_3$)$_2$— | 3.00 | 8.00 | 10.0 | 50.0 | 3.25 | 6 |
| 40 | 4-F | —O—CH$_2$—C(CH$_3$)$_2$— | 3.00 | 8.00 | 10.0 | 50.0 | 4.50 | 6 |
| 41 | HOCH$_2$C(C$_2$H$_5$)$_2$- | —C(CH$_3$)$_2$— | 1.00 | 1.82 | 1.0 | 40.0 | 0.54 | |
| 42 | g | —C(CH$_3$)$_2$— | 2.00 | 2.58 | 1.4 | 50.0 | 0.76 | | a = 4-(N-cyclohexylcarbamoyl)
b = 4-[N-(4-chlorobenzyl)carbamoylmethyl]
c = 2-(1,3-dioxolan-2-yl)ethyl
d = 4-(N-methylcarbamoylmethyl)
e = 4-(N-cycloheptylcarbamoylmethyl)
f = 4-[2-(4-cyanobenzenesulphonamido)ethyl]
g = 4-[2-(4-methoxybenzenesulphonamido)ethyl]
Bz = benzyl

EXAMPLE 28

N-Cyclohexyl-4-{1-[3-(imidazol-1-yl)propylamino]-1-methylethyl}benzamide, m.p. 126–131° C.

EXAMPLE 29

N-Hexyl-4-{1-[3-(imidazol-1-yl)propylamino]-1-methylethyl}phenylacetamide, as an oil.

EXAMPLE 30

N-(4-Chlorobenzyl)-4-{1-[3-(imidazol-1-yl)propylamino]-1-methylethyl}phenylacetamide, as an oil.

EXAMPLE 31

4-{2-[3-(Imidazol-1-yl)propylamino]ethoxy}benzonitrile sesquihydrochloride, m.p. 176–178° C.

EXAMPLE 32

N-{2-[2-(4-Chlorophenyl)-1,3-dioxolan-2-yl]ethyl}-3-(imidazol-1-yl)propylamine, b.p. 150–170° C. at 0.04 mbar.

EXAMPLE 33

N-[1,1-Dimethyl-2-(4-methylthiophenoxy)ethyl]-3-(imidazol-1-yl)propylamine dihydrochloride hydrate, m.p. 177–179° C.

EXAMPLE 34

4-{1-[3-(Imidazol-1-yl)propylamino]-1-propylbutyl}-phenyl-N-methylacetamide, as an oil.

EXAMPLE 35

3-(Imidazol-1-yl)-N-(1,1-dimethyl-2-phenoxyethyl) propylamine, as an oil.

EXAMPLE 36

3'-(Imidazol-1-yl)-3-(2-methoxyphenyl)-1,1-dimethyldipropylamine, b.p. 180° C. at 0.06 mbar.

EXAMPLE 37

N-Cycloheptyl-4-{1-[3-(imidazol-1-yl)propylamino]-1-methylethyl}phenylacetamide, as an oil.

EXAMPLE 38

4-Cyano-N-[2-(4-{1-[3-(imidazol-1-yl)propylamino]-1-methylethyl}phenyl)ethyl]benzenesulphonamide, as an oil.

EXAMPLE 39

N-{2-[4-(Trifluoromethyl)phenoxy]-1,1-dimethylethyl}-3-(imidazol-1-yl)propylamine dimaleate, m.p. 144–144.5° C.

EXAMPLE 40

N-[2-(4-Fluorophenoxy)-1,1-dimethylethyl]-3-(imidazol-1-yl)propylamine dimaleate hemihydrate, m.p. 131–132.5° C.

EXAMPLE 41

2-Ethyl-2(4-{1-[3-(imidazol-1-yl)propylamino]-1-methylethyl}phenyl)butan-1-ol, as an oil.

EXAMPLE 42

N-[2-(4-{1-[3-(Imidazol-1-yl)propylamino]-1-methylethyl}phenyl)ethyl]-4-methoxybenzenesulphonamide, as an oil.

EXAMPLE 43 a) Epichlorohydrin (8.05 ml) was added dropwise to a solution of 1-(4-chlorophenyl)-1-methylethylamine (17.38 g) in methanol (17.5 ml) at 0° C. with stirring. The solution was warmed to ambient temperature and stirred for 48 hours. Sodium hydroxide solution (50%) (17.5 ml) was added and the mixture stirred for 15 minutes. The product was extracted with ether to give an oil which was purified by flash column chromatography on silica using petroleum ether, b.p. 40–60° C./ethyl acetate/triethylamine (8:2:1) as the mobile phase with gradually increasing amounts of ethyl acetate to give N-[1-(4-chlorophenyl)-1-methylethyl]-2,3-epoxypropylamine as an oil.

b) A mixture of the product from a) (4.0 g), imidazole (6.12 g) and ethanol (25 ml) was boiled under reflux for 16 hours. The mixture was cooled and the solvent removed under reduced pressure, water was added and the product extracted into chloroform to give an oil which was purified by flash column chromatography on silica using ethyl acetate/triethylamine (9:1) as the mobile phase with increasing amounts of methanol to give an oil which was recrystallised from petroleum ether, b.p. 60–80° C./ethyl acetate (4:1) to give 1-[1-(4-chlorophenyl)-1-methylethylamino]-3-(imidazol-1-yl)propan-2-ol, m.p. 89–91° C.

EXAMPLE 44–53

Examples 44–53 were carried out in a similar manner to Example 43. Compounds of formula VII were reacted with epichlorohydrin (E) to give compounds of formula XVII (Reaction a) which were reacted with imidazole (IM in Table) (Reaction b) to give compounds of formula I as summarised in Table 6. The amounts of solvents and inorganic reagents used in both reactions were equivalent (on a molar basis) to those used in Example 43. The reaction times and the chromatographic conditions were as described in Example 43.

TABLE 6

| | | Reaction (a) | | | Reaction (b) | | |
|---|---|---|---|---|---|---|---|
| | | AMINE VII | | | XVII | IM | |
| EX | R₁R₂R₃ | —L₁—T—L₂— | Wt/g | E (ml) | Wt/g | Wt/g | Note |
| 44 | H | —C(CH₃)₂— | 3.00 | 1.44 | 0.76 | 1.20 | |
| 45 | 4-Cl | —C(CH₃)₂— | 2.80 | 0.85* | 1.50 | 2.26 | |
| 46 | 4-Cl | —C(CH₃)₂— | 2.80 | 0.85† | 1.50 | 2.26 | |
| 47 | a | —C(CH₃)₂— | 2.63 | 0.60 | 1.08 | 1.11 | |
| 48 | b | —C(CH₃)₂— | 2.50 | 0.60 | 1.50 | 1.61 | |

TABLE 6-continued

| | | Reaction (a) | | | Reaction (b) | | |
|---|---|---|---|---|---|---|---|
| | | AMINE VII | | | XVII | IM | |
| EX | $R_1R_2R_3$ | —$L_1$—T—$L_2$— | Wt/g | E (ml) | Wt/g | Wt/g | Note |
| 49 | c | —C(CH$_3$)$_2$— | 6.45 | 1.74 | 3.80 | 4.50 | |
| 50 | d | —C(CH$_3$)$_2$— | 8.50 | 1.67 | 3.63 | 3.31 | |
| 51 | 4-SCH$_3$ | —O—CH$_2$—C(CH$_3$)$_2$— | 3.43 | 0.83 | 1.57 | 2.00 | |
| 52 | 4-Cl | —O—CH$_2$—C(CH$_3$)$_2$— | 5.74 | 1.50 | 3.50 | 4.65 | 1 |
| 53 | H | —O—CH$_2$—C(CH$_3$)$_2$— | 2.00 | 0.62 | 1.15 | 1.77 | 1 |

*R-epichlorohydrin
†S-epichlorohydrin
a = 4-(N-hexylcarbamoylmethyl)
b = 4-(N-cyclohexylcarbamoyl)
c = 4-(4,4-dimethyl-2-oxazolin-2-yl)
d = 4-(3,4-xylylsulphonylmethyl)

Notes to Table 6

1. The product fraction after chromatography was contaminated with imidazole which was removed by sublimation by heating at 100° C. at 0.07 mbar for 4 hours.
The compounds prepared in examples 44–53 were as follows:

EXAMPLE 44

1-(1-Ethyl-1-phenylpropylamino)-3-(imidazol-1-yl)-propan-2-ol, m.p. 131–132° C.

EXAMPLE 45

(+)-1-[1-(4-Chlorophenyl)-1-methylethylamino]-3-(imidazol-1-yl)propan-2-ol, $[\alpha]_D$=+9.50.

EXAMPLE 46

(−)-1-[1-(4-Chlorophenyl)-1-methylethylamino]-3-(imidazol-1-yl)propan-2-ol, $[\alpha]_D$=−10.30.

EXAMPLE 47

N-Hexyl-4-{1-[2-hydroxy-3-(imidazol-1-yl)propylamino]-1-methylethyl}phenylacetamide, m.p. 125–127° C.

EXAMPLE 48

N-Cyclohexyl-4-{1-[2-hydroxy-3-(imidazol-1-yl)propylamino]-1-methylethyl}benzamide, m.p. 70° C.

EXAMPLE 49

1-{1-[4-(4,4-Dimethyl-2-oxazolin-2-yl)phenyl]-1-methylethylamino}-3-(imidazol-1-yl)propan-2-ol hemihydrate, as an oil.

EXAMPLE 50

1-(Imidazol-1-yl)-3-{1-methyl-1-[4-(3,4-xylylsulphonylethyl)phenyl]ethylamino}propan-2-ol, m.p. 160–162° C.

EXAMPLE 51

3-(Imidazol-1-yl)-1-[2-(4-methylthiophenoxy)-1,1-dimethylethylamino]propan-2-ol, as an oil.

EXAMPLE 52

1-[2-(4-Chlorophenoxy)-1,1-dimethylethylamino]-3-(imidazol-1-yl)propan-2-ol, as an oil.

EXAMPLE 53

3-(Imidazol-1-yl)-1-(2-phenoxy-1,1-dimethylethylamino) propan-2-ol, as an oil.

EXAMPLE 54

Triethylamine (0.46 g) was added to a stirred suspension of 3-[4-(2-aminoethyl)imidazol-1-yl]-N-[1-(4-chlorophenyl)-1-methylethyl]propylamine trihydrochloride (0.65 g) in dichloromethane (20 ml). The solution was cooled to 0° C. and benzenesulphonyl chloride (0.27 g) in dichloromethane (10 ml) was added dropwise with stirring. The mixture was stirred at 0° C. for 30 minutes and then at ambient temperature for 3 hours. The mixture was washed with water, sodium bicarbonate solution and then dried, filtered and evaporated to give a yellow oil which was dissolved in alcohol and treated with ethereal hydrogen chloride. The resulting salt was hygroscopic and so was converted back to the free base by treatment with aqueous sodium hydroxide solution to give N-[2-(1-{3-[1-(4-chlorophenyl)-1-methylethylamino]propyl)imidazol-4-yl) ethyl]benzenesulphonamide as an oil.

EXAMPLE 55

Triethylamine (0.46 g) was added to a stirred suspension of 3-[4-(2-aminoethyl)imidazol-1-yl]-N-[1-(4-chlorophenyl)-1-methylethyl]propylamine trihydrochloride, (0.65 g) in dichloromethane (25 ml) and the resulting solution cooled to 0° C. A solution of benzoyl chloride (0.21 g) in dichloromethane (10 ml) was added over 20 minutes at 0–5° C. with stirring. The mixture was stirred at ambient temperature for 2.5 hours. The solution was washed with sodium bicarbonate solution, then water, then dried, filtered and evaporated to give N-[2-(1-(3-[1-(4-chlorophenyl)-1-methylethylamino]propyl}imidazol-4-yl)ethyl]benzamide as an oil.

EXAMPLE 56

A solution of benzenesulphonyl chloride (0.25 g) in dichloromethane (3 ml) was added dropwise to a solution of N-{1-[4-(2-aminoethyl)phenyl]-1-methylethyl}-3-(imidazol-1-yl)propylamine (0.4 g) in dichloromethane (7 ml) with stirring at 0° C. The mixture was treated in a similar manner to Example 55 to give N-[2-(4-{1-[3-(imidazol-1-yl)propylamino]-1-methylethyl}phenyl)ethyl]-benzenesulphonamide as an oil.

EXAMPLE 57

A solution of benzoyl chloride (0.2 g) in dichloromethane (3 ml) was added dropwise to a solution of N-{1-[4-(2- aminoethyl)phenyl]-1-methylethyl}-3-(imidazol-1-yl) propylamine (0.4 g) in dichloromethane (7 ml) with stirring at 0° C. The mixture was treated in a similar manner to Example 55 to give N-[2-(4-{1-[3-(imidazol-1-yl) propylamino]-1-methylethyl}phenyl)-ethyl]benzamide as an oil.

EXAMPLE 58

A solution of butylisocyanate (0.17 g) in dichloromethane was added to a solution of N-{1-[4-(2-aminoethyl)phenyl]-1-methylethyl}-3-(imidazol-1-yl)propylamine (0.5 g) in dichloromethane (7 ml). The mixture was boiled under reflux for 30 minutes and then the solvent removed under reduced pressure. The residue was purified by flash chromatography on silica using methanol as the mobile phase to give N-butyl-N'-[2-(4-{1-[3-(imidazol-1-yl)propylamino]-1-methylethyl}phenyl)ethyl]urea as an oil.

EXAMPLE 59

N-[1-(4'-Benzyloxybiphenyl-4-yl)-1-methylethyl]-3-(imidazol-1-yl)propylamine was hydrogenated, using palladium on charcoal as catalyst, in IMS at atmospheric pressure to give 4'-{1-[3-(imidazol-1-yl)propylamino]-1-methylethyl}biphenyl-4-ol, m.p. 178–180° C.

EXAMPLE 60

3-[4-(2-Aminoethyl)imidazol-1-yl]-N-(1-ethyl-1-phenylpropyl)propylamine (1.0 g) was reacted with benzoyl chloride (0.38 ml) in a similar manner to Example 55 to give N-(2-{1-[3-(1-ethyl-1-phenylpropylamino)propyl]imidazol-4-yl}ethyl)benzamide, as an oil.

EXAMPLE 61

3-[4-(2-Aminoethyl)imidazol-1-yl]-N-(1-ethyl-1-phenylpropyl)propylamine (0.5 g) was reacted with 4-methoxybenzoyl chloride (0.29 g) in a similar manner to Example 55 to give N-(2-{1-[3-(1-ethyl-1-phenylpropylamino)propyl]-imidazol-4-yl}ethyl)-4-methoxybenzamide, as an oil.

EXAMPLE 62

3-[4-(2-Aminoethyl)imidazol-1-yl]-N-(1-ethyl-1-phenylpropyl)propylamine (0.5 g) was reacted with 4-cyanobenzoyl chloride (0.27 g) in a similar manner to Example 55 to give 4-cyano-N-(2-{1-[3-(1-ethyl-1-phenylpropylamino)propyl]imidazol-4-yl}ethyl)benzamide, m.p. 107–109° C.

EXAMPLE 63

N-[1-(4-Chlorophenyl)-1-methylethyl]-2,3-epoxypropylamine was reacted with a mixture of imidazol-4(5)-ylacetonitrile in DMF/THF (5:1) and an equivalent of sodium hydride at 20° C. under nitrogen. The mixture then was heated at 95° C. for 2 hours, cooled, quenched with ammonium chloride solution and extracted with ethyl acetate to give 1-{3-[1-(4-chlorophenyl)-1-methylethylamino]-2-hydroxypropyl}imidazol-4-ylacetonitrile after purification by chromatography. This product was reduced with borane (in a similar manner to Example 17) to give the corresponding 4-(2-aminoethyl) compound which was then reacted with benzoyl chloride in a similar manner to Example 55 to give N-[2-(1-{3-[1-(4-chlorophenyl)-1-methylethylamino]-2-hydroxypropyl}imidazol-4-yl)ethyl]benzamide as an oil.

EXAMPLE 64

N-[2-(4-Chlorophenoxy)ethyl]-3-(imidazol-1-yl) propylamine (1.50 g) was added dropwise to 98% formic acid (1.0 ml) at 0° C. Formaldehyde (0.96 ml of a 37% aqueous solution) was added and the mixture heated at 95° C. for 6 hours. On cooling, concentrated hydrochloric acid (0.6 ml) was added. The mixture was evaporated to dryness and the residue dissolved in water, basified with 5M sodium hydroxide solution and extracted with ethyl acetate to give N-[2-(4-chlorophenoxy)ethyl]-3-(imidazol-1-yl)-N-methylpropylamine as an oil.

EXAMPLE 65

Methyl bromoacetate (2.1 g) was added to a stirred mixture of N-[2-(4-chlorophenoxy)ethyl]-3-(imidazol-1-yl) propylamine (3.87 g) and anhydrous potassium carbonate (5.73 g) in dry acetone (180 ml). The mixture was stirred and boiled under reflux for 7 hours, then left to stand at ambient temperature for 18 hours then hot filtered. The filtrate was evaporated to dryness and the residue was purified by chromatography on silica using ethyl acetate/triethylamine, 9 to 1 as the mobile phase. The product was obtained as an oil which was dissolved in ether, and extracted into 5M hydrochloric acid. The acid extracts were basified with 5M sodium hydroxide solution and the product extracted into ether to give methyl N-[2-(4-chlorophenoxy)ethyl)-N-[3-(imidazol-1-yl)propyl]glycinate as an oil.

EXAMPLE 66

Lithium aluminium hydride (0.23 g) was added to a solution of methyl N-[2-(4-chlorophenoxy)ethyl]-N-[3-(imidazol-1-yl)propyl]glycinate (1.30 g) in THF (30 ml). The mixture was boiled under reflux for 4 hours and then cooled. Water (1 ml) was added followed by 5M sodium hydroxide solution (2 ml) and then more water (2 ml). The mixture was filtered to remove the precipitate using a filtration aid. The filtrate was washed with water, dried and evaporated to give 2-{N-[2-(4-chlorophenoxy)-ethyl]-N-[3-(imidazol-1-yl)propyl]amino}ethanol as an oil.

EXAMPLE 67 a) N-[2-(4-Benzyloxyphenoxy)ethyl]-3-(imidazol-1-yl) propylamine dihydrochloride hydrate (4.24 g) was suspended in IMS (200 ml) and methanol (10 ml) and hydrogenated at atmospheric pressure using 10% palladium/charcoal as a catalyst (0.44 g). The mixture was filtered and the filtrate evaporated to give a residue which was triturated with warm ether and filtered to give a solid which was recrystallised from methanol/ether to give 4-{2-[3-(imidazol-1-yl)propylamino]ethoxy}phenol dihydrochloride, m.p. 195–197° C.

b) The product from a) (0.64 g), triethylamine (0.3 ml) and dichloromethane (20 ml) was stirred for 10 minutes at ambient temperature then cooled to 0° C. and a solution of n-butanesulphonyl chloride (0.30 g) in dichloromethane (5 ml) was added dropwise with stirring. The mixture was stirred at 0° C. for 30 minutes and then at ambient temperature for 3 hours. The mixture was washed with water, then dried, filtered and evaporated to give an oil which was triturated with boiling ether and filtered. The filtrate was evaporated to give 4-{2-[3-(imidazol-1-yl)propylamino] ethoxy}phenyl 1-butane sulphonate as an oil.

EXAMPLE 68

N-[2-(4-Chlorophenylthio)-1,1-dimethylethyl]-3-(imidazol-1-yl)propylamine dihydrochloride (1.0 g) was added in one portion to a stirred solution of sodium periodate (0.54 g) in aqueous methanol (15 ml of a 1:1 mixture) at 5–10° C. The mixture was stirred at ambient temperature for 24 hours and then evaporated to dryness. 5M Sodium hydroxide solution was added to the residue and the mixture extracted with dichloromethane to give an oil which was dissolved in ether containing a small amount of absolute alcohol and treated with ethereal hydrogen chloride. The mixture was filtered to give N-[2-(4-chlorophenylsulphinyl)-1,1-dimethylethyl]-3-(imidazol-1-yl)propylamine dihydrochloride, m.p. 208–211° C.

EXAMPLE 69 a) N-[2-(4-Chloro-2,5-xylylthio)-1,1-dimethylethyl]-3-imidazol-1-yl)propylamine dihydrochloride (4.0 g) in trifluoroacetic acid (13 ml) was stirred at 0° C. and 3 M trifluoroperacetic acid (7.6 ml of 3 M solution in trifluoroacetic acid) (prepared from 30% $H_2O_2$ (8.6 ml) and trifluoroacetic acid made up to a total volume of 25 ml), was added dropwise. The mixture was stirred at 0° C. for 2 hours and then at 60° C. for 2 hours. Further trifluoroperacetic acid (3 M, 0.5 ml) was added and the mixture heated at 60–65° C. for a further 2.5 hours. The mixture was allowed to stand at ambient temperature overnight. Further trifluoroperacetic acid (3 M, 0.5 ml) was added and the mixture stirred at 60–65° C. for a further 4 hours. This addition was repeated and finally the mixture was allowed to cool, diluted with dichloromethane, washed with saturated sodium bicarbonate solution and then water and the organic layer dried, filtered and evaporated to give a residue which was recrystallised from ethanol/ethyl acetate to give N-[2-(4-chloro-2,5-xylylsulphonyl)-1,1-dimethyl-ethyl]-3-(imidazol-1-yl) propylamine dihydrochloride hemihydrate, m.p. 210–211° C.

EXAMPLE 70

In a similar manner to Example 69, N-[2-(4-t-butylphenylthio)-1,1-dimethylethyl]-3-(imidazol-1-yl) propylamine dihydrochloride, was oxidised to give N-[2-(4-t-butylphenylsulphonyl)-1,1-dimethylethyl]-3-(imidazol-1-yl)-propylamine dihydrochloride, m.p. 218–220° C.

EXAMPLE 71

A solution of benzenesulphonyl chloride (0.51 g) in dichloromethane (5 ml) was added in portions over 5 minutes to a solution of 4-{1-[3-(imidazol-1-yl) propylamino]-1-methylethyl}phenol (0.75 g) and triethylamine (0.29 g) in dichloromethane (5 ml) at 0° C. with stirring. The mixture was stirred at ambient temperature for 3 hours then diluted with dichloromethane and washed with water. The organic layer was separated, dried and evaporated. The residue was purified by flash column chromatography on silica using methanol as the mobile phase to give 4-{1-[3-(imidazol-1-yl)propylamino]-1-methylethyl}phenyl benzenesulphonate as an oil.

EXAMPLE 72

In a similar manner to Example 71, a solution of butanesulphonyl chloride (0.45 g) in dichloromethane (5 ml) was added in portions over 5 minutes to a solution of 4-{1-[3-(imidazol-1-yl)propylamino]-1-methylethyl}phenol (0.75 g) and triethylamine (0.29 g) in dichloromethane (5 ml) at 0° C. with stirring, to give 4-{1-[3-(imidazol-1-yl) propylamino]-1-methylethyl}phenyl 1-butanesulphonate as an oil.

EXAMPLE 73

Benzoyl chloride (0.21 ml) was added to a solution of N-[1-(3-amino-4-chlorophenyl)-1-methylethyl]-3-(imidazol-1-yl)propylamine (0.50 g) in dichloromethane (50 ml) and triethylamine (0.25 ml) with stirring at 0° C. The mixture was allowed to warm up to ambient temperature and stirred at this temperature for 18 hours. The mixture was washed with water, dried and evaporated. The residue was purified by flash column chromatography on silica using ethyl acetate/methanol/triethylamine (8:1:1) as the mobile phase. The product was obtained as an oil which was added to ethereal hydrogen chloride to produce a gum. The gum was triturated and then left standing for 18 hours. The resulting solid was ground up, filtered and dried to give 2'-chloro-5'-{1-[3-(imidazol-1-yl)propylamino]-1-methylethyl}benzanilide.

EXAMPLE 74

A mixture of 1-{1-[4-(4,4-dimethyl-2-oxazolin-2-yl) phenyl]-1-methylethylamino}-3-(imidazol-1-yl)propan-2-ol (100 mg) and a solution of sulphuric acid in propan-1-ol (5 ml) [prepared by adding concentrated sulphuric acid (4 ml) and then water (5 ml) to propan-1-ol (50 ml) and making up to 100 ml with propan-1-ol] was heated on a steam bath for 18 hours. The mixture was evaporated under reduced pressure. The residue was basified with aqueous sodium hydroxide solution and then extracted with dichloromethane to give a residue which was purified by flash column chromatography on silica using ethyl acetate/triethylamine (9:1) with increasing amounts of ethanol to give propyl 4-{1-[2-hydroxy-3-(imidazol-1-yl)propylamino]-1-methylethyl}benzoate as an oil.

EXAMPLE 75 a) A solution of 5-chlorovaleryl chloride (3.76 g) in dichloromethane (8 ml) was added dropwise with stirring to a mixture of 1-methyl-(1-phenoxymethyl)ethylamine (4.0 g) and triethylamine (2.9 g) in dichloromethane (30 ml) whilst keeping the temperature below 0° C. After the addition the reaction mixture was allowed to warm to ambient temperature and then stirred at that temperature for 2 hours. The mixture was worked up in a similar manner to Example 55 to give 5-chloro-N-(1,1-dimethyl-2-phenoxyethyl) valeramide as an oil.

b) A solution of imidazole (2.37 g) in dry THF (20 ml) was added dropwise with stirring to a suspension of sodium hydride (1.64 g of a 60% dispersion in mineral oil which had been washed with petroleum ether, b.p. 40–60° C.) in dry THF (75 ml) at ambient temperature under nitrogen. The mixture was stirred at ambient temperature for 2 hours, heated to boiling under reflux and then cooled to ambient temperature. A solution of the product from Part a) (6.6 g) in dry THF (20 ml) was added to the reaction mixture at ambient temperature with stirring. Further THF (20 ml) was added and the mixture stirred and boiled under reflux for 18 hours. The mixture was cooled in ice and a few drops of water were cautiously added. The mixture was filtered. The filtrate was evaporated to dryness to give a residue which was dissolved in ethyl acetate, washed with water, dried and evaporated to give an oil which was chromatographed on silica using ethyl acetate/methanol/triethylamine (75:20:5) as the mobile phase to give 5-(imidazol-1-yl)-N-(1,1-dimethyl-2-phenoxyethyl)valeramide as an oil which was used directly in Part c).

c) Borane/THF (21.0 ml, 1.0 molar solution) was added to a solution of the product from Part b) (1.56 g) in dry THF (37 ml). The mixture was boiled under reflux for 2.5 hours and then the solvent was removed under reduced pressure. The residue was heated at 95° C. for 0.5 hour, then cooled and diluted with 1M hydrochloric acid (10 ml). This mixture was heated at 95° C. for 2 hours and then worked up in a similar manner to Example 1b to give an oil which was distilled under vacuum to give 5-(imidazol-1-yl)-N-(1,1-dimethyl-2-phenoxyethyl)pentylamine, b.p. 160° C. at 0.02 mbar.

EXAMPLE 76

3-[4-(2-Aminoethyl)imidazol-1-yl]-N-(1,1-dimethyl-2-phenoxyethyl)propylamine (2.50 g) and benzoyl chloride (1.10 g) were reacted in a similar manner to Example 55 to give N-(2-{1-[3-(1,1-dimethyl-2-phenoxyethylamino)-propyl]imidazol-4-yl}ethyl)benzamide, as an oil. The compound contained 8% of N-(2-{1-[3-(1,1-dimethyl-2-phenoxyethylamino)propyl]imidazol-5-yl}ethyl)benzamide, by $^1$H nmr and $^{13}$C nmr. These compounds may be separated by HPLC.

EXAMPLE 77

3-[4-(2-Aminoethyl)imidazol-1-yl]-N-(1,1-dimethyl-2-phenoxyethyl)propylamine (2.05 g) was reacted with benzenesulphonyl chloride (1.15 g) in a similar manner to Example 55 to give N-(2-{1-[3-(1,1-dimethyl-2-phenoxyethylamino)propyl]imidazol-4-yl}ethyl]benzenesulphonamide, as an oil. The compound contained 7% of N-(2-{1-[3-(1,1-dimethyl-2-phenoxyethylamino)propyl]imidazol-5-yl}ethyl]benzenesulphonamide, by $^1$H nmr and $^{13}$C nmr. These compounds may be separated by HPLC.

EXAMPLE 78

A solution of benzoyl chloride (0.36 g) in dichloromethane (1.5 ml) was added dropwise to a mixture of 2-[3-(imidazol-1-yl)propylamino]-2-methyl-1-propanol (0.5 g) and triethylamine (0.5 g) in dichloromethane (5 ml) with stirring under nitrogen at 0° C. The mixture was stirred at 0° C. for 1 hour and then allowed to warm up to ambient temperature and stirred at this temperature for 3 hours. Saturated aqueous sodium bicarbonate (5 ml) was added. The mixture was shaken and the organic layer separated. The aqueous layer was extracted with further dichloromethane. The combined organic extracts were dried, filtered and evaporated to give an oil which was dissolved in ether and treated with ethereal hydrogen chloride to give 2-[3-(imidazol-1-yl)propylamino]-2,2-dimethylethyl benzoate dihydrochloride, m.p. 198–199° C., after recrystallisation from ethanol.

EXAMPLE 79

In a similar manner to Example 78, 2-[3-(imidazol-1-yl)propylamino3–2-methyl-1-propanol (1.0 g) was reacted with 4-chlorobenzoyl chloride (0.89 g) to give 2-[3-(imidazol-1-yl)propylamino]-2,2-dimethylethyl 4-chlorobenzoate dihydrochloride, m.p. 207–209° C.

EXAMPLE 80

A solution of 2-[3-(imidazol-1-yl)propylamino]-2-methyl-1-propanol (1.5 g) in dimethyl acetamide (10 ml) was added dropwise to a stirred suspension of sodium hydride (0.32 g of a 60% dispersion in mineral oil) in dimethyl acetamide (15 ml) at 30° C. under nitrogen. The mixture was stirred for 45 minutes at 30° C. and then a solution of 4-chlorobenzyl chloride (1.63 g) in dimethyl acetamide (5 ml) was added. After the addition, the mixture was heated at 100–105° C. for 30 minutes and then cooled to 25° C. Toluene (50 ml) was added and the mixture was washed with water. The toluene layer was extracted with 5M hydrochloric acid. The combined acid extracts were basified with concentrated sodium hydroxide solution with cooling and extracted with dichloromethane to give an oil which was distilled under high vacuum to give N-[2-(4-chlorobenzyloxy)-1,1-dimethylethyl]-3-(imidazol-1-yl)propylamine, b.p. 180–185° C. at 0.3 mbar.

EXAMPLE 81 a) A mixture of 1-(5-aminopentyl)imidazole (3.48 g), 3-phenylpropionaldehyde (3.08 g), p-toluenesulphonic acid (0.1 g) and toluene (90 ml) was boiled under reflux whilst removing the water formed using a Dean & Stark apparatus under nitrogen for 2 hours. The mixture was evaporated to dryness under reduced pressure to give an oil which was dissolved in IMS (100 ml) and cooled to 5° C. under nitrogen. Sodium borohydride (0.87 g) was added to the solution with stirring. The mixture was allowed to warm to 20° C. and stirred at this temperature for 16 hours. The solvent was removed under reduced pressure. The residue was dissolved in water and acidified to pH 2 with 2M hydrochloric acid. The solution was then basified with 2M sodium hydroxide solution (100 ml) and extracted with ethyl acetate to give an oil. The oil was distilled under high vacuum b.p. 250° C. at 0.04 mbar. The distillate was purified by flash column chromatography on silica using ethyl acetate/methanol/triethylamine (80:10:10) as the mobile phase to give N-(3-phenylpropyl)-5-imidazol-1-ylpentylamine 0.75 hydrate.

EXAMPLE 82 a) A mixture of N-[(-(4-chlorophenyl)-1-methylethyl]acrylamide (22.35 g), imidazole-4-carboxaldehyde (9.6 g), benzyltrimethylammonium hydroxide (2.24 ml of a 40% solution in methanol, Triton®B) and 1,4-dioxane (112 ml) was stirred and heated at 95° C. for 6 hours and then worked up as described in Example 19a to give N-[1-(4-chlorophenyl)-1-methylethyl]-3-(4-formylimidazol-1-yl)propionamide, m.p. 151–153° C.

b) A mixture of N-[1-(4-chlorophenyl)-1-methylethyl]-3-(4-formylimidazol-1-yl)propionamide (6.0 g) in absolute alcohol (160 ml) and N-butylamine (2.77 g) was stirred for 8 hours at ambient temperature and then left to stand at ambient temperature for 60 hours. The solvent was removed under reduced pressure and the residue recrystallised from cyclohexane/ethyl acetate (3:1) to give the imine (6.22 g) which was dissolved in absolute alcohol (53 ml) and then sodium borohydride (1.26 g) was added. The mixture was boiled under reflux for 16 hours. The solvent was removed under reduced pressure. Water was added to the residue and the mixture extracted with ethyl acetate to give a solid which was recrystallised from cyclohexane/ethyl acetate (5:1) to give 3-(4-butylaminomethylimidazol-1-yl)-N-[1-(4-chlorophenyl)-1-methylethyl]propionamide, m.p. 115–117° C.

c) A mixture of the amide from part b) (1.0 g), THF (20 ml) and borane THF (10.6 ml, 1 M solution) was boiled under reflux for 6 hours. The solvent was removed under reduced pressure and the residue dissolved in methanol. Concentrated hydrochloric acid was added until the solution reached pH 1. The mixture was boiled under reflux for 2 hours and then the methanol was removed under reduced pressure. The residue was dissolved in water and the solution washed with ethyl acetate. The aqueous layer was basified with 5 M sodium hydroxide and then extracted with ethyl acetate to give an oil which was dissolved in ether, filtered to remove a small amount of insoluble material which was discarded, and the filtrate evaporated to give an oil which was dried at 70° C. under high vacuum to give 3-[4-(butylaminomethyl)imidazol-1-yl]-N-[1-(4-chlorophenyl)-1-methylethyl]propylamine as an oil.

EXAMPLE 83

A mixture of 1-(4-chlorophenyl)-1-methylethylamine hydrochloride (2.7 g) was dissolved in 2M sodium hydroxide solution (50 ml) and the amine free base was extracted into diethyl ether to give an oil. This oil was dissolved in absolute ethanol (15 ml) and 2-formylimidazole (1.5 g) in absolute ethanol (20 ml) was added dropwise. The mixture was boiled under reflux for 4 hours and then left to stand at ambient temperature for 48 hours. Sodium borohydride (0.67 g) was added in portions to the solution and the mixture was boiled under reflux with stirring for 7 hours. The ethanol was removed under reduced pressure and water (40 ml) added to the residue. The mixture was filtered to give 1-(4-chlorophenyl)-N-(imidazol-2-ylmethyl)-1-methylethylamine, m.p. 164–165° C.

EXAMPLE 84 a) 3-[Imidazol-4(5)-yl]propionic acid (0.25 g, prepared as described in J.C.S. Perkin 1, 1984, 59) was dissolved in thionyl chloride (1.2 ml) with cooling. The mixture was left to stand at ambient temperature overnight and then excess thionyl chloride was removed under reduced pressure. Chloroform (7 ml) was added and the suspension cooled to 0° C. while triethylamine (1.18 ml) and 1-(4-chlorophenyl)-1-methylethylamine (0.72 g) were added. The mixture was boiled under reflux for 18 hours, then cooled and diluted with chloroform, washed with sodium carbonate solution, then dried and evaporated. The residue was purified by flash chromatography on silica using methanol as the mobile phase to give N-[1-(4-chlorophenyl)-1-methylethyl]-3-(imidazol-4(5)-yl)propionamide.

b) A mixture of the amide from a) (0.10 g), THF (10 ml) and borane/THF (1.4 ml) was boiled under reflux for 3 hours. The solvent was removed under reduced pressure and the residue heated on a steam bath for 1 hour. The mixture was cooled while 1 M hydrochloric acid (2 ml) was added and then heated on a steam bath for 1 hour. The mixture was cooled, diluted with water, washed with dichloromethane, basified with sodium bicarbonate and extracted with dichloromethane to give an oil which was purified by flash chromatography on silica using methanol as a mobile phase to give N-[1-(4-chlorophenyl)-1-methylethyl]-3-(imidazol-4(5)-yl)propylamine as an oil.

EXAMPLE 85 p a) Imidazol-4(5)-ylacetic acid (1.0 g) was added in portions to a stirred mixture of phosphorus pentachloride (1.26 g) and thionyl chloride (1.56 ml) at 60° C. The mixture was heated at 60–65° C. for 1.5 hours, cooled, diluted with chloroform and filtered to give the crude acid chloride. This acid chloride (0.5 g) was suspended in chloroform (11 ml) and cooled to 0° C. Triethylamine (1.95 ml) and 1-(4-chlorophenyl)-1-methylethylamine (1.2 g) were added and the mixture boiled under reflux for 18 hours. The mixture was cooled, diluted with chloroform and thoroughly mixed with sodium carbonate solution. The mixture was filtered and the organic layer was separated from the filtrate. The aqueous layer was extracted with ethyl acetate and the chloroform and ethyl acetate extracts were combined, dried and evaporated. The residue was triturated with ether to give N-[1-(4-chlorophenyl)-1-methylethyl]-2-(imidazol-4(5)-yl) acetamide, m.p. 186–187° C.

b) The product from a) (1.5 g), borane/THF (21.6 ml, 1.0 M solution) and THF (40 ml) was boiled under reflux for 3 hours. The mixture was worked up as described in Example 84b to give 1-(4-chlorophenyl)-2'-(imidazol-4(5)-yl)-1-methyldiethylamine as an oil.

EXAMPLE 86 a) A solution of diethyl malonate (57.8 g) in absolute ethanol (100 ml) was added to a stirred solution of sodium ethoxide in absolute ethanol (prepared from sodium (8.31 g) and absolute ethanol (150 ml)). The mixture was stirred at ambient temperature for 30 minutes. The mixture was cooled in ice water and a solution of 1-benzyl-2-chloromethylimidazole hydrochloride (25.0 g) in absolute ethanol (210 ml) was added over 30 minutes. The mixture was stirred at ambient temperature for 2 hours and then concentrated under reduced pressure. Ice cold 2 M hydrochloric acid (200 ml) was added to the residue and the solution washed with ethyl acetate. The aqueous layer was neutralised with sodium carbonate and extracted with ether to give a residue which was warmed at 95° C. for 18 hours with concentrated hydrochloric acid (100 ml). The mixture was evaporated to dryness to give 3-(1-benzylimidazol-2-yl)propionic acid hydrochloride as a glasslike product.

b) The suspension of the product from a) (15.8 g), 1,1'-carbonyldiimidazole (9.6 g), triethylamine (8.2 ml) and acetonitrile (150 ml) was stirred at ambient temperature for 3 hours. 1-(4-Chlorophenyl)-1-methylethylamine (10.05 g) was added and the mixture stirred at ambient temperature for 18 hours. The solvent was removed under reduced pressure and 2M sodium hydroxide solution was added. The organics were extracted into dichloromethane to give a residue which was recrystallised from ethyl acetate to give a solid which was discarded. The filtrate from the recrystallisation was evaporated to dryness and this residue was purified by flash column chromatography on silica using ethyl acetate/methanol, 9:1 as the mobile phase to give a solid which was recrystallised from ethyl acetate/petroleum ether, b.p. 60–80° C. (2:3) to give 3-(1-benzylimidazol-2-yl)-N-[1-(4-chlorophenyl)-1-methylethyl]propionamide, m.p. 128–129° C.

c) A mixture of the product from b) (2.88 g), borane/THF (30.2 ml, 1.0 M solution) and THF (50 ml) was heated at 95° C. for 3 hours. The mixture was worked up as described in Example 84b to give 3-(1-benzylimidazol-2-yl)-N-[1-(4-chlorophenyl)-1-methylethyl]propylamine as an oil.

EXAMPLE 87

A solution of the final product from Example 86 (200 mg) in dry THF (5 ml) was added to liquid ammonia (15 ml) (purified by treating the liquid ammonia with sodium and distilling the ammonia into another flask). The mixture was cooled in a dry ice acetone bath at −35° C., in a flask fitted with an acetone dry ice condenser, and small pieces of sodium were added until the blue colour persisted. After 15 minutes ammonium chloride (0.1 g) was added and the ammonia allowed to evaporate. Ethanol (10 ml) was added to the mixture followed by water (10 ml) and the solvent largely removed under reduced pressure. The residue was diluted with water and extracted with dichloromethane to give a residue which was purified by flash column chromatography on silica using methanol/ethyl acetate (1:1) as the mobile phase to give 3-(imidazol-2-yl)-N-(1-methyl-1-phenylethyl)propylamine as an oil.

EXAMPLE 88

A mixture of 5-chloroindanone (10.2 g, supplied by Lancaster Chemicals) and 1-(3-aminopropyl)imidazole (7.62 g) was heated at 90° C., while bubbling nitrogen through the molten mixture, for 2 hours. The mixture was cooled and dissolved in absolute ethanol (140 ml). Sodium borohydride (4.63 g) was added to the solution and the mixture boiled under reflux for 7 hours. The solvent was removed under reduced pressure. Water was added to the residue and the mixture was extracted with ethyl acetate to give an oil which was dissolved in ether and filtered. The filtrate was treated with ethereal hydrogen chloride to give a solid which was collected and recrystallised from propan-2-ol/ethanol/water (150 ml/150 ml/trace) (with a charcoal hot filtration) to give N-(5-chloroindan-1-yl)-3-(imidazol-1-yl)propylamine dihydrochloride, m.p. 251–254° C.

EXAMPLE 89 a) A mixture of N-{2-[4-(1-amino-1-methylethyl)phenyl] ethyl}-4-methoxybenzenesulphonamide (0.97 g), 3-(1- benzylimidazol-2-yl)propionaldehyde (0.66 g), 4A molecular sieves (0.7 g) and acetonitrile (15 ml) was stirred at ambient temperature for 18 hours. The mixture was filtered and the filtrate evaporated under reduced pressure to give a residue which was dissolved in absolute ethanol (15 ml). Sodium borohydride (0.18 g) was added to the ethanolic solution and the mixture was boiled under reflux for 3 hours. The solvent was removed under reduced pressure and water was added to the residue followed by dilute hydrochloric acid to give an acidic mixture. After 20 minutes the mixture was basified with dilute sodium hydroxide solution and extracted with ethyl acetate to give an oil which was purified with flash column chromatography on silica to give N-[2-(4-{1-[3-(1-benzylimidazol-2-yl)propylamino]-1-methylethyl}phenyl)ethyl]-4-methoxybenzenesulphonamide. A mixture of this product (0.61 g), absolute ethanol (30 ml), ammonium formate (0.42 g) and 10% palladium on carbon (0.91 g) was boiled under reflux for 1 hour. The mixture was filtered and the filtrate was evaporated under reduced pressure to give a residue which was purified by flash column chromatography on silica using ethyl acetate/methanol/triethylamine (18:1:1) as the mobile phase to give N-[2-(4-{1-[3-(imidazol-2-yl)propylamino]-1-methylethyl}phenyl)ethyl]-4-methoxybenzenesulphonamide as an oil.

The following examples were prepared by reacting 3-(1-benzylimidazol-2-yl)propionaldehyde with the appropriate amine, followed by reduction, by the method of Example 89:

EXAMPLE 90

N-(1-ethyl-1-phenylpropyl)-3-(imidazol-2-yl) propylamine as an oil; (The benzyl group was removed using sodium in liquid ammonia in a similar manner to Example 87.);

EXAMPLE 91

2-(4-(1-[3-(imidazol-2-yl)propylamino]-1-methylethyl) phenyl]ethanol as an oil;

EXAMPLE 92

4-{1-[3-(imidazol-2-yl)propylamino]-1-methylethyl}-N,N-dipropylbenzenesulphonamide as an oil;

EXAMPLE 93

3'-(imidazol-2-yl)-3-(2-methoxyphenyl)-1,1-dimethyldipropylamine as an oil;

EXAMPLE 94

3-(imidazol-2-yl)-N-(1,1-dimethyl-2-phenoxyethyl)-propylamine as an oil;

EXAMPLE 95

N-[2-(4-{1-[3-(imidazol-2-yl)propylamino-1-methylethyl}phenyl)ethyl]benzenesulphonamide as an oil;

EXAMPLE 96

2-ethyl-2-(4-{1-[3-(imidazol-2-yl)propylamino]-1-methylethyl}phenyl)butan-1-ol as an oil;

EXAMPLE 97

N-cyclohexyl-4-{1-[3-(imidazol-2-yl)propylamino]-1-methylethyl}benzamide as an oil;

EXAMPLE 98

1-[4-Benzyloxy-3-prop-2-enylphenyl]-1-methylethylamine was reacted with epichlorohydrin and then with imidazole following the method of Example 43 to give 1-[1-(4-benzyloxy-3-prop-2-enylphenyl)-1-methylethylamino]-3-(imidazol-1-yl)propan-2-ol which was hydrogenated in ethanol at atmospheric pressure using palladium on charcoal as catalyst to give 1-[1-(4-hydroxy-3-propylphenyl)-1-methylethylamino]-3-(imidazol-1-yl) propan-2-ol as an oil;

EXAMPLE 99

N-hexyl-4-{1-[3-(imidazol-2-yl)propylamino]-1-methylethyl}phenylacetamide (in the first step the reaction mixture was boiled under reflux for 3 hours);

The following examples are prepared by reacting 3-(1-benzylimidazol-2-yl)propionaldehyde with the appropriate amine, followed by reduction, by the method of Example 89:

EXAMPLE 100

4-{1-[3-(imidazol-2-yl)propylamino]-1-methylethyl}-2-propylphenol is prepared from 1-[4-benzyloxy-3-prop-2-enylphenyl]-1-methylethylamine;

EXAMPLE 101

2-(4-{1-[3-(imidazol-2-yl)propylamino]-1-methylethyl}phenyl)-N,2,2-triethylacetamide;

EXAMPLE 102

N-[2-(4-{1-[3-(imidazol-2-yl)propylamino]-1-methylethyl}phenyl)ethyl]-3,4-dimethoxybenzenesulphonamide;

EXAMPLE 103

4-{N-[2-(4-{1-[3-(imidazol-2-yl)propylamino]-1-methylethyl}phenyl)ethylsulphamoyl]}-N-methylbenzamide;

EXAMPLE 104

2-(4-{1-[3-(imidazol-2-yl)propylamino]-1-methylethyl}phenyl)-N-methylacetamide;

EXAMPLE 105

N-{1-[4-(hexylsulphonylmethyl)phenyl]-1-methylethyl}-3-(imidazol-2-yl)propylamine;

EXAMPLE 106

N-[2-(4-methoxyphenoxy)-1,1-dimethylethyl]-3-(imidazol-2 -yl) propylamine;

EXAMPLE 107

N-[1,1-dimethyl-2-(4-methylphenoxy)ethyl]-3-(imidazol-2-yl)propylamine.

The following examples were prepared in a similar manner to Example 24 by reacting 3-(imidazol-1-yl) propionaldehyde with the appropriate amine, followed by reduction and in certain cases salt formation:

EXAMPLE 108

N-[2-(4-methoxyphenoxy)-1,1-dimethylethyl]-3-(imidazol-yl)propylamine dihydrochloride hydrate m.p. 107–110° C.;

EXAMPLE 109

N-{1,1-dimethyl-2-[4-(4,5-dihydrothiazol-2-yl)phenoxy] ethyl}-3-(imidazol-1-yl)propylamine dimaleate, m.p. 125–128° C.;

EXAMPLE 110

N-hexyl-2-(4-{1-[3-(imidazol-1-yl)propylamino]-1-methylethyl}phenoxy)acetamide as an oil;

EXAMPLE 111

4-{1-[-3-(imidazol-1-yl)propylamino]-1-methylethyl}-N-pentylcinnamamide as an oil;

EXAMPLE 112

N-[2-(4-{1-[3-(imidazol-1-yl)propylamino]-1-methylethyl}phenyl) ethyl]-4-methoxybenzenesulphonamide as an oil;

EXAMPLE 113

2-ethyl-2-(4-{1-[3-(imidazol-1-yl)propylamino]-1-methylethyl}phenyl)butan-1-ol as an oil;

EXAMPLE 114

1-(4-{1-[3-(imidazol-1-yl)propylamino]-1-methylethyl}phenyl)-N-pentylmethanesulphonamide as an oil; and

EXAMPLE 115

N-[2-(4-{1-[3-(imidazol-1-yl)propylamino]-1-methylethyl}phenyl)ethyl]-3,4-dimethoxybenzenesulphonamide as an oil.

EXAMPLE 116

3-(4-{1-[3-(Imidazol-1-yl)propylamino]-1-methylethyl}phenyl)-N-pentylpropionamide was prepared by reducing the product of Example 111 with hydrogen in the presence of palladium on charcoal at atmospheric pressure in ethanol to give the product as an oil.

The following examples are prepared in a similar manner to Example 24 by reacting 3-(imidazol-1-yl)propionaldehyde with the appropriate amine, followed by reduction:

EXAMPLE 117

N-[1,1-dimethyl-2-(4-methylphenoxy) ethyl]-3-(imidazol-1-yl)propylamine;

EXAMPLE 118

1-(2-methoxy-5-{1-[3-(imidazol-1-yl)propylamino]-1-methylethyl}phenyl)pentanol;

EXAMPLE 119

N-[1-(4-methoxy-3-pentylphenyl)-1-methylethyl]-3-(imidazol-1-yl)propylamine;

EXAMPLE 120

4-{1-[3-(imidazol-1-yl)propylamino]-1-methylethyl}-2-pentylphenol;

EXAMPLE 121

2-(4-{1-[3-(imidazol-1-yl)propylamino]-1-methylethyl}-2-pentylphenyl)-N-methylacetamide;

EXAMPLE 122

N-(2-{1-[3-(1-ethyl-1-phenylpropylamino)-2-hydroxypropyl]imidazol-4-yl}ethyl)benzamide;

EXAMPLE 123

4-{N-[2-(4-{1-[3-(imidazol-1-yl)propylamino]-1-methylethyl}phenyl)ethyl]sulphamoyl}benzamide;

EXAMPLE 124

4-{N-[2-(4-{1-[3-(imidazol-1-yl)propylamino]-1-methyl-ethyl}phenyl)ethylsulphamoyl]}-N-methylbenzamide; and

EXAMPLE 125 methyl 4-{2-[3-(imidazol-1-yl)propylamino]-2-methyl-propoxymethyl}benzoate.

EXAMPLE 126

3,4-Dihydroxy-N-[2-(4-{1-[3-(imidazol-1-yl)propylamino]-1-methylethyl}phenyl)ethyl]benzenesulphonamide is prepared by reacting the product of Example 115 with hydrobromic acid;

EXAMPLE 127

3,4-Dihydroxy-N-[2-(4-{1-[3-(imidazol-2-yl)propylamino]-1-methylethyl}phenyl)ethyl]benzenesulphonamide is prepared by reacting the product of Example 101 with hydrobromic acid.

EXAMPLE 128

2-(4-{1-[3-(Imidazol-1-yl)propylamino]-1-methylethyl}-2-pentylphenoxy)-N-methylacetamide is prepared by reacting the product of Example 120 with N-methylchloroacetamide (prepared by reaction of methylamine with chloroacetyl chloride).

PHARMACEUTICAL EXAMPLES

EXAMPLE U

In the preparation of capsules, 10 parts by weight of active compound and 240 parts by weight of lactose are de-aggregated and blended. The mixture is filled into hard gelatin capsules, each capsule containing 10 mg active compound.

EXAMPLE V

Tablets are prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with magnesium stearate and the rest of the starch. The mixture is then compressed in a tableting machine to give tablets containing 10 mg of active compound.

EXAMPLE W

Tablets are prepared by the method of the previous Example. The tablets are enteric coated in a conventional manner using a solution of 20% cellulose acetate phthalate and 3% diethyl phthalate in ethanol:dichloromethane (1:1).

EXAMPLE X

In the preparation of suppositories, 100 parts by weight of active compound is incorporated in 1300 parts by weight of semi-synthetic glycerides as the suppository base and the mixture formed into suppositories each containing 100 mg of active ingredient.

EXAMPLE Y

In the preparation of capsules, 50 parts by weight of active compound, 300 parts by weight of lactose and 3 parts by weight of magnesium stearate are de-aggregated and blended. The mixture is filled into hard gelatin capsules, each capsule containing 50 mg of active ingredient.

EXAMPLE Z

The active compound is incorporated into the base by thorough homogenization until the drug is evenly distributed. The ointment is packed into 10 g amber jars with screw-capped lined lids.

Active compound 0.1 g

White soft paraffin to 10 g

PREPARATION OF STARTING MATERIALS

Starting materials, not detailed below, were commercially available and may be found by reference to the Fine Chemicals Directory or suppliers' catalogues.

NITRILES

N1 4-(2-Benzyloxyethyl)benzonitrile

This compound was prepared by alkylation of 4-(2-hydroxyethyl)benzonitrile with benzyl bromide in the presence of sodium hydride in THF initially at 0° C. and then at ambient temperature.

N2 4-Cyano-N-cyclohexylbenzamide

This compound was prepared by reacting 4-cyanobenzoic acid with a molar equivalent of cyclohexylamine in the presence of a molar equivalent of carbonyldiimidazole at ambient temperature in dichloromethane. The mixture was washed with dilute acid, then with dilute sodium hydroxide solution, dried and evaporated to give the product, m.p. 179–180° C. (from ethyl acetate).

N3 4-Cyanophenyl-N-hexylacetamide

This compound was prepared by reacting 4-cyanophenylacetic acid (prepared as described in J. Chem. Soc. 1941, 744) with hexylamine in a similar manner to N2.

N4 N-(4-Chlorobenzyl)-4-cyanophenylacetamide

This compound was prepared by reacting 4-cyanophenylacetic acid with 4-chlorobenzylamine in a similar manner to N2.

N5 4-Cyanophenyl-N-methylacetamide

This compound was prepared from 4-cyanophenylacetic acid and methylamine in a similar manner to N2.

N6 4-Methylthiophenoxyacetonitrile

This compound was prepared by alkylating 4-methylthiophenol with bromoacetonitrile in dry THF in the presence of sodium hydride.

N7 4-(4,4-Dimethyl-2-oxazolin-2-yl)benzonitrile

This compound was prepared by reacting 4-cyanobenzoyl chloride with 2-amino-2-methyl-1-propanol in the presence of thionyl chloride.

N9 4-(Dipropylaminosulphonyl)benzonitrile

This compound (m.p. 47–50° C.) was prepared by reacting 4-cyanobenzenesulphonyl chloride with dipropylamine.

N10 4'-Benzyloxybiphenyl-4-carbonitrile

This compound was prepared by reacting 4'-hydroxybiphenyl-4-carbonitrile with benzyl bromide in acetone in the presence of potassium carbonate.

N11 3-(2-Methoxyphenyl)propionitrile

This compound was prepared from 2-methoxybenzaldehyde following the method described in Org. Preparations and Procedures International 24, 673 (1992).

N12 4-Cyanophenyl-N-cycloheptylacetamide

This compound was prepared by reacting 4-cyanophenylacetic acid with cycloheptylamine in a similar manner to N2, to give the title compound, m.p. 179–180° C. (from ethyl acetate).

N13 4-(2-Aminoethyl)benzonitrile

A mixture of phthalimide (20.0 g) and triphenylphosphine (35.65 g) was added dropwise to a mixture of 4-(2-hydroxyethyl)benzonitrile (20.0 g) and diethylazodicarboxylate (21.4 ml) in THF (650 ml) with stirring over one hour. The mixture was stirred at ambient temperature for 4 days. The solvent was removed under reduced pressure. Methanol (500 ml) and hydrazine hydrate (13 ml) were added to the residue and the mixture was boiled under reflux with stirring for 5 hours. The solvent was removed under reduced pressure and aqueous acetic acid (420 ml of glacial acetic acid in 1030 ml of water) was added to the residue. This mixture was stirred for 1 hour and then filtered. The filtrate was added to ice and basified with solid potassium hydroxide. The mixture was extracted with dichloromethane to give an oil which was purified by flash column chromatography to give 4-(2-aminoethyl)benzonitrile, as an oil. A sample was dissolved in ethereal hydrogen chloride to give the hydrochloride salt, m.p. 211–213° C.

N14 N-[2-(4-Cyanophenyl)ethyl]-4-methoxybenzenesulphonamide

A mixture of 4-(2-aminoethyl)benzonitrile (3.0 g), 4-methoxybenzenesulphonyl chloride (4.24 g), dichloromethane (70 ml) and triethylamine (2.86 ml) were reacted to give the title compound.

N15 4-(1,1-Diethyl-2-hydroxyethyl)benzonitrile a) A suspension of 4-cyanophenylacetic acid (31.2 g, prepared as described in J.C.S. 744, (1941)), concentrated sulphuric acid (5 ml) and absolute ethanol (300 ml) was boiled under reflux with stirring for 48 hours. The solvent was removed under reduced pressure and dilute aqueous sodium hydroxide solution was added to neutralise the sulphuric acid. Dichloromethane was added. The mixture was filtered and extracted with further dichloromethane. The organic extracts were dried and evaporated to give ethyl 4-cyanophenylacetate, m.p. 94–95° C.

b) A solution of the product from part a) (8.0 g) in THF (40 ml) was added dropwise with stirring over 30 minutes to a suspension of sodium hydride (3.6 g. of a 60% dispersion in mineral oil) in dry THF (40 ml) at 60° C. under nitrogen. After the addition, the mixture was boiled under reflux for 2 hours with stirring, then cooled to 15° C. and a solution of iodoethane (7.3 ml) in THF (10 ml) was added dropwise over 15 minutes. The mixture was allowed to warm up to ambient temperature and stirred at this temperature for 18 hours. The mixture was cooled to 15° C. and carefully quenched with methanol (10 ml) and then water (60 ml). The solvent was removed under reduced pressure. The residue was diluted with water and extracted with ethyl acetate to give an oil which was distilled under high vacuum to give 2-(4-cyanophenyl)-2-ethylbutanoate, b.p. 140–155° C. at 0.06 mbar.

c) n-Butyllithium (0.82 ml, of a 2.5M solution in hexanes) was added dropwise with stirring to a solution of diisobutylaluminium hydride (2.04 ml of a 1.0 M solution in hexanes) in THF (4 ml) with cooling in an ice-water bath under nitrogen. The resulting solution was stirred for 30 minutes. A solution of the product from part b) (0.25 g) in THF (5 ml) was added to this solution at −78° C. under nitrogen with stirring. After stirring for 1 hour at −78° C. a solution of sodium borohydride (0.116 g) in absolute ethanol (10.2 ml) was added and the mixture allowed to warm to ambient temperature over 1 hour. The mixture was carefully hydrolysed by adding 10% aqueous hydrochloric acid dropwise with cooling. The mixture was concentrated under reduced pressure and extracted with ether to give an oil which is purified by flash column chromatography to give 4-(1,1-diethyl 2-hydroxyethyl)benzonitrile.

N16 4-[2-(Benzyloxy)ethyl]benzonitrile

This compound was prepared by reacting 4-(2-hydroxyethyl)benzonitrile with benzyl bromide in the presence of sodium hydride in THF.

N17 4-Benzyloxy-3-prop-2-enylbenzonitrile

This compound was prepared by reacting 4-hydroxy-3-prop-2-enylbenzonitrile (J.A.C.S. 1958, 3277) with benzyl bromide in the presence of acetone and potassium carbonate.

N18 N-[2-(4-Cyanophenyl)ethyl]benzenesulphonamide

The title compound was prepared by reacting 4-(2-aminoethyl)benzonitrile with benzenesulphonyl chloride in a similar manner to N14.

N19 1-(4-Cyanophenoxy)-N-hexylacetamide

Hexylamine was reacted with chloroacetyl chloride to give 1-chloro-N-hexylacetamide which was reacted with 4-hydroxybenzonitrile to give the title compound.

N20 4-Cyano-N-pentylbenzylsulphonamide

4-Bromomethylbenzonitrile was reacted with sodium sulphite followed by phosphorus pentachloride to give 4-cyanobenzylsulphonyl chloride which was reacted with pentylamine in a similar manner to N14 to give the title compound.

N21 4-Cyano-N-pentylcinnamamide

4-Cyanocinnamic acid was converted into the acid chloride and reacted with pentylamine to give the title compound.

N22 4-Hydroxy-3-(l-hydroxypentyl)benzonitrile

This compound was prepared by reacting 4-hydroxybenzonitrile with valeryl chloride in the presence of triethylamine to give 4-cyanophenyl valerate which was subjected to a Fries rearrangement with aluminium chloride to give 4-hydroxy-3-valerylbenzonitrile which was reduced with sodium borohydride to give the title compound.

N23 N-[2-(4-Cyanophenyl)ethyl]-3,4-dimethoxy benzenesulphonamide

This compound was prepared by reacting 4-(2-aminoethyl)benzonitrile with 3,4-dimethoxybenzenesulphonyl chloride.

PREPARATION OF AMINES (VII)

EXAMPLE A1

Method 1 a) Sodium (26.7 g) was dissolved in methanol (600 ml) and the solution cooled to −45° C. Bromine (65.3 g) was added dropwise with vigorous stirring while keeping the temperature −45° C. Once the colour had discharged, a solution of 2-methyl-2-(p-tolyl)propionamide (69.3 g) in 1,4-dioxane (257 ml) and methanol (350 ml) was added slowly over 20 minutes at −45° C. The mixture was allowed to warm up gradually to 20° C. whereupon an exotherm occurred which raised the temperature to 50° C. The exotherm was controlled by external cooling. The mixture was then boiled under reflux for 4.5 hours and the solvent removed under reduced pressure. The residue was diluted with 5 M sodium hydroxide solution and extracted with ether to give methyl N-[1-methyl-1-(p-tolyl)ethyl]carbamate, m.p. 42–43° C.

b) A mixture of the carbamate from a) (4.0 g), N-bromosuccinimide (3.8 g), carbon tetrachloride (80 ml) and azobisisobutyronitrile (0.12 g) was boiled under reflux for 18 hours. The mixture was cooled, washed with water, dried, filtered and the solvent removed by distillation under reduced pressure to give methyl N-[1-(4-bromomethylphenyl)-1-methylethyl]carbamate, m.p. 74–76° C.

c) A solution of potassium cyanide (24.4 g) in water (70 ml) was added dropwise over 20 minutes at 50° C. to a mixture of a product from part b) (60.0 g) in acetonitrile (500 ml). The mixture was boiled under reflux for 1 hour and then the solvent removed under reduced pressure. The residue was diluted with water and extracted with ether to give a residue which was recrystallised from petroleum ether, b.p. 60–80° C./propan-2-ol to give methyl N-[1-(4-cyanomethylphenyl)-1-methylethyl]carbamate, m.p. 88–90° C.

d) Trimethylsilyl iodide (24.0 g) was added over 5 minutes to a solution of the product from part c) (28.0 g) in chloroform (200 ml) with stirring under nitrogen at ambient temperature. The mixture was stirred at 60° C. for 2.5 hours then cooled in ice/water, quenched with saturated methanolic hydrogen chloride (20 ml) and stirred at ambient temperature for a further hour. The solvent was removed under reduced pressure and the residue diluted with ether (250 ml) and stirred at ambient temperature for 64 hours. The mixture was filtered to give 4-(1-amino-1-methylethyl)phenyl-acetonitrile.

EXAMPLE A2

Method 2 a) A solution of 4-chlorophenylacetonitrile (70 g) in dry THF (50 ml) was added with stirring to a suspension of sodium hydride (39.7 g, 60% dispersion) in boiling THF (100 ml) under reflux, under nitrogen at a rate such that boiling was maintained without heating the flask. After the addition the mixture was boiled under reflux for 2 hours. More THF (100 ml) was added and the mixture cooled to 10° C. A solution of iodomethane (139 g) in THF (50 ml) was added dropwise to the mixture over 2 hours whilst keeping the temperature below 10° C. The mixture was stirred at ambient temperature for 18 hours then kept below 10° C. while methanol (30 ml) was added dropwise, followed by water (150 ml). The mixture was allowed to warm up to ambient temperature and then concentrated under reduced pressure to remove the THF. The residue was diluted with water and extracted with dichloromethane. The combined extracts were dried and evaporated to give an oil which was distilled under vacuum to give 2-(4-chlorophenyl)-2-methyl-propionitrile, b.p. 90–94° C. (0.7 mbar).

b) A solution of the propionitrile (10 g), from part (a) above, in IMS (30 ml) was treated with a solution of sodium hydroxide (0.67 g) in water (3.3 ml). The mixture was warmed to 50° C. and hydrogen peroxide (14 ml, 60% w/v) was added dropwise with stirring. The mixture was stirred at ambient temperature for 3 hours and then evaporated to dryness under reduced pressure. The residue was partitioned between ethyl acetate and water. The mixture was separated and the aqueous layer extracted with ethyl acetate. The combined organic layers were washed with water, dried and evaporated to give 2-(4-chlorophenyl)-2-methylpropionamide, m.p. 125° C.

c) A boiling solution of the amide from (b) (68.3 g) in acetonitrile (500 ml) was added in one portion to a warm (approx. 50° C.) stirred suspension of hydroxy(tosyloxy) iodobenzene (165.3 g) in acetonitrile (800 ml). The resulting exotherm was controlled by external cooling. The mixture was boiled under reflux with vigorous stirring for 1 hour. The solvent was removed under reduced pressure and the residue mixed thoroughly with ethyl acetate (500 ml) and water (500 ml). The solid was collected by filtration through a filter agent (95% silicon dioxide, acid washed, Celite® 521). The solid was scraped off the surface of the filter agent and added to hot water (150 ml) to form a suspension which was basified with solid sodium hydroxide with external cooling. This mixture was extracted with diethyl ether and the combined extracts dried over magnesium sulphate and filtered. The filtrate was acidified with ethereal hydrogen chloride and the solid formed was collected by filtration and recrystallised from aqueous acetonitrile to give 1-(4-chlorophenyl)-1-methylethylamine hydrochloride, m.p. 246° C.

EXAMPLE A3

α,α-Diethylbenzylamine was prepared by reacting phenylacetonitrile with iodoethane according to Method 2.

EXAMPLE A4 a) 4-(Benzyloxy)phenylacetonitrile (74.35 g) was reacted with sodium hydride (28.6 g) in THF (300 ml) and then with iodomethane (100.3 g) in THF (35 ml) to give 2-(4-benzyloxyphenyl)-2-methylpropionitrile, m.p. 51–52° C.

b) The product from a) (2.0 g) was dissolved in IMS (10 ml) and treated with sodium hydroxide (0.095 g in 0.47 ml $H_2O$) and 60% hydrogen peroxide (2.0 ml) to give 2-(4-benzyloxyphenyl)-2-methylpropionamide, m.p. 150–151° C.

c) The amide from b) (5.0 g) in acetonitrile (45 ml) was treated with a suspension of hydroxy (tosyloxy)iodobenzene (8.9 g) in acetonitrile (25 ml) to give 1-(4-benzyloxyphenyl)-l-methylethylamine hydrochloride, m.p. 223–224° C.

EXAMPLE A5

Method 3

Cerium (III) chloride heptahydrate (50 g) was dried under vacuum (0.52 mbar) at 150–160° C. for 7 hours and then allowed to cool under nitrogen. The flask was cooled to 0° C. and dry THF (230 ml) added with stirring. The suspension was stirred at ambient temperature for 1 hour, then cooled to –68° C. and a solution of methyllithium in THF (96.0 ml, 1.4 M solution) was added slowly, keeping the temperature below –60° C. The mixture was stirred at –60° C. to –70° C. for 30 minutes and then a solution of 4-chlorophenoxyacetonitrile (7.4 g) (supplied by Lancaster Chemicals) in dry THF (30 ml) was added over 20 minutes, keeping the temperature below –68° C. The mixture was allowed to warm up to –5° C. over 2 hours and then stirred at this temperature for 1.5 hours. Concentrated aqueous ammonia solution (58 ml, SG 0.880) was added carefully. The mixture was filtered and the residue washed with THF and then with dichloromethane. The filtrate and the THF washings were evaporated to dryness and the dichloromethane washings added to the residue. This solution was washed with water, dried and evaporated to give an oil which was dissolved in ether and treated with ethereal hydrogen chloride to give 2-(4-chlorophenoxy)-1,1-dimethylethylamine hydrochloride.

The following were prepared in a similar manner:

A6 1-[4-(2-Benzyloxyethyl)phenyl]-1-methylethylamine (from N1);

A7 4- (-Amino-1-methylethyl)--N-cyclohexylbenzamide (from N2);

A8 4-(l-Amino-1-methylethyl)phenyl-N-hexylacetamide (from N3);

A9 4-(1-Amino-1-methylethyl)phenyl-N-(4-chlorobenzyl) acetamide (from N4);

A10 4-(1-Amino-1-propylbutyl)phenyl-N-methylacetamide (from N5);

A11 1,1-Dimethyl-2-(4-methylthiophenoxy)ethylamine hydrochloride, m.p. 236–237° C. (from N6);

A12 2-[4-(4,4-Dimethyl-2-oxazolin-2-yl)phenyl]-1-methylethylamine (from N7);

A13 5-(1-Amino-1-methylethyl)-2-chloroaniline (from 3-amino-4-chlorobenzonitrile (Apin);

A14 4-(1-Amino-l-methylethyl)-N,N-dipropylbenzene-sulphonamide (from N9);

A15 1-(4'-Benzyloxybiphenyl-4-yl)-1-methylethylamine (from N10);

A16 3-(2-Methoxyphenyl)-1,1-dimethylpropylamine hydrochloride, m.p. 130–131° C. (from N11);

A17 4-(1-Amino-1-methylethyl)phenyl-N-cycloheptyl-acetamide (from N12);

A18 4-(1-Amino-1-methylethyl)phenethylamine (from N13).

A19 N-{2-[4-(1-Amino-1-methylethyl)phenyl]ethyl}-4-methoxybenzenesulphonamide (from N14);

A20 2-[4-(1-Amino-1-methylethyl)phenyl]-2-ethylbutan-1-ol (from N15);

A21 2-(4-Fluorophenoxy)-1,1-dimethylethylamine from 4-fluorophenoxyacetonitrile (prepared by alkylation of 4-fluorophenol with chloroacetonitrile in butan-2-one in the presence of potassium carbonate under reflux);

A22 1-[4-(2-Benzyloxyethyl)phenyl]-1-methylethylamine was prepared from N16;

A36 1-[4-Benzyloxy-3-prop-2-enylphenyl]-1-methylethylamine was prepared (from N17);

A37 N-{2-[4-(1-Amino-1-methylethyl)phenyl]ethyl}4-benzenesulphonamide (from N18);

A38 4-(1-Amino-1-methylethyl)phenoxy-N-hexylacetamide (from N19);

A39 4-(1-Amino-1-methylethyl)benzyl-N-pentylsulphonamide (from N20);

A40 4-(1-Amino-1-methylethyl)-N-pentylcinnamamide (from N21);

A41 2-[4-(4,5-Dihydrothiazol-2-yl)phenoxy]-1,1-dimethylethylamine from 4,5-dihydrothiazol-2-yl) phenoxyacetonitrile (supplied by Maybridge Chemical Co.);

A42 2-(4-Methoxyphenoxy)-1,1-dimethylethylamine from 4-methoxyphenoxyacetonitrile;

A43 4-(1-Amino-1-methylethyl)-3-(1-hydroxypentyl) phenol (from N22); and

A44 N-[2-[4-(1-Amino-1-methylethyl)phenyl]ethyl)-3,4-dimethoxybenzenesulphonamide (from N23).

In the preparation of the above compounds if there is no oxygen atom between the phenyl ring and the nitrogen, then after the addition of the nitrile the mixture was allowed to warm up to ambient temperature and then stirred at that temperature for 16 hours. In certain cases the step forming the hydrochloride salt was omitted as is obvious from the compound name.

EXAMPLE A23

Method 4 a) A solution of 4-chlorophenylthioacetonitrile (57.6 g) in dry THF (200 ml) was added dropwise to a stirred suspension of sodium hydride (27.1 g, 60% dispersion in mineral oil) in dry THF (200 ml) under nitrogen with boiling under reflux. The mixture was boiled under reflux for 3 hours, then cooled to 15° C. and a solution of iodomethane (94.8 g) in dry THF (35 ml) was added dropwise whilst maintaining the temperature at 15–20° C. The mixture was stirred at ambient temperature for 18 hours and then quenched by successively adding methanol (35 ml) and water (100 ml). The THF was distilled off, the residue diluted with water and then extracted with ethyl acetate to give an oil which was distilled under vacuum to give crude 2-(4-chlorophenylthio)-2-methylpropionitrile, b.p. 77–80° C. at 0.3 mbar (product approximately 74% pure). This material was used directly in b).

b) A solution of the crude nitrile from a) (27.0 g) in dry THF (320 ml) was added dropwise to a stirred suspension of lithium aluminium hydride (7.32 g) in dry THF (500 ml) under nitrogen. The mixture was then stirred and boiled under reflux for 5 hours, then cooled and quenched by the dropwise addition of water (13 ml), 5M sodium hydroxide solution (26 ml) and finally with more water (26 ml). The mixture was stirred at ambient temperature for 30 minutes and then filtered. The filtrate was evaporated to dryness and the residue dissolved in ether, treated with ethereal hydrogen chloride and filtered to give a solid which was recrystallised from acetonitrile to give 2-(4-chlorophenylthio)-2-methylpropylamine hydrochloride, m.p. 167–168° C.

EXAMPLE A24

Method 5 a) A solution of 4-chlorothiophenol (64.8 g), 2-amino-2-methylpropanol (39.8 g) and toluene (160 ml) was treated with propionic acid (33.2 g) and the mixture boiled under reflux for 24 hours, collecting the water formed using a Dean and Stark apparatus. The mixture was dissolved in dichloromethane, washed with saturated sodium bicarbonate solution, dilute sodium hydroxide solution and then water. The organic layer was dried, filtered and evaporated to give an oil which was dried under high vacuum at 70° C. The oil, which solidified on standing, was dissolved in ether and treated with ethereal hydrogen chloride to give N-[2-(4-chlorophenylthio)-1,1-dimethylethyl]propionamide.

b) The amide from part a) (20.0 g) and concentrated hydrochloric acid (170 ml) were stirred and boiled under reflux for 3 days. The mixture was cooled and diluted with water and then washed with dichloromethane. The organic layer was dried, filtered and evaporated to give an oil. The oil was triturated with ethyl acetate/triethylamine (9:1) and filtered. The solid collected was discarded. The filtrate was passed through a silica pad using ethyl acetate/triethylamine (9:1) as a mobile phase to give 2-(4-chlorophenylthio)-1,1-dimethylethylamine.

EXAMPLE A25

(Method as in Method 5)

A mixture of 4-chloro-2,5-dimethylbenzenethiol (17.25 g), 2-amino-2-methylpropanol (8.9 g), propionic acid (7.4 g) and toluene (50 ml) was reacted to give a solid which was recrystallised from petroleum ether, b.p. 60–80° C. to give N-[2-(4-chloro-2,5-xylylthio)-1,1-dimethylethyl] propionamide, m.p. 78–81° C. This product (15.0 g) and concentrated hydrochloric acid (18 ml) were boiled under reflux for 25 hours give an oil which was purified by flash column chromatography on silica using ethyl acetate and then ethyl acetate/methanol (4:1) as the mobile phase to give 2-(4-chloro-2,5-xylylthio)-1,1-dimethylethylamine as an oil.

EXAMPLE A26

2-(4-tert-Butylphenylthio)-1,1-dimethylethylamine was prepared from 4-tert-butylthiophenol in a similar manner to Example A17.

EXAMPLE A27

Method 6 a) A solution of 1-hexanethiol (4.89 g) in DMF (15 ml) was added to a suspension of sodium hydride (1.66 g, 60% dispersion in mineral oil) in DMF (35 ml) over 15 minutes with stirring under nitrogen. The mixture was stirred at ambient temperature for 3 hours and then heated on a steam bath for 15 minutes. A solution of methyl N-[1-(4-bromomethylphenyl)-1- methylethyl]-carbamate (11.85 g) in DMF (50 ml) was added to this mixture, dropwise, over 10 minutes, at 20° C., with stirring. The mixture was stirred at ambient temperature for 18 hours and then quenched with saturated potassium carbonate solution (100 ml). The mixture was diluted with water and extracted with ether to give methyl N-[1-(4-hexylthiomethylphenyl)-1-methylethyl] carbamate as an oil.

b) Trimethylsilyl iodide (6.6 g) was added dropwise over 5 minutes to a solution of the product from a) (12.58 g) in chloroform (65 ml) with stirring under nitrogen at ambient temperature. The mixture was stirred at 60° C. for 2.5 hours then cooled to ambient temperature and quenched with saturated methanolic hydrogen chloride (10 ml). The mixture was stirred for 1 hour and then the solvent was removed under reduced pressure. The residue was diluted with water and ether added. A solid was present at the interface. The top organic layer was discarded and the solid and the aqueous layer were basified with sodium hydroxide solution and extracted with ether to give 1-(4-hexylthiomethylphenyl)-1-methylethylamine as an oil which was stored under nitrogen.

EXAMPLE A28 a) A solution of 3,4-dimethylbenzenethiol (9.24 g) in DMF (30 ml) reacted with a solution of methyl N-[1-(4-bromomethylphenyl)-1-methylethyl]carbamate (19.15 g) in DMF (100 ml) by Method 6a) to give methyl N-{1-methyl-1-[4-(3,4-xylylthiomethyl)phenyl]ethyl}carbamate as a sticky solid.

b) 3-Chloroperbenzoic acid (15.4 g) was added over a period of 15 minutes, in portions, to a solution of the product from a) (22.7 g) in dichloromethane (425 ml) with stirring at 0° C. The mixture was stirred at 0° C. for 40 minutes and three further portions of 3-chloroperbenzoic acid (15.4 g each) were added in a similar manner. The mixture was stirred for 1 hour at ambient temperature and then washed with dilute sodium hydroxide solution, brine, dried and evaporated. Ether (350 ml) was added to the residue and this mixture was stirred at ambient temperature overnight. The solid was collected by filtration and dried to give methyl N-{1-methyl-1-[4-(3,4-xylylsulphonylmethyl)phenyl] ethyl}-carbamate, m.p. 146–149° C. This product was reacted with trimethylsilyl iodide (0.23 ml) according to Method 6b to give 1-methyl-1-[4-(3,4-xylylsulphonylmethyl)-phenyl]ethylamine, m.p. 129–130° C.

EXAMPLE A29

3-Chloroperbenzoic acid (11.95 g) was added over a period of 15 minutes to a solution of methyl N-{1-[4-(hexylthiomethyl)phenyl]-1-methylethyl}carbamate (16.6 g prepared as described in Example A27a) in dichloromethane (330 ml) at 0C with stirring. The mixture was stirred at 0° C. for 40 minutes and then three further portions of 3-chloroperbenzoic acid (11.95 g each) were added as described above at 40 minute intervals. The mixture was stirred at ambient temperature for 1 hour then washed with dilute sodium hydroxide, water, dried and evaporated to give a residue which was stirred with ether (250 ml) at ambient temperature overnight, then filtered to give methyl N-{1-[4-(hexylsulphonylmethyl)-phenyl]-1-methylethyl}carbamate, m.p. 104–105° C. This product (8.08 g) reacted with trimethylsilyl iodide (5.5 g) according to Method 6b) to give 1-[4-(hexylsulphonylmethyl)phenyl]-1-methylethylamine as an oil. A small sample was dissolved in ether and acidified with ethereal hydrogen chloride to give the hydrochloride, m.p. 156–157° C.

MISCELLANEOUS AMINES VII

EXAMPLE A30 a) A mixture of phenol (33.2 g) and 2,4,4-trimethyloxazoline (18.1 g) was heated in a stirred pressure vessel at 220° C. for 48 hours. The oil obtained on cooling was dissolved in ethyl acetate, washed with 5M sodium hydroxide solution, water, brine, then dried and evaporated to give an oil which was distilled under high vacuum to give N-(1,1-dimethyl-2-phenoxyethyl)acetamide, b.p. 115–122° C. at 0.67 mbar.

b) A mixture of the acetamide from Part a) (27.6 g) and dilute hydrochloric acid (75 ml concentrated acid and 75 ml water) was boiled under reflux for 18 hours. The mixture was cooled and washed with-ethyl acetate. The aqueous layer was cooled to 0° C. and basified with 10M sodium hydroxide solution. The mixture was extracted with ethyl acetate to give a yellow oil which was distilled under high vacuum to give 1,1-dimethyl-2-phenoxyethylamine, b.p. 110–115° C. at 6.5 mbar.

EXAMPLE A31

4-(2-Bromoethoxy)benzonitrile (7.3 g) was reacted with potassium phthalimide (5.98 g) in DMF (35 ml) by heating at 95° C. for 3 hours. The N-[2-(4-cyanophenoxy) ethyl] phthalimide obtained after extractive workup (7.30 g) was suspended in IMS (350 ml) and treated with hydrazine hydrate (6.25 g). The mixture was stirred for 22 hours and filtered. The solid obtained was washed with IMS and the combined filtrate and washings were evaporated to dryness. Water was added to this residue and the mixture basified with 10M sodium hydroxide solution. The mixture was extracted with dichloromethane to give 4-(2-aminoethoxy) benzonitrile as an oil.

EXAMPLE A32

3,4'-Dichloropropiophenone was treated with potassium phthalimide, the product treated with ethylene glycol and then this product cleaved with hydrazine hydrate following the methods described in J. Org. Chem. 1972, 221–225, to give 2-[2-(4-chlorophenyl)-1,3-dioxolan-2-yl]ethylamine.

EXAMPLE A33

2-(4-Trifluoromethylphenoxy)-1,1-dimethylethylamine was prepared by reacting 4-chlorobenzotrifluoride with a mixture of sodium hydride and 2-amino-2-methylpropan-1-ol in dimethylacetamide at 110° C.

EXAMPLE A34

4-(1-Amino-1-methylethyl)phenethylamine (A18, 2.132 g) was treated with 4-cyanophenylsulphonyl chloride (2.63 g) in dichloromethane (35 ml) and triethylamine (1.8 ml) to give N-{2-[4-(1-amino-1-methylethyl)phenyl]ethyl}-4-cyanobenzenesulphonamide, as an oil.

AMINES OF FORMULA V a) Potassium phthalimide (92.5 g) was added in six portions over 4 hours to a boiling solution of 1,5-dibromopentane (230 g) in acetone (670 ml). The mixture was boiled under reflux for 24 hours, then cooled and filtered. The filtrate was evaporated to dryness and the residue dissolved in petroleum ether, b.p. 60–80° C./ethyl acetate (1:1) and the solution filtered. The filtrate was evaporated to dryness and the residue washed with several portions of petroleum ether, b.p. 60–80° C. to remove excess dibromopentane. The remaining oil was dried under vacuum at 50° C. The petrol washings were evaporated to dryness and distilled under vacuum to give recovered dibromopentane and a second fraction b.p. 86–120° C. at 17 mbar. This fraction solidified on cooling and scratching. A little of this solid was used to seed the remaining oil and the combined solids were recrystallised from absolute ethanol (300 ml) to give N-(5-bromopentyl)phthalimide, m.p. 62–63° C.

b) A solution of imidazole (9.66 g) in dry DMF (20 ml) was added dropwise to a stirred suspension of sodium hydride (5.7 g, 60% dispersion in mineral oil) in dry DMF (200 ml) at ambient temperature under nitrogen. The mixture was stirred at ambient temperature for 1.5 hours and then N-(5-bromopentyl)phthalimide (40 g) was added in portions to the mixture. The mixture was stirred at 95° C. for 16 hours and then the DMF removed under vacuum. The residue was extracted with toluene. The toluene extracts were cooled and a solid was collected by filtration and discarded. The filtrate was evaporated to dryness and the residue triturated with petroleum ether, b.p. 40–60° C. and then with ether to give an oil which was dried under vacuum at 50° C. and used directly in c).

c) The solution of phthalimide from b) (29.3 g) in IMS (830 ml) was treated with hydrazine hydrate (31 g) and the mixture stirred at ambient temperature for 24 hours. The mixture was filtered and the filtrate evaporated to dryness. The residue was partitioned between 10 M sodium hydroxide solution and dichloromethane. The basic layer was extracted twice with dichloromethane and the combined organic extracts were washed with brine, dried and evaporated to give 5-(imidazol-1-yl)pentylamine as an oil.

PREPARATION OF ACRYLAMIDES (XVI) Method 7

Acryloyl chloride (0.88 g) was added dropwise with stirring to a solution of 1-(4-chlorophenyl)-1-methylethylamine hydrochloride (2.0 g) (A2) and triethylamine (2.07 ml) in dichloromethane (10 ml) at −15 to −20° C. under nitrogen. After the addition, the mixture was stirred at ambient temperature for 2.5 hours. The mixture was diluted with 5M sodium hydroxide solution and then with water. The dichloromethane layer was separated, dried and evaporated to give N-[l-(4-chlorophenyl)-1-methylethyl] acrylamide, m.p. 114–117° C. (m.p. 122–123° C. after recrystallisation).

The following were prepared by Method 7 (the amine precursor is indicated in brackets):

N-[2-(4-chlorophenoxy)-1,1-dimethylethyl]acrylamide (from A5);

N-[2-(4-chlorophenylthio)-2-methylpropyl]acrylamide, m.p. 95–96° C. (from A23);

N-[2-(4-chlorophenylthio)-1,1-dimethylethyl]acrylamide (from A24);

N-[2-(4-chloro-2,5-xylylthio)-1,1-dimethylethyl]-acrylamide (from A25);

N-[2-(4-tert-butylphenylthio)-1,1-dimethylethyl]acrylamide (from A26);

4-Chloro-α,α-dimethylphenethylamine hydrochloride (17.2 g, prepared as described in Il Farmaco, 15, 337 (1960)) gave N- (4-chloro-α,α-dimethylphenethyl) acrylamide, m.p. 132.5–133.5° C.;

N-(1-ethyl-1-phenylpropyl)acrylamide (from A3);

N-(1,1-dimethyl-2-phenoxyethyl)acrylamide (from A30);

N-{1-[4-(cyanomethyl)phenyl]-1-methylethyl}acrylamide (from A1).

Preparation of Miscellaneous Starting Materials

4-{1-[3-(Imidazol-1-yl)propylamino]-1-methylethyl}phenol a) 1-(4-Benzyloxyphenyl)-1-methylethylamine hydrochloride (25.0 g) was treated with acryloyl chloride (8.43 ml) in dichloromethane (250 ml) containing triethylamine (14.4 ml) to give N-[1-(4-benzyloxyphenyl)-1-methylethyl]acrylamide, m.p. 116°117° C.

b) The product from a) (26.23 g), imidazole (6.65 g), benzyltrimethylammonium hydroxide (2.0 ml, 40% solution in methanol Triton®B) and 1,4-dioxane (250 ml) gave N-[1-(4-benzyloxyphenyl)-1-methylethyl]-3-(imidazol-1-yl)propionamide, m.p. 187–189° C. (Method as Example 17a).

c) The propionamide from b) (3.0 g) was reduced in THF (70 ml) with borane/THF (32.9 ml, 1.0 M solution) to give N-(l-(4-benzyloxyphenyl)-1-methylethyl]-3-(imidazol-1-yl)propylamine dihydrochloride, m.p. 186–187° C. (Method as Example 17b).

d) The product from c) (2.39 g) was dissolved in IMS (30 ml) and reduced by hydrogen in the presence of palladium charcoal (catalytic amount) at atmospheric pressure to give 4-{1-[3-(imidazol-1-yl)propylamino]-1-methylethyl}phenol as an oil.

N-{1-[4-(2-Aminoethyl)phenyl]-1-methylethyl}-3-(imidazol-1-yl)propylamine (Method as Example 17).

a) A mixture of N-{1-[4-(cyanomethyl)phenyl]-1-methylethyl}acrylamide (20.5 g), imidazole (6.11 g), benzyltrimethylammonium hydroxide (74 mg) and 1,4-dioxane (300 ml) gave N-{1-[4-(cyanomethyl)phenyl]-1-methylethyl}-3-(imidazol-1-yl)propionamide as an oil.

b) The amide from part a) (1.0 g), borane/THF (20.3 ml, 1.0 M solution) and THF (20 ml) was boiled under reflux for 4.5 hours and then worked up to give N-{1-[4-(2-aminoethyl)phenyl]-1-methylethyl}-3-(imidazol-1-yl)propylamine as an oil.

N-[2-(4-Tert-butylphenylthio)-1,1-dimethylethyl]-3-(imidazol-1-yl)propylamine N-[2-(4-tert-butylphenylthio)-1,1-dimethylethylacrylamide was reacted with imidazole and reduced with borane in a similar manner to Example 17 to give N- [2-(4-tert-butylphenylthio)-1,1-dimethylethyl]-3-(imidazol-1-yl)propylamine dihydrochloride, m.p. 202° C.

N-[1-(3-Amino-4-chlorophenyl)-1-methylethyl]-3-(imidazol-1-yl)propylamine

In a similar manner to Example 24, A13 (0.86 g) was reacted with 3-(imidazol-1-yl)propionaldehyde (0.64 g) to give N-[1-(3-amino-4-chlorophenyl)-1-methylethyl]-3-(imidazol-1-yl)propylamine as an oil.

3-[4-(2-Aminoethyl)-imidazol-1-yl]-N-(1-ethyl-1-phenylpropyl)propylamine a) In a similar manner to Example 24, N-(l-ethyl-1-phenylpropyl)acrylamide (6.1 g) and 4-cyanomethylimidazole (3.0 g, Sigma Chemicals) were reacted in 1,4-dioxane (60 ml) in the presence of Triton B (0.8 ml) to give 3-[4-(cyanomethyl)imidazol-1-yl]-N-(1-ethyl-1-phenylpropyl)propionamide, m.p. 121–122° C.

b) The product from part a) (4.95 g) was reduced with borane/THF (61 ml, 1M solution) in THF (110 ml) in a similar manner to Example 17b to give 3-[4-(2-aminoethyl)-imidazol-1-yl]-N-(1-ethyl-1-phenylpropyl)propylamine, as an oil.

3- [4-(2-Aminoethyl)imidazol-1-yl]-N-(1,1-dimethyl-2-phenoxyethyl)propylamine The title compound was prepared in a similar manner to the Example immediately above from N-(1,1-dimethyl-2-phenoxyethyl)acrylamide and 4-cyanomethyl-imidazole.

N-[1-(4'-Benzyloxybiphenyl-4-yl)-1-methylethyl)-3-(imidazol-1-yl)propylamine In a similar manner to Example 24, 1-(4'-benzyloxybiphenyl-4-yl)-1-methylethylamine (A15) (1.4 g) and 3-(imidazol-1-yl)propionaldehyde (0.72 g) were reacted to give N-[1-(4'-benzyloxybiphenyl-4-yl)-1-methylethyl)-3-(imidazol-1-yl)propylamine, m.p. 93–95° C.

3-(1-Benzyl-1H-imidazol-2-yl)propionaldehyde a) Diethyl malonate (52.45 g) in ethanol (50 ml) was added dropwise to a solution of sodium (11.3 g) in dry ethanol (300 ml) with stirring. The mixture was cooled to 0° C. and a solution of 1-benzyl-2-chloromethylimidazole hydrochloride (40.0 g, prepared as described in J.A.C.S. 1949, 383) in dry ethanol (250 ml) was added over 30 minutes with stirring. The mixture was stirred at ambient temperature for 2 hours and then the ethanol removed under reduced pressure. Ice cold 2M hydrochloric acid (400 ml) was added to the residue and the mixture was washed with ether. The aqueous layer was basified with solid sodium carbonate and then extracted with dichloromethane to give ethyl 2-carbethoxy-3-(1-benzyl-1H-imidazol-2-yl) propanoate as an oil.

b) A mixture of the product from part a) (47.0 g), sodium chloride (16.6 g), water (5.1 g) and dimethyl sulphoxide (500 ml) was heated at 150° C. for 6 hours. The mixture was cooled to ambient temperature and left to stand at this temperature for 3 days. The mixture was flooded with water and extracted with dichloromethane to give an oil which was distilled under high vacuum to give ethyl 3-(1-benzyl-1H-imidazol-2-yl)propanoate, b.p. 170–172° C. at 0.8 mbar.

c) A solution of diisobutylaluminium hydride (14.3 ml of a 1.5M solution in toluene) was added dropwise with stirring to a solution of the product from part b) (5.0 g) in dichloromethane (200 ml) under nitrogen. The mixture was stirred for 20 minutes at −60° C. Water (15 ml) was added dropwise and the mixture allowed to warm up to ambient temperature. Aqueous sodium tartrate solution (10 ml of a 2.3M solution) was added dropwise followed by dichloromethane (100 ml). The mixture was stirred for 30 minutes and then filtered. The filtrate was washed with brine, dried and evaporated to give an oil which was purified by flash column chromatography on silica using petrol, then ethyl acetate/petrol/triethylamine (45:45:10) and then ethyl acetate/triethylamine (9:1) as the mobile phases to give 3-(1-benzyl-1H-imidazol-2-yl) propionaldehyde as an oil.

2-[3-(Imidazol-1-yl)-propylamino]-2-methyl-1-propanol 3-(Imidazol-1-yl)propionaldehyde diethyl acetal (8.1 g) was converted into the free aldehyde, as described in Example 24, and then added to a mixture of 2-amino-2-methylpropanol (1.83 g) in acetonitrile (40 ml) and 4A molecular sieves (6.0 g). The mixture was reacted following the procedure of Example 24 to give 2-[3-(imidazol-1-yl)propylamino]-2-methyl-1-propanol, m.p. 81–85° C.

What is claimed is:

1. A compound of formula (I)

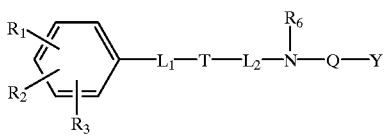

or a pharmaceutically acceptable salt thereof, in which
$R_1$ is hydrogen;
halo;
cyano;
a cyano $C_{1-6}$ alkyl group;
a $C_{1-12}$ alkyl group which is unsubstituted or substituted by one or more hydroxy groups;
a $C_{1-6}$, alkoxy group;
phenoxy which is unsubstituted or substituted;
phenyl which is unsubstituted or substituted;
a $C_{2-6}$, alkoxycarbonyl group;
an amino group of formula —$NR_{13}R_{14}$, in which $R_{13}$ and $R_{14}$ are independently hydrogen or a $C_{1-4}$ alkyl group; or $R_{13}$ and $R_{14}$ together with the nitrogen atom to which they are attached form a saturated 3 to 7-membered heterocyclic ring, said ring optionally containing sulphur, oxygen or an additional nitrogen atom, wherein the ring may be substituted by one or more $C_{1-4}$ alkyl groups; a group of formula —$N(R_{15})SO_2R_{16}$; in which $R_{15}$ is hydrogen or $C_{1-6}$ alkyl; and $R_{16}$ is hydroxy, a $C_{1-6}$ alkyl group or substituted phenyl;
a halogenated $C_{1-4}$ alkoxy group;
a halogenated $C_{1-4}$ alkyl group;
arylalkoxy which is unsubstituted or substituted;
hydroxy;
a phenyl $C_{1-6}$ alkyl group which is unsubstituted or substituted;
a ($C_{2-6}$ alkoxycarbonyl)vinyl group;
a group of formula —$S(O)_nR_7$, in which $R_7$ is a $C_{1-6}$alkyl group, and n is 0, 1 or 2;
or n is 2 and $R_7$ is a group of formula —$N(R_{17})R_{18}$, in which $R_{17}$ and $R_{18}$ independently are hydrogen, a $C_{1-6}$ alkyl group, a $C_{3-6}$ cycloalkyl group or phenyl which is unsubstituted or substituted; or $R_{17}$ and $R_{18}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;
a $C_{2-6}$ alkoxycarbonyl $C_{1-6}$ alkyl group;
a carboxy $C_{1-6}$ alkyl group;
a carbamoyl group of formula —$CONR_{11}R_{12}$, in which $R_{11}$ and $R_{12}$ are independently hydrogen, a $C_{1-6}$ alkyl group, a $C_{3-8}$ cycloalkyl group or phenyl which is unsubstituted or substituted; or $R_{11}$ and $R_{12}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;

a carbamoylvinyl group of formula —CH=CH—$CON(R_{11})R_{12}$ in which $R_{11}$ and $R_{12}$ are as defined above;
a group of formula —$OSO_2R_{21}$, in which $R_{21}$ is a $C_{1-6}$ alkyl group or a phenyl group which is unsubstituted or substituted;
4,5-dihydrothiazol-2-yl, 4,4-dimethyl-2-oxazolin-2-yl;
or a group of formula —$NR_{60}R_{61}$, in which $R_{60}$ is hydrogen or a $C_{1-6}$ alkyl group; and
$R_{61}$ is a $C_{1-6}$ alkanoyl group or benzoyl which is unsubstituted or substituted;
or $R_1$ is a group of formula —$(O)_z$-$L_3$G, wherein z is 0 or 1; $L_3$ is a $C_{1-4}$ alkylene chain which is unsubstituted or substituted by one or more $C_{1-4}$ alkyl groups; and G is a group of formula a), b), c), or d):

a) —$NR_{22}R_{23}$, wherein
$R_{22}$ is hydrogen or a $C_{1-6}$ alkyl group; and
$R_{23}$ is hydrogen; a $C_{1-6}$ alkyl group; a $C_{1-6}$ alkanoyl group; phenylsulphonyl which is unsubstituted or substituted; benzoyl which is unsubstituted or substituted; a group of formula —$CONR_{24}R_{25}$ wherein $R_{24}$ is hydrogen, a $C_{1-6}$ alkyl group or a $C_{3-6}$ cycloalkyl group, and $R_{25}$ is hydrogen; a $C_{1-6}$ alkyl group; or phenyl which is unsubstituted or substituted;
or $R_{24}$ and $R_{25}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;

b) —$S(O)_mR_{26}$, wherein
$R_{26}$ is a $C_{1-6}$ alkyl group or a phenyl group which is unsubstituted or substituted, and m is 0, 1 or 2; or m is 2 and $R_{26}$ is a group of formula —$N(R_{17})R_{18}$ in which $R_{17}$ and $R_{18}$ independently are hydrogen, a $C_{1-6}$ alkyl group, a $C_{3-6}$ cycloalkyl group or phenyl which is unsubstituted or substituted; or $R_{17}$ and $R_{18}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more $C_{1-4}$ alkyl groups;

c) —$CONR_{27}R_{25}$ wherein
$R_{27}$ is hydrogen or a $C_{1-6}$ alkyl group; and
$R_{28}$ is hydrogen, a $C_{1-6}$ alkyl group, a $C_{3-8}$ cycloalkyl group, a phenyl $C_{1-6}$ alkyl group in which the phenyl ring is unsubstituted or substituted, or phenyl which is unsubstituted or substituted; or $R_{27}$ and $R_{28}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more $C_1$4 alkyl groups;

d) —$OR_2$, wherein
$R_{29}$ is a $C_{1-6}$ alkyl group, phenyl which is unsubstituted or substituted, a phenyl $C_{1-6}$ alkyl group in which the phenyl ring is unsubstituted or substituted, a $C_{1-6}$ alkanoyl group, benzoyl which is unsubstituted or substituted, a $C_{1-6}$ alkylsulphonyl group, a phenylsulphonyl group which is unsubstituted or substituted; or $R_{29}$ is a group of formula —$L_4COR_{32}$ in which $L_4$ is a $C_{1-4}$ alkylene chain which is unsubstituted or substituted by one or more $C_{1-4}$ alkyl groups; and $R_{32}$ is hydrogen, a $C_{1-6}$ alkyl group, a $C_{1-6}$ alkoxy group, phenyl which is unsubstituted or substituted, or phenoxy which is unsubstituted or substituted;

$R_2$ and $R_3$ independently are
hydrogen;
halo;
a $C_{1-6}$ alkyl group which is unsubstituted or substituted by one or more hydroxy groups;
a $C_{1-6}$ alkoxy group;
an amino group of formula —$NR_{13}R_{14}$ in which $R_{13}$ and $R_{14}$ are independently hydrogen or a $C_{1-4}$ alkyl group; or $R_{13}$ and $R_{14}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;
a halogenated $C_{1-4}$ alkoxy group;
a halogenated $C_{1-4}$ alkyl group;
hydroxy;
a group of formula —$S(O)_nR_7$, in which $R_7$ is a $C_{1-6}$ alkyl group and n is 0, 1 or 2; or n is 2 and $R_7$ is a group of formula —$N(R_{17})R_{18}$ in which $R_{17}$ and $R_{18}$ independently are hydrogen, a $C_{1-6}$ alkyl group, a $C_{3-6}$ cycloalkyl group or phenyl which is unsubstituted or substituted; or $R_{17}$ and $R_{18}$ together with the nitrogen atom to which they are attached form a saturated 3–7 membered heterocyclic ring, optionally containing sulphur, oxygen or an additional nitrogen atom, wherein the ring may be unsubstituted or substituted by one or more $C_{1-4}$ alkyl groups;
a group of formula —$NR_{60}R_{61}$ in which $R_{60}$ is hydrogen or a $C_{1-6}$ alkyl group; and
$R_{61}$ is a $C_{1-6}$ alkanoyl group, or unsubstituted or substituted benzoyl;

or $R_1$ and $R_2$ together with the phenyl ring to which they are attached form an unsubstituted or substituted or naphthyl group;

or $R_2$ is attached to a position on the phenyl ring adjacent to the position of attachment of $L_1$ on the phenyl ring and —$L_1$-T-$L_2$— and $R_2$ together with the phenyl ring to which they are attached form an indane ring which is which is unsubstituted or substituted;

$L_1$ is a bond; or a $C_{1-4}$ alkylene chain, a $C_{3-6}$ cycloalkylene group, or a $C_{3-6}$ cycloalkylidene group, each of which is unsubstituted or substituted by a) one or more unsubstituted or substituted or phenyl groups, b) one or more $C_{1-4}$ alkyl groups wherein the alkyl groups are unsubstituted or substituted by one or more hydroxy groups or a $C_{2-6}$ alkoxycarbonyl group, or c) by one or more $C_{3-6}$ cycloalkyl groups;

T is a bond or O, S, SO, $SO_2$, a carbonyl group, or a group of formula (5)

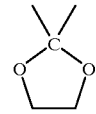

(5)

$L_2$ is a $C_{1-4}$ alkylene chain, a $C_{3-6}$ cycloalkylene group, or a $C_{3-6}$ cycloalkylidene group, each of which is unsubstituted or substituted by one or more unsubstituted or substituted phenyl groups; by one or more $C_{1-4}$ alkyl groups wherein the alkyl groups are substituted by one or more hydroxy groups or a $C_{2-6}$ alkoxycarbonyl group; or by one or more $C_{3-6}$ cycloalkyl groups;

and when T is a carbonyl group $L_2$ additionally is a $C_{1-4}$ oxyalkylene chain, a $C_{3-6}$ oxycycloalkylene group, or a $C_{3-6}$ oxycycloalkylidene group, each of which is unsubstituted or substituted by one or more unsubstituted or substituted phenyl groups; by one or more $C_{1-4}$ alkyl groups wherein the alkyl groups are unsubstituted or substituted by one or more hydroxy groups or a $C_{2-6}$ alkoxycarbonyl group; or by one or more $C_{3-6}$ cycloalkyl groups;

$R_6$ is hydrogen, a $C_{1-4}$ alkyl group which is unsubstituted or substituted by one or more hydroxy groups or by a $C_{2-6}$ alkoxycarbonyl group;

Q is a $C_{1-9}$ alkylene chain which is unsubstituted or substituted by one or more hydroxy groups and/or by one or more $C_{1-4}$ alkyl groups which are unsubstituted or substituted by one or more hydroxy groups; and/or optionally interrupted by oxygen or a carbonyl group;

Y is an imidazole ring of formula (1), (2) or (3)

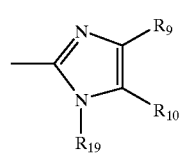

(1)

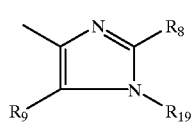

(2)

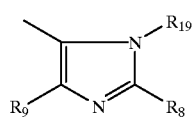

(3)

in which
$R_8$ is hydrogen, a $C_{1-6}$ alkyl group, a halogenated $C_{1-6}$ alkyl group, halo, a $C_{1-4}$ alkoxy group, a halogenated $C_{1-4}$ alkoxy group, a $C_{1-4}$ hydroxyalkyl group, unsubstituted or substituted phenyl, unsubstituted or substituted benzoyl, an unsubstituted or sub benzoyl $C_{1-4}$ alkyl group, or a phenyl $C_{1-4}$ alkyl group in which the alkyl chain is unsubstituted or substituted by one or more hydroxy groups or one or more $C_{1-4}$ alkyl groups and the phenyl ring is unsubstituted or substituted;

$R_9$ and $R_{10}$ independently are hydrogen; a $C_{1-6}$ alkyl group; halo; a halogenated $C_{1-6}$ alkyl group; a $C_{1-4}$ alkoxy group; a halogenated $C_{1-4}$ alkoxy group; unsubstituted or substituted phenyl; a $C_{1-4}$ hydroxyalkyl group; a $C_{2-6}$ alkoxycarbonyl group; nitro; an amino group of formula $NR_{30}R_{31}$ in which $R_{30}$ and $R_{31}$ are independently hydrogen or a $C_{1-4}$ alkyl group; or $R_{30}$ and $R_{31}$ together with the nitrogen atom to which they are attached form a saturated 3–7 membered heterocyclic ring, optionally containing sulphur, oxygen or an additional nitrogen atom, wherein the ring is unsubstituted or substituted by one or more $C_{1-4}$ alkyl groups; a $C_{1-6}$ alkanoyloxy $C_{1-4}$ alkyl group; a cyano $C_{1-6}$ alkyl group; or a group of formula g) or h), g) —$L_5NR_{40}R_4$, in which $L_5$ is a $C_{1-4}$ alkylene chain which is unsubstituted or substituted by one or more $C_{1-4}$ alkyl groups;

$R_{40}$ is hydrogen or a $C_{1-6}$ alkyl group, and $R_{41}$ is hydrogen; a $C_{1-6}$ alkyl group; a group of formula $SO_2R_{42}$ in which $R_{42}$ is a $C_{1-6}$ alkyl group or unsubstituted or substituted phenyl; a group of formula $COR_{43}$ in which $R_{43}$ is a $C_{1-6}$ alkyl group; unsubstituted or substituted phenyl; unsubstituted or substituted pyridyl; unsubstituted or substituted thienyl; unsubstituted or substituted furyl; or unsubstituted or substituted pyrrolyl; a $C_{1-6}$ alkoxy group, unsubstituted or substituted phenoxy or unsubstituted or substituted arylalkyl; or $R_{41}$ is a group of formula $CONR_{44}R_{45}$ in which $R_{44}$ is hydrogen, a $C_{1-6}$ alkyl group or a $C_{3-6}$ cycloalkyl group, and $R_{45}$ is hydrogen, a $C_{1-6}$ alkyl group or unsubstituted or substituted phenyl; or $R_{44}$ and $R_{45}$ together with the nitrogen atom to which they are attached form a saturated 3–7 membered heterocyclic ring, optionally containing sulphur, oxygen or an additional nitrogen atom, wherein the ring may be unsubstituted or substituted by one or more $C_{1-4}$ alkyl groups; or h) —$L_7CONR_{90}R_{91}$ in which $L_7$ is a $C_{1-6}$ alkylene chain which is unsubstituted or substituted by one or more $C_{1-4}$ alkyl groups; and $R_{90}$ and $R_{91}$ are independently hydrogen, a $C_{1-6}$ alkyl group or unsubstituted or substituted phenyl; or $R_{90}$ and $R_{91}$ together with the nitrogen atom to which they are attached form a saturated 3–7 membered heterocyclic ring, optionally containing sulphur, oxygen or an additional nitrogen atom, wherein the ring is unsubstituted or substituted by one or more $C_{1-4}$ alkyl groups; and $R_{19}$ is hydrogen, a $C_{1-6}$ alkyl group, an aryl group or an aryl $C_{1-6}$ alkyl group;

with a first proviso that when Y is a group of formula (2) or (3) then a) when $R_1$, $R_2$ and $R_3$ independently are hydrogen, halo, methyl, ethyl, methoxy, amino, hydroxy or nitro; and $L_1$-T-$L_2$ is methylene; $R_6$ is hydrogen; Q is methylene; $R_8$ is hydrogen, a $C_{1-6}$ alkyl group or phenyl; and $R_9$ is hydrogen or a $C_{1-6}$ alkyl group;

then $R_{19}$ is other than hydrogen, a $C_{1-6}$ alkyl group or substituted benzyl; or b) when $R_1$, $R_2$ and $R_3$ independently are hydrogen, halo or a $C_{1-6}$ alkyl group; $L_1$-T-$L_2$ is methylene or ethylene; $R_6$ is hydrogen or a $C_{1-6}$ alkyl group; Q is methylene or ethylene; and $R_8$ and $R_9$ independently are hydrogen or a $C_{1-6}$ alkyl group;

then $R_{19}$ is other than a $C_{1-6}$ alkyl group;

and a second proviso that when Y is a group of formula (2) and $R_1$, $R_2$ and $R_3$ independently are hydrogen, halo, trifluoromethyl, a $C_{1-3}$ alkyl group or a $C_{1-3}$ alkoxy group; R is hydrogen or methyl; Q is a chain of formula —$(CH_2)_m$—$CH(R_k)$— in which m is 0, 1, 2 or 3 and $R_k$ is hydrogen, a $C_{1-3}$ alkyl group or hydroxy; and $R_9$ and $R_{10}$ independently are hydrogen or phenyl and $R_{19}$ is aryl or substituted benzyl;

then $L_1$-T-$L_2$ is other than methylene, ethylene or trimethylene.

2. A compound of formula (II)

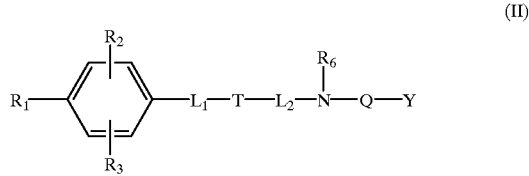

(II)

or a pharmaceutically acceptable salt thereof, in which $R_1$ is hydrogen;
halo;
cyano;
a cyano $C_{1-6}$ alkyl group;
a $C_{1-12}$ alkyl group which is unsubstituted or substituted by one or more hydroxy groups;
a $C_{1-6}$ alkoxy group;
phenoxy which is unsubstituted or substituted;
phenyl which is unsubstituted or substituted;
a $C_{2-6}$ alkoxycarbonyl group;
an amino group of formula —$NR_{13}R_{14}$, in which $R_{13}$ and $R_{14}$ are independently hydrogen or a $C_{1-4}$ alkyl group; or $R_{13}$ and $R_{14}$ together with the nitrogen atom to which they are attached form a saturated 3 to 7-membered heterocyclic ring, said ring optionally containing sulphur, oxygen or an additional nitrogen atom, wherein the ring may be substituted by one or more $C_{1-4}$ alkyl groups;
a group of formula —$N(R_{15})SO_2R_{16}$, in which $R_{15}$ is hydrogen or $C_{1-6}$ alkyl; and $R_{16}$ is hydroxy, a $C_{1-6}$ alkyl group or substituted phenyl;
a halogenated $C_{1-4}$ alkoxy group;
a halogenated $C_{1-4}$ alkyl group;
arylalkoxy which is unsubstituted or substituted;
hydroxy;
a phenyl $C_{1-6}$ alkyl group which is unsubstituted or substituted;
a ($C_{2-6}$ alkoxycarbonyl)vinyl group;
a group of formula —$S(O)_nR_7$, in which $R_7$ is a $C_{1-6}$ alkyl group, and n is 0, 1 or 2;
or n is 2 and $R_7$ is a group of formula —$N(R_{17})R_{18}$, in which $R_{17}$ and $R_{18}$ independently are hydrogen, a $C_{1-6}$ alkyl group, a $C_{3-6}$ cycloalkyl group or phenyl which is unsubstituted or substituted; or $R_{17}$ and $R_{18}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;
a $C_{2-6}$ alkoxycarbonyl $C_{1-6}$ alkyl group;
a carboxy $C_{1-6}$ alkyl group;
a carbamoyl group of formula —$CONR_{11}R_{12}$, in which $R_{11}$ and $R_{12}$ are independently hydrogen, a $C_{1-6}$ alkyl group, a $C_{3-8}$ cycloalkyl group or phenyl which is unsubstituted or substituted; or $R_{11}$ and $R_{12}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;
a carbamoylvinyl group of formula —$CH=CH$—$CON(R_{11})R_{12}$ in which $R_{11}$ and $R_{12}$ are as defined above;
a group of formula —$OSO_2R_{21}$, in which $R_{21}$ is a $C_{1-6}$ alkyl group or a phenyl group which is unsubstituted or substituted;

4,5-dihydrothiazol-2-yl, 4,4dimethyl-2-oxazolin-2-yl;
or a group of formula —NR$_{60}$R$_{61}$ in which R$_{60}$ is hydrogen or a C$_{1-6}$ alkyl group; and
R$_{61}$ is a C$_{1-6}$ alkanoyl group or benzoyl which is unsubstituted or substituted;
or R$_1$ is a group of formula —(O)$_z$-L$_3$G, wherein z is 0 or 1; L$_3$ is a C$_{1-4}$ alkylene chain which is unsubstituted or substituted by one or more C$_{1-4}$ alkyl groups; and G is a group of formula a), b), c), or d):
 a) —NR$_{22}$R$_{23}$
wherein R22 is hydrogen or a C$_{1-6}$ alkyl group; and R$_{23}$ is hydrogen; a C$_{1-6}$ alkyl group; a C$_{1-6}$ alkanoyl group; phenylsulphonyl which is unsubstituted or substituted; benzoyl which is unsubstituted or substituted; a group of formula —CONR$_{24}$R$_{25}$, wherein R$_{24}$ is hydrogen, a C$_{1-6}$ alkyl group or a C$_{3-6}$ cycloalkyl group, and R$_{25}$ is hydrogen; a C$_{1-6}$ alkyl group; or phenyl which is unsubstituted or substituted; or R$_{24}$ and R$_{25}$ together with the nitrogen atom to which they are attached form a saturated 3 to 7-membered heterocyclic ring, optionally containing sulphur, oxygen or an additional nitrogen atom, wherein the ring is unsubstituted or substituted by one or more C$_{1-4}$ alkyl groups;
 b) —S(O)$_m$R$_{26}$
wherein R$_{26}$ is a C$_{1-6}$ alkyl group or a phenyl group which is unsubstituted or substituted, and m is 0, 1 or 2; or m is 2 and R$_{26}$ is a group of formula —N(R$_{17}$)R$_{18}$ in which R$_{17}$ and R$_{18}$ independently are hydrogen, a C$_{1-6}$ alkyl group, a C$_{3-6}$ cycloalkyl group or phenyl which is unsubstituted or substituted; or R$_{17}$ and R$_{18}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more C$_1$4 alkyl groups;
 c) —CONR$_{27}$R$_{28}$
wherein R$_{27}$ is hydrogen or a C$_{1-6}$ alkyl group; and R$_{28}$ is hydrogen, a C$_{1-6}$ alkyl group, a C$_{3-6}$ cycloalkyl group, a phenyl C$_{1-6}$ alkyl group in which the phenyl ring is unsubstituted or substituted, or phenyl which is unsubstituted or substituted; or R$_{27}$ and R$_{28}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more C$_{1-4}$ alkyl groups;
 d) —OR$_{29}$
wherein R$_{29}$ is a C$_{1-6}$ alkyl group, phenyl which is unsubstituted or substituted, a phenyl C$_{1-6}$ alkyl group in which the phenyl ring is unsubstituted or substituted, a C$_{1-6}$ alkanoyl group, benzoyl which is unsubstituted or substituted, a C$_{1-6}$ alkylsulphonyl group, a phenylsulphonyl group which is unsubstituted or substituted; or R$_{29}$ is a group of formula —L$_4$COR$_{32}$ in which L$_4$ is a C$_{1-4}$ alkylene chain which is unsubstituted or substituted by one or more C$_{1-4}$ alkyl groups; and
R$_{32}$ is hydrogen, a C$_{1-6}$ alkyl group, a C$_{1-6}$ alkoxy group, phenyl which is unsubstituted or substituted, or phenoxy which is unsubstituted or substituted;
R$_2$ and R$_3$ independently are
hydrogen;
halo;
a C$_{1-6}$ alkyl group which is unsubstituted or substituted by one or more hydroxy groups;

a C$_{1-6}$ alkoxy group;
an amino group of formula —NR$_{13}$R$_{14}$ in which R$_{13}$ and R$_{14}$ are independently hydrogen or a C$_{1-4}$ alkyl group; or R$_{13}$ and R$_{14}$ together with the nitrogen atom to which they are attached form a saturated 3 to 7-membered heterocyclic ring, optionally containing sulphur, oxygen or an additional nitrogen atom, wherein the ring is unsubstituted or substituted by one or more C$_{1-4}$ alkyl groups;
a halogenated C$_{1-4}$ alkoxy group;
a halogenated C$_{1-4}$ alkyl group;
hydroxy;
a group of formula —(O)$_n$R$_7$, in which R$_7$ is a C$_{1-6}$ alkyl group and n is 0, 1 or 2; or n is 2 and R$_7$ is a group of formula —N(R$_{17}$)R$_{18}$ in which R$_{17}$ and R$_{18}$ independently are hydrogen, a C$_1$ alkyl group, a C$_{3-6}$ cycloalkyl group or phenyl which is unsubstituted or substituted; or R$_{17}$ and R$_{18}$ together with the nitrogen atom to which they are attached form a saturated 3–7 membered heterocyclic ring, optionally containing sulphur, oxygen or an additional nitrogen atom, wherein the ring may be unsubstituted or substituted by one or more C$_{1-4}$ alkyl groups;
a group of formula —NR$_{60}$R$_{61}$ in which R$_{60}$ is hydrogen or a C$_{1-6}$ alkyl group; and
R$_{61}$ is a C$_{1-6}$ alkanoyl group, or unsubstituted or substituted benzoyl;
or R$_1$ and R$_2$ together with the phenyl ring to which they are attached form an unsubstituted or substituted or naphthyl group;
or R$_2$ is attached to a position on the phenyl ring adjacent to the position of attachment of L$_1$ on the phenyl ring and —L$_1$-T-L$_2$— and R$_2$ together with the phenyl ring to which they are attached form an indane ring which is which is unsubstituted or substituted;
L$_1$ is a bond; or a C$_{1-4}$ alkylene chain, a C$_{3-6}$ cycloalkylene group, or a C$_{3-6}$ cycloalkylidene group, each of which is unsubstituted or substituted by a) one or more unsubstituted or substituted or phenyl groups, b) one or more C$_{1-4}$ alkyl groups wherein the alkyl groups are unsubstituted or substituted by one or more hydroxy groups or a C$_{2-6}$ alkoxycarbonyl group, or c) by one or more C$_{3-6}$ cycloalkyl groups;
T is a bond or O, S, SO, SO$_2$, a carbonyl group, or a group of formula (5)

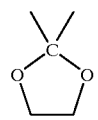

(5)

L$_2$ is a C$_{1-4}$ alkylene chain, a C$_{3-6}$ cycloalkylene group, or a C$_{3-6}$ cycloalkylidene group, each of which is unsubstituted or substituted by one or more unsubstituted or substituted phenyl groups; by one or more C$_{1-4}$ alkyl groups wherein the alkyl groups are substituted by one or more hydroxy groups or a C$_{2-6}$alkoxycarbonyl group; or by one or more C$_{3-6}$ cycloalkyl groups;
and when T is a carbonyl group L$_2$ additionally is a C$_{1-4}$ oxyalkylene chain, a C$_{3-6}$ oxycycloalkylene group, or a C$_{3-6}$ oxycycloalkylidene group, each of which is unsubstituted or substituted by one or more unsubstituted or substituted phenyl groups; by one or more C$_{1-4}$alkyl groups wherein the alkyl groups are unsubstituted or substituted by one or more hydroxy groups or a $C_{2-6}$ alkoxycarbonyl group; or by one or more $C_{3-6}$ cycloalkyl groups;

$R_6$ is hydrogen, a $C_{1-4}$ alkyl group which is unsubstituted or substituted by one or more hydroxy groups or by a $C_{2-6}$ alkoxycarbonyl group;

Q is a $C_{1-9}$ alkylene chain which is unsubstituted or substituted by one or more hydroxy groups and/or by one or more $C_{1-4}$ alkyl groups which are unsubstituted or substituted by one or more hydroxy groups; and/or optionally interrupted by oxygen or a carbonyl group;

Y is an imidazole ring of formula (1), (2) or (3)

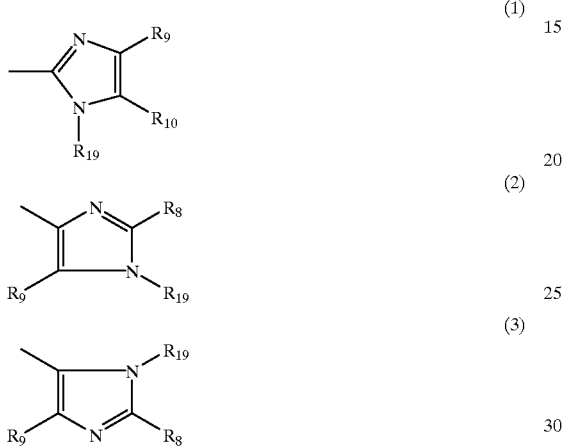

in which $R_8$ is hydrogen; a $C_{1-6}$ alkyl group; trifluoromethyl; halo; a $C_{1-4}$ alkoxy group; a $C_{1-4}$ hydroxyalkyl group; unsubstituted or substituted phenyl; unsubstituted or substituted benzoyl; an unsubstituted or substituted benzoyl $C_{1-4}$ alkyl group; or a phenyl $C_{1-4}$ alkyl group in which the alkyl chain is optionally substituted by one or more hydroxy groups or one or more $C_{1-4}$ alkyl groups and the phenyl ring is optionally substituted;

$R_9$ and $R_{10}$ independently are hydrogen; a $C_{1-6}$ alkyl group; halo; trifluoromethyl; a $C_{1-4}$ alkoxy group; unsubstituted or substituted phenyl; a $C_{1-4}$ hydroxyalkyl group; a $C_{2-6}$ alkoxycarbonyl group; nitro; an amino group of formula $NR_{30}R_{31}$ in which $R_{30}$ and $R_{31}$ are independently hydrogen or a $C_{1-4}$ alkyl group; or $R_{30}$ and $R_{31}$ together with the nitrogen atom to which they are attached represent a saturated 3 to 7-membered heterocyclic ring, optionally containing sulphur, oxygen or an additional nitrogen atom, wherein the ring may be optionally substituted by one or more $C_{1-4}$ alkyl groups; a $C_{1-6}$ alkanoyloxy $C_{1-4}$ alkyl group; a cyano $C_{1-6}$ alkyl group; or a group of formula g) or h), g) —L-$NR_{40}R_{41}$ in which $L_5$ is a $C_{1-4}$ alkylene chain which is unsubstituted or substituted by one or more $C_{1-4}$ alkyl groups;

$R_{40}$ is hydrogen or a $C_{1-6}$ alkyl group, and $R_{41}$ is hydrogen; a $C_{1-6}$ alkyl group; a group of formula $SO_2R_{42}$ in which $R_{42}$ is a $C_{1-6}$ alkyl group or unsubstituted or substituted phenyl; a group of formula $COR_{43}$ in which $R_{43}$ is a $C_{1-6}$ alkyl group; unsubstituted or substituted phenyl; unsubstituted or substituted pyridyl; unsubstituted or substituted thienyl; unsubstituted or substituted furyl; or unsubstituted or substituted pyrrolyl; a $C_{1-6}$ alkoxy group, unsubstituted or substituted phenoxy or unsubstituted or substituted arylalkyl; or $R_{41}$ is a group of formula $CONR_{44}R_4$ in which $R_{44}$ is hydrogen, a $C_{1-6}$ alkyl group or a $C_{3-6}$ cycloalkyl group, and $R_{45}$ is hydrogen, a $C_{1-6}$ alkyl group or unsubstituted or substituted phenyl; or $R_{44}$ and $R_{45}$ together with the nitrogen atom to which they are attached form a saturated 3–7 membered heterocyclic ring, optionally containing sulphur, oxygen or an additional nitrogen atom, wherein the ring may be unsubstituted or substituted by one or more $C_{1-4}$ alkyl groups; or h) —$L_7CONR_{90}R_{91}$ in which $L_7$ is a $C_{1-6}$ alkylene chain; and $R_{90}$ and $R_{91}$ are independently hydrogen, a $C_{1-6}$ alkyl group or unsubstituted or substituted phenyl; or $R_{90}$ and $R_{91}$ together with the nitrogen atom to which they are attached form a saturated 3 to 7-membered heterocyclic ring, optionally containing sulphur, oxygen or an additional nitrogen atom, wherein the ring may be optionally substituted by one or more $C_{1-4}$ alkyl groups; and $R_{19}$ is hydrogen, a $C_{1-6}$ allyl group, an aryl group or an aryl $C_{1-6}$ alkyl group.

3. The compound of formula (I), as defined in claim 1, in which $R_1$ is hydrogen;

halo;

hydroxy;

cyano;

a $C_{1-12}$ alkyl group which is unsubstituted or substituted by one or more hydroxy groups;

a $C_{1-6}$ alkoxy group;

a $C_{2-6}$ alkoxycarbonyl group;

unsubstituted or substituted phenyl;

a halogenated $C_{1-4}$ alkyl group;

unsubstituted or substituted arylalkoxy;

a group of formula —$(O)_nR_7$ in which $R_7$ is a $C_{1-6}$ alkyl group and n is 0; or n is 2 and $R_7$ is a group of formula —$N(R_{17})R_{18}$ in which $R_{17}$ and $R_{18}$ independently are hydrogen, a $C_{1-6}$ alkyl group or a $C_{3-6}$ cycloalkyl group; or $R_{17}$ and $R_{18}$ together with the nitrogen atom to which they are attached form a saturated 3 to 7-membered heterocyclic ring, optionally containing sulphur, oxygen or an additional nitrogen atom, wherein the ring may be optionally substituted by one or more $C_{1-4}$ alkyl groups;

a carbamoyl group of formula —$CONR_{11}R_{12}$ in which $R_{11}$ and $R_{12}$ are independently hydrogen, a $C_{1-6}$ alkyl group or a $C_{3-8}$ cycloalkyl group;

a carbamoylvinyl group of formula —CH=CH—CON$(R_{11})R_{12}$ in which $R_{11}$ and $R_{12}$;

a group of formula —$OSO_2R_{21}$ in which $R_{21}$ is a $C_{1-6}$ alkyl group, an unsubstituted or substituted phenyl group, 4,5-dihydrothiazol-2-yl or 4,4-dimethyl-2-oxazolin-2-yl; or a group of formula —$NR_{60}R_{61}$ in which $R_{60}$ is hydrogen and $R_{61}$ is a $C_{1-6}$ alkanoyl group or unsubstituted or substituted benzoyl;

or $R_1$ is a group of formula —$(O)_z$-L3G, wherein z is 0 or 1, L3 is a C, 4alkylene chain which is unsubstituted or substituted by one or more $C_{1-4}$alkyl groups, and G is a group of formula a), b), c), or d)

a) —$NR_{22}R_{23}$ in which $R_{22}$ is hydrogen; and $R_{23}$ is hydrogen, unsubstituted or substituted phenylsulphonyl, a group of formula —CONR$_{24}$R$_{25}$ wherein R$_{24}$ is hydrogen or a C$_{1-6}$ alkyl group, and R$_{25}$ is hydrogen or a C$_{1-6}$ alkyl group or unsubstituted or substituted benzoyl;

b) —S(O)$_m$R$_{26}$ in which R$_{26}$ is a C$_{1-6}$ alkyl group or an unsubstituted or substituted phenyl group and m is 0, 1 or 2; or m is 2 and R$_{28}$ is a group of formula —N(R$_{17}$)R$_{18}$ in which R$_{17}$ and R$_{18}$ independently are hydrogen, a C$_{1-6}$ alkyl group or a C$_{3-6}$ cycloalkyl group;

c) —CONR$_{27}$R$_{28}$ in which R$_{27}$ is hydrogen and R$_{28}$ is hydrogen, a C$_{1-6}$ alkyl group, a C$_{3-8}$ cycloalkyl group or a phenyl C$_{1-6}$ alkyl group in which the phenyl ring is unsubstituted or substituted;

d) —OR$_{29}$ in which R$_{29}$ is a phenyl C$_{1-6}$ alkyl group in which the phenyl ring is unsubstituted or substituted;

R$_2$ and R$_3$ independently are hydrogen, halo, a C$_{1-6}$ alkyl group which is unsubstituted or substituted by one or more hydroxy groups, a C$_{1-6}$ alkoxy group, or a group of formula —NR$_{60}$OR$_{61}$ in which R$_{60}$ is hydrogen or a C$_{1-6}$ alkyl group and R$_{61}$ is unsubstituted or substituted benzoyl;

or R$_2$ is attached to a position on the phenyl ring adjacent to the position of L$_1$ and —L$_1$-T-L$_2$— and R$_2$ together with the phenyl ring to which they are attached form an indane ring;

L$_1$ is a bond or a C$_{1-4}$ alkylene chain which is unsubstituted or substituted by one or more C$_{1-4}$ alkyl groups;

T is a bond or O, S, SO, SO$_2$, a carbonyl group or a group of formula (5)

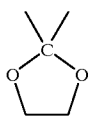

(5)

L$_2$ is a C$_{1-4}$ alkylene chain which is unsubstituted or substituted by one or more C$_{1-4}$ alkyl groups; or when T is a carbonyl group L$_2$ additionally is a C$_{1-4}$ oxyalkylene chain which is unsubstituted or substituted by one or more C$_{1-4}$ alkyl groups;

R$_6$ is hydrogen, a C$_{1-4}$ alkyl group which is unsubstituted or substituted by one or more hydroxy groups or by a C$_{2-6}$ alkoxycarbonyl group;

Q is a C$_{1-9}$ alkylene chain which is unsubstituted or substituted by one or more hydroxy groups;

Y is an imidazole ring of formula (1), (2) or (3)

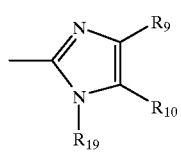

(1)

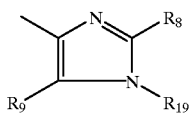

(2)

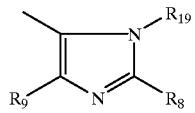

(3)

in which

R$_8$ is hydrogen, a C$_{1-6}$ alkyl group or a phenyl C$_{1-4}$ alkyl group in which the alkyl chain is unsubstituted or substituted by one or more hydroxy groups;

R$_9$ and R$_{10}$ independently are hydrogen or a group of formula —L$_5$—NR$_{40}$R$_{41}$ in which L$_5$ is a C$_{1-4}$ alkylene chain which is unsubstituted or substituted by one or more C$_{1-4}$ alkyl groups; R$_{40}$ is hydrogen or a C$_{1-6}$ alkyl group; and R$_{41}$ is hydrogen, a group of formula SO$_2$R$_{42}$ in which R$_{42}$ is unsubstituted or substituted phenyl, a group of formula COR$_{43}$ in which R$_{43}$ is unsubstituted or substituted phenyl; and R$_{19}$ is hydrogen, a C$_{1-6}$ alkyl group, an aryl group or an aryl C$_{1-6}$ alkyl group.

4. The compound of formula (II), as defined in claim 2, in which

R$_1$ is hydrogen;
halo;
hydroxy;
cyano;
a C$_{1-12}$ alkyl group which is unsubstituted or substituted by one or more hydroxy groups;
a C$_{1-6}$ alkoxy group;
a C$_{2-6}$ alkoxycarbonyl group;
unsubstituted or substituted phenyl;
a halogenated C$_{1-4}$ alkyl group;
unsubstituted or substituted arylalkoxy;
a group of formula —S(O)$_n$R$_7$ in which R$_7$ is a C$_{1-6}$ alkyl group and n is 0; or n is 2 and R$_7$ is a group of formula —N(R$_{17}$)R$_{18}$ in which R$_{17}$ and R$_{18}$ independently are hydrogen, a C$_{1-6}$ alkyl group or a C$_{3-6}$ cycloalkyl group; or R$_{17}$ and R$_{18}$ together with the nitrogen atom to which they are attached form a saturated 3 to 7-membered heterocyclic ring, optionally containing sulphur, oxygen or an additional nitrogen atom, wherein the ring may be optionally substituted by one or more C$_{1-4}$ alkyl groups;
a carbamoyl group of formula —CONR$_{11}$R$_{12}$ in which R$_{11}$ and R$_{12}$ are independently hydrogen, a C$_{1-6}$ alkyl group or a C$_{3-8}$ cycloalkyl group;
a carbamoylvinyl group of formula —CH=CH—CON(R$_{11}$)R$_{12}$ in which R$_{11}$ and R$_{12}$;
a group of formula —OSO$_2$R$_{21}$ in which R$_{21}$ is a C$_{1-6}$ alkyl group, an unsubstituted or substituted phenyl group, 4,5-dihydrothiazol-2-yl or 4,4-dimethyl-2oxazolin-2-yl; or
a group of formula —NR$_{60}$R$_{61}$ in which R$_{60}$ is hydrogen and R$_{61}$ is a C$_{1-6}$ alkanoyl group or unsubstituted or substituted benzoyl;

or R$_1$ is a group of formula —(O)$_z$-L$_3$G, wherein z is 0 or 1, L$_3$ is a C$_{1-4}$ alkylene chain which is unsubstituted or substituted by one or more C$_{1-4}$ alkyl groups, and G is a group of formula a), b), c), or d)

a) —NR$_{22}$R$_{23}$ in which R$_{22}$ is hydrogen; and R$_{23}$ is hydrogen, unsubstituted or substituted phenylsulphonyl, a group of formula —CONR$_{24}$R$_{25}$ wherein R$_{24}$ is hydrogen or a C$_{1-6}$ alkyl group, and R$_{25}$ is hydrogen or a C$_{1-6}$ alkyl group or unsubstituted or substituted benzoyl;

b) —S(O)$_m$R$_{26}$ in which R$_{26}$ is a C$_{1-6}$ alkyl group or an unsubstituted or substituted phenyl group and m is 0, 1 or 2; or m is 2 and R$_{26}$ is a group of formula —N(R$_{17}$)R$_{18}$ in which R$_{17}$ and R$_{18}$ independently are hydrogen, a C$_{1-6}$ alkyl group or a C$_{3-6}$ cycloalkyl group;

c) —CONR$_{27}$R$_{28}$ in which R$_{27}$ is hydrogen and R$_{28}$ is hydrogen, a C$_{1-6}$ alkyl group, a C$_{3-8}$ cycloalkyl group or a phenyl C$_{1-6}$ alkyl group in which the phenyl ring is unsubstituted or substituted;

d) —OR$_{29}$ in which R$_{29}$ is a phenyl C$_{1-6}$ alkyl group in which the phenyl ring is unsubstituted or substituted;

R$_2$ and R$_3$ independently are hydrogen, halo, a C$_{1-6}$ alkyl group which is unsubstituted or substituted by one or more hydroxy groups, a C$_{1-6}$ alkoxy group, or a group of formula —NR$_{60}$R$_{61}$ in which R$_{60}$ is hydrogen or a C$_{1-6}$ alkyl group and R$_{61}$ is unsubstituted or substituted benzoyl;

or R$_2$ is attached to a position on the phenyl ring adjacent to the position of L, and —L$_1$-T-L$_2$— and R$_2$ together with the phenyl ring to which they are attached form an indane ring;

L$_1$ is a bond or a C$_{1-4}$alkylene chain which is unsubstituted or substituted by one or more C$_{1-4}$ alkyl groups;

T is a bond or O, S, SO, SO$_2$, a carbonyl group or a group of formula (5)

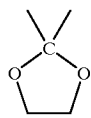

(5)

L$_2$ is a C$_{1-4}$ alkylene chain which is unsubstituted or substituted by one or more C$_{1-4}$ alkyl groups; or when T is a carbonyl group L$_2$ additionally is a C$_{1-4}$ oxyalkylene chain which is unsubstituted or substituted by one or more C$_{1-4}$ alkyl groups;

R$_6$ is hydrogen, a C$_{1-4}$ alkyl group which is unsubstituted or substituted by one or more hydroxy groups or by a C$_{2-6}$ alkoxycarbonyl group;

Q is a C$_{1-9}$ alkylene chain which is unsubstituted or substituted by one or more hydroxy groups;

Y is an imidazole ring of formula (1), (2) or (3)

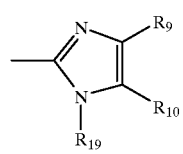

(1)

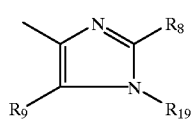

(2)

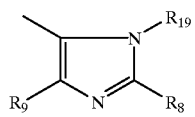

(3)

in which

R$_8$ is hydrogen, a C$_{1-6}$ alkyl group or a phenyl C$_{1-4}$ alkyl group in which the alkyl chain is unsubstituted or substituted by one or more hydroxy groups;

R$_9$ and R$_{10}$ independently are hydrogen or a group of formula —L$_5$—NR$_{40}$R$_{41}$ in which L$_5$ is a C$_{1-4}$ alkylene chain which is unsubstituted or substituted by one or more C$_{1-4}$ alkyl groups; R$_{40}$ is hydrogen or a C$_{1-6}$ alkyl group; and R$_{41}$ is hydrogen, a group of formula SO$_2$R$_{42}$ in which R$_{42}$ is unsubstituted or substituted phenyl, a group of formula COR$_{43}$ in which R$_{43}$ is unsubstituted or substituted phenyl; and R$_{19}$ is hydrogen, a C$_{1-6}$ alkyl group, an aryl group or an aryl C$_{1-6}$ alkyl group.

5. A compound of formula (IIa)

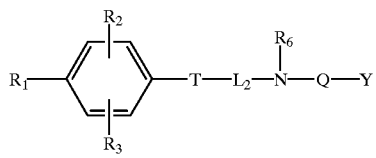

(IIa)

or a pharmaceutically acceptable salt thereof, in which

R$_1$ is hydrogen;
halo;
cyano;
a cyano C$_{1-6}$ alkyl group;
a C$_{1-12}$ alkyl group which is unsubstituted or substituted by one or more hydroxy groups;
a C$_{1-6}$ alkoxy group;
phenoxy which is unsubstituted or substituted;
phenyl which is unsubstituted or substituted;
a C$_{2-6}$ alkoxycarbonyl group;
an amino group of formula —NR$_{13}$R$_{14}$, in which R$_{13}$ and R$_{14}$ are independently hydrogen or a C$_{1-4}$alkyl group; or R$_{13}$ and R$_{14}$ together with the nitrogen atom to which they are attached form a saturated 3 to 7-membered heterocyclic ring, said ring optionally containing sulphur, oxygen or an additional nitrogen atom, wherein the ring may be substituted by one or more C$_{1-4}$ alkyl groups;
a group of formula —N(R$_{15}$)SO$_2$R$_{16}$, in which R$_{15}$ is hydrogen or C$_{1-6}$ alkyl; and R$_{16}$ is hydroxy, a C$_{1-6}$ alkyl group or substituted phenyl;
a halogenated C$_{1-4}$ alkoxy group;
a halogenated C$_{1-4}$ alkyl group;
arylalkoxy which is unsubstituted or substituted;
hydroxy;
a phenyl C$_{1-6}$ alkyl group which is unsubstituted or substituted;
a (C$_{2-6}$ alkoxycarbonyl)vinyl group;
a group of formula —S(O)$_n$R$_7$, in which R$_7$ is a C$_{1-6}$ alkyl group, and n is 0, 1 or 2;
or n is 2 and R$_7$ is a group of formula —N(R$_{17}$)R$_{18}$, in which R$_{17}$ and R$_{18}$ independently are hydrogen, a C$_{1-6}$ alkyl group or unsubstituted or substituted phenyl;

a $C_{2-6}$ alkoxycarbonyl $C_{1-6}$ alkyl group;

a carboxy $C_{1-6}$ alkyl group;

a carbamoyl group of formula —$CONR_{11}R_{12}$ in which $R_{11}$ and $R_{12}$ are independently hydrogen, a $C_{1-6}$ alkyl group, a $C_{3-6}$ cycloalkyl group or unsubstituted or substituted phenyl; or $R_{11}$ and $R_{12}$ together with the nitrogen atom to which they are attached are a saturated 3 to 7-membered heterocyclic ring, optionally containing sulphur, oxygen or an additional nitrogen atom, wherein the ring may be optionally substituted by one or more $C_{1-4}$ alkyl groups; a group of formula —$OSO_2R_{21}$ in which $R_{21}$ is a $C_{1-6}$ alkyl group or an unsubstituted or substituted phenyl group, 4,5dihydrothiazol-2-yl, 4,4-dimethyl-2-oxazolin-2-yl or a group of formula —$NR_{60}R_{61}$ in which $R_{60}$ is hydrogen or a $C_{1-6}$ alkyl group and $R_{61}$ is a $C_{1-6}$ alkanoyl group or unsubstituted or substituted benzoyl; or a group of formula —$(O)_z$-$L_3$G wherein z is 0, $L_3$ is a $C_{1-4}$ alkylene chain which is unsubstituted or substituted by one or more $C_{1-4}$ alkyl groups, and G is a group of formula a), b), c) or d):

a) —$NR_{22}R_{23}$, wherein $R_{22}$ is hydrogen or a $C_{1-6}$ alkyl group; and $R_{23}$ is hydrogen; a $C_{1-6}$ alkyl group; a $C_{1-6}$ alkanoyl group; phenylsulphonyl which is unsubstituted or substituted; benzoyl which is unsubstituted or substituted; a group of formula —$CONR_{24}R_{25}$ wherein $R_{24}$ is hydrogen, a $C_{1-6}$ alkyl group or a $C_{3-6}$ cycloalkyl group, and $R_{25}$ is hydrogen; a $C_{1-6}$ alkyl group; or phenyl which is unsubstituted or substituted;

or $R_{24}$ and $R_{25}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;

b) —$S(O)_mR_{26}$, wherein $R_{26}$ is a $C_{1-6}$ alkyl group or a phenyl group which is unsubstituted or substituted, and m is 0, 1 or 2; or m is 2 and $R_{26}$ is a group of formula —$N(R_{17})R_{18}$ in which $R_{17}$ and $R_{18}$ independently are hydrogen, a $C_{1-6}$ alkyl group, a $C_{3-6}$ cycloalkyl group or phenyl which is unsubstituted or substituted; or $R_{17}$ and $R_{18}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more $C_{1-4}$ alkyl groups;

c) —$CONR_{27}R_{28}$ wherein $R_{27}$ is hydrogen or a $C_{1-6}$ alkyl group; and $R_{28}$ is hydrogen, a $C_{1-6}$ alkyl group, a $C_{3-8}$ cycloalkyl group, a phenyl $C_{1-6}$ alkyl group in which the phenyl ring is unsubstituted or substituted, or phenyl which is unsubstituted or substituted; or $R_{27}$ and $R_{28}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more $C_{1-4}$ alkyl groups;

d) —$OR_2$, wherein $R_{29}$ is a $C_{1-6}$ alkyl group, phenyl which is unsubstituted or substituted, a phenyl $C_{1-6}$ alkyl group in which the phenyl ring is unsubstituted or substituted, a $C_{1-8}$ alkanoyl group, benzoyl which is unsubstituted or substituted, a $C_{1-6}$ alkylsulphonyl group, a phenylsulphonyl group which is unsubstituted or substituted; or $R_{29}$ is a group of formula —$L_4COR_{32}$ in which $L_4$ is a $C_{1-4}$ alkylene chain which is unsubstituted or substituted by one or more $C_{1-4}$ alkyl groups; and $R_{32}$ is hydrogen, a $C_{1-6}$ alkyl group, a $C_{1-6}$ alkoxy group, phenyl which is unsubstituted or substituted, or phenoxy which is unsubstituted or substituted;

or $R_1$ and $R_2$ together with the phenyl ring to which they are attached represent an unsubstituted or substituted naphthyl group;

$R_2$ and $R_3$ independently are hydrogen; a $C_{1-4}$ alkyl group; a $C_{1-4}$ alkoxy group; halo; a perhalo $C_{1-2}$ alkyl group; hydroxy; cyano; a $C_{2-6}$ alkoxycarbonyl group; a group of formula —$S(O)_nR_7$ in which $R_7$ is a $C_{1-6}$ alkyl group or an aryl group and n is 0, 1 or 2; a group of formula —$N(R_{15})SO_2R_{16}$ in which $R_{15}$ is hydrogen or a $C_{1-6}$ alkyl group and $R_{16}$ is hydrogen, a $C_{1-6}$ alkyl group or unsubstituted or substituted phenyl; or a group of formula —$CONR_{11}R_{12}$ in which $R_{11}$ and $R_{12}$ are independently hydrogen, a $C_{1-6}$ alkyl group, a $C_{3-6}$ cycloalkyl group or unsubstituted or substituted phenyl; or $R_{11}$ and $R_{12}$ together with the nitrogen to which they are attached form a saturated 3 to 7-membered heterocyclic ring, optionally containing sulphur, oxygen or an additional nitrogen atom, wherein the ring may be optionally substituted by one or more $C_{1-4}$alkyl groups;

T is O, S, SO, $SO_2$, a carbonyl group or a group of formula (5)

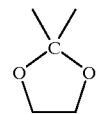

(5)

$L_2$ is a $C_{1-4}$ alkylene chain, a $C_{3-6}$ cycloalkylene group, or a $C_{3-6}$ cycloalkylidene group, each of which is unsubstituted or substituted by one or more unsubstituted or substituted phenyl groups; by one or more $C_{1-4}$ alkyl groups wherein the alkyl groups are substituted by one or more hydroxy groups or a $C_{2-6}$ alkoxycarbonyl group; or by one or more $C_{3-6}$ cycloalkyl groups; or when T is a carbonyl group $L_2$ is a $C_{1-4}$ oxyalkylene chain;

$R_6$ is hydrogen, a $C_{1-4}$ alkyl group which is unsubstituted or substituted by one or more hydroxy groups or by a $C_{2-6}$ alkoxycarbonyl group;

Q is a $C_{1-9}$ alkylene chain which is unsubstituted or substituted by one or more hydroxy groups and/or by one or more $C_{1-4}$ alkyl groups which are unsubstituted or substituted by one or more hydroxy groups; and/or optionally interrupted by oxygen or a carbonyl group;

Y is an imidazole ring of formula (1), (2) or (3)

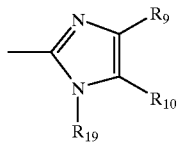  (1)

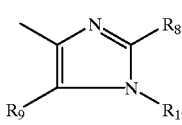  (2)

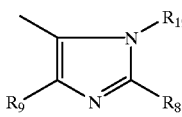  (3)

in which $R_8$ is hydrogen; a $C_{1-6}$ alkyl group; trifluoromethyl; halo; a $C_{1-4}$ alkoxy group; a $C_{1-4}$ hydroxyalkyl group; unsubstituted or substituted phenyl; unsubstituted or substituted benzoyl; an unsubstituted or substituted benzoyl $C_{1-4}$ alkyl group; or a phenyl $C_{1-4}$ alkyl group in which the alkyl chain is optionally substituted by one or more hydroxy groups or one or more $C_{1-4}$ alkyl groups and the phenyl ring is unsubstituted or substituted;

$R_9$ and $R_{10}$ independently are hydrogen; a $C_{1-6}$ alkyl group; halo; trifluoromethyl;

a $C_{1-4}$ alkoxy group; unsubstituted or substituted phenyl; a $C_{1-4}$ hydroxyalkyl group; a $C_{2-6}$ alkoxycarbonyl group; nitro; an amino group of formula $NR_{30}R_{31}$ in which $R_{30}$ and $R_{31}$ are independently hydrogen or a $C_{1-4}$ alkyl group; or $R_{30}$ and $R_{31}$ together with the nitrogen atom to which they are attached represent a saturated 3 to 7-membered heterocyclic ring, optionally containing sulphur, oxygen or an additional nitrogen atom, wherein the ring may be optionally substituted by one or more $C_{1-4}$ alkyl groups, a $C_{1-6}$ alkanoyloxy $C_{1-4}$ alkyl group, a cyano $C_{1-6}$ alkyl group, or a group of formula $L_5$-$NR_{40}R_{41}$ in which $L_5$ is a $C_{1-4}$ alkylene chain which is unsubstituted or substituted by one or more $C_{1-4}$ alkyl groups;

$R_{40}$ is hydrogen or a $C_{1-6}$ alkyl group, and $R_{41}$ is hydrogen; a $C_{1-6}$ alkyl group; a group of formula $SO_2R_{42}$ in which $R_{42}$ is a $C_{1-6}$ alkyl group or unsubstituted or substituted phenyl; a group of formula $COR_{43}$ in which $R_{43}$ is a $C_{1-6}$ alkyl group; unsubstituted or substituted phenyl; unsubstituted or substituted pyridyl; unsubstituted or substituted thienyl; unsubstituted or substituted furyl; or unsubstituted or substituted pyrrolyl; a $C_{1-6}$ alkoxy group, unsubstituted or substituted phenoxy or unsubstituted or substituted arylalkyl; or $R_{41}$ is a group of formula $CONR_{44}R_{45}$ in which $R_{44}$ is hydrogen, a $C_{1-6}$ alkyl group or a $C_{3-6}$ cycloalkyl group, and $R_{45}$ is hydrogen, a $C_{1-6}$ alkyl group or unsubstituted or substituted phenyl; or $R_{44}$ and $R_{45}$ together with the nitrogen atom to which they are attached form a saturated 3–7 membered heterocyclic ring, optionally containing sulphur, oxygen or an additional nitrogen atom, wherein the ring may be unsubstituted or substituted by one or more $C_{1-4}$ alkyl groups; and $R_{19}$ is hydrogen, a $C_{1-8}$ alkyl group, an aryl group or an aryl $C_{1-6}$alkyl group.

6. The compound of claim 5 in which $R_1$ is hydrogen; halo; a $C_{1-6}$ alkyl group which is unsubstituted or substituted by one or more hydroxy groups; unsubstituted or substituted benzyloxy; a $C_{1-4}$ alkoxy group; a $C_{1-4}$ alkylthio group; a $C_{1-4}$ perhaloalkyl group; cyano; a $C_{2-6}$ alkoxycarbonyl group; 4,5-dihydrothiazol-2-yl; or a group of formula —$OSO_2R_{21}$ in which $R_{21}$ is a $C_{1-6}$ alkyl group or an unsubstituted or substituted phenyl group.

7. The compound of claim 5 in which $R_2$ is hydrogen or methyl and $R_3$ is hydrogen, a $C_{1-4}$ alkyl group, a $C_{1-4}$ alkoxy group or halo.

8. The compound of claim 5 in which T is O or S.

9. The compound of claim 5 in which $L_2$ is a $C_{1-4}$ alkylene which is unsubstituted or substituted by one or more $C_{1-4}$ alkyl groups.

10. The compound of claim 5 in which $R_6$ is hydrogen or a $C_{1-4}$ alkyl group which is unsubstituted or substituted by one or more hydroxy groups or a $C_{2-6}$ alkoxycarbonyl group.

11. The compound of claim 5 in which Q is a $C_{2-6}$ alkylene chain which is unsubstituted or substituted by one or more hydroxy groups.

12. The compound of claim 5 in which Y is an imidazole group of formula (1)

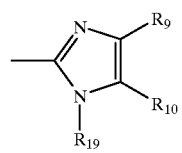  (1)

in which $R_9$ and $R_{10}$ each are hydrogen or a group of formula —$L_5$—$NR_{40}R_{41}$ wherein $L_5$ is a $C_{1-4}$ alkylene chain which is unsubstituted or substituted by one or more alkyl groups; $R_{40}$ is hydrogen or a $C_{1-4}$ alkyl group; and $R_{41}$ is a group of formula $SO_2R_{42}$ in which $R_{42}$ is a $C_{1-6}$ alkyl group or unsubstituted or substituted phenylsubstituted, or $R_{41}$ is a group of formula $COR_{43}$ in which $R_{43}$ is a $C_{1-6}$ alkyl group or unsubstituted or substituted phenyl;

and $R_{19}$ is hydrogen.

13. A compound of formula (IIc)

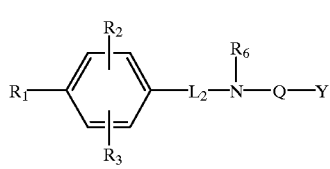  (IIc)

or a pharmaceutically acceptable salt thereof, in which $R_1$ is hydrogen;

halo;

cyano;

a cyano $C_{1-6}$ alkyl group;

a $C_{1-12}$ alkyl group which is unsubstituted or substituted by one or more hydroxy groups;

a $C_{1-6}$ alkoxy group;

phenoxy which is unsubstituted or substituted;

phenyl which is unsubstituted or substituted;

a $C_{2-6}$ alkoxycarbonyl group;

an amino group of formula —$NR_{13}R_{14}$, in which $R_{13}$ and $R_{14}$ are independently hydrogen or a $C_{1-4}$ alkyl group; or $R_{13}$ and $R_{14}$ together with the nitrogen atom to which they are attached form a saturated 3 to 7-membered heterocyclic ring, said ring optionally containing sulphur, oxygen or an additional nitrogen atom, wherein the ring may be substituted by one or more $C_{1-4}$ alkyl groups;

a group of formula —N($R_{15}$)SO$_2$$R_{16}$, in which $R_{15}$ is hydrogen or $C_{1-6}$ alkyl; and $R_{16}$ is hydroxy, a $C_{1-6}$ alkyl group or substituted phenyl;

a halogenated $C_{1-4}$ alkoxy group;

a halogenated $C_{1-4}$ alkyl group;

arylalkoxy which is unsubstituted or substituted;

hydroxy;

a phenyl $C_{1-6}$ alkyl group which is unsubstituted or substituted;

a ($C_{2-6}$ alkoxycarbonyl)vinyl group;

a group of formula —S(O)$_n$$R_7$, in which $R_7$ is a $C_{1-6}$ alkyl group, and n is 0, 1 or 2;

or n is 2 and $R_7$ is a group of formula —N($R_{17}$)$R_{18}$ in which $R_{17}$ and $R_{18}$ independently are hydrogen, a $C_{1-6}$ alkyl group, a $C_{3-6}$ cycloalkyl group or phenyl which is unsubstituted or substituted; or $R_{17}$ and $R_{18}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;

a $C_{2-6}$ alkoxycarbonyl $C_{1-6}$ alkyl group;

a carboxy $C_{1-6}$ alkyl group;

a carbamoyl group of formula —CONR$_{11}$$R_{12}$, in which $R_{11}$ and $R_{12}$ are independently hydrogen, a $C_{1-6}$ alkyl group, a $C_{3-8}$ cycloalkyl group or phenyl which is unsubstituted or substituted; or $R_{11}$ and $R_{12}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;

a carbamoylvinyl group of formula —CH=CH—CON($R_{11}$)$R_{12}$ in which $R_{11}$ and $R_{12}$ are as defined above;

a group of formula —OSO$_2$$R_{21}$, in which $R_{21}$ is a $C_{1-8}$ alkyl group or a phenyl group which is unsubstituted or substituted;

4,5-dihydrothiazol-2-yl, 4,4-dimethyl-2-oxazolin-2-yl;

or a group of formula —NR$_{60}$$R_{61}$, in which $R_{60}$ is hydrogen or a $C_{1-6}$ alkyl group; and $R_{61}$ is a $C_{1-6}$ alkanoyl group or benzoyl which is unsubstituted or substituted;

or $R_1$ is a group of formula —(O)$_z$-L$_3$G, wherein z is 0 or 1; L$_3$ is a $C_{1-4}$ alkylene chain which is unsubstituted or substituted by one or more $C_{1-4}$ alkyl groups; and G is a group of formula a), b), c), or d):

a) —NR$_{22}$$R_{23}$ wherein $R_{22}$ is hydrogen or a $C_{1-6}$ alkyl group; and $R_{23}$ is hydrogen; a $C_{1-6}$ alkyl group; a $C_{1-6}$ alkanoyl group; phenylsulphonyl which is unsubstituted or substituted; benzoyl which is unsubstituted or substituted; a group of formula —CONR$_{24}$$R_{25}$, wherein $R_{24}$ is hydrogen, a $C_{1-6}$ alkyl group or a $C_{3-6}$ cycloalkyl group, and $R_{25}$ is hydrogen; a $C_{1-6}$ alkyl group; or phenyl which is unsubstituted or substituted;

or $R_{24}$ and $R_{25}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;

b) —S(O)$_m$$R_{26}$ wherein $R_{26}$ is a $C_{1-6}$ alkyl group or a phenyl group which is unsubstituted or substituted, and m is 0, 1 or 2; or m is 2 and $R_{28}$ is a group of formula —N($R_{17}$)$R_{18}$ in which $R_{17}$ and $R_{18}$ independently are hydrogen, a $C_{1-6}$ alkyl group, a $C_{3-6}$ cycloalkyl group or phenyl which is unsubstituted or substituted; or $R_{17}$ and $R_{18}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more $C_1$a alkyl groups;

c) —CONR$_{27}$$R_{28}$ wherein $R_{27}$ is hydrogen or a $C_{1-6}$ alkyl group; and $R_{28}$ is hydrogen, a $C_{1-6}$ alkyl group, a $C_{3-8}$ cycloalkyl group, a phenyl $C_{1-6}$ alkyl group in which the phenyl ring is unsubstituted or substituted, or phenyl which is unsubstituted or substituted; or $R_{27}$ and $R_{28}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more $C_{1-4}$ alkyl groups;

d) —OR$_{29}$ wherein $R_{29}$ is a $C_{1-6}$ alkyl group, phenyl which is unsubstituted or substituted, a phenyl $C_{1-6}$ alkyl group in which the phenyl ring is unsubstituted or substituted, a $C_{1-6}$ alkanoyl group, benzoyl which is unsubstituted or substituted, a $C_{1-6}$ alkylsulphonyl group, a phenylsulphonyl group which is unsubstituted or substituted; or $R_{29}$ is a group of formula —L$_4$COR$_{32}$ in which L$_4$ is a $C_{1-4}$ alkylene chain which is unsubstituted or substituted by one or more $C_{1-4}$ alkyl groups; and $R_{32}$ is hydrogen, a $C_{1-6}$ alkyl group, a $C_{1-6}$ alkoxy group, phenyl which is unsubstituted or substituted, or phenoxy which is unsubstituted or substituted;

$R_2$ and $R_3$ independently are hydrogen;

halo;

a $C_{1-6}$ alkyl group which is unsubstituted or substituted by one or more hydroxy groups;

a $C_{1-6}$ alkoxy group;

an amino group of formula —NR$_{13}$$R_{14}$ in which $R_{13}$ and $R_{14}$ are independently hydrogen or a $C_{1-4}$ alkyl group; or $R_{13}$ and $R_{14}$ together with the nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups;

a halogenated $C_{1-4}$ alkoxy group;

a halogenated $C_{1-4}$ alkyl group;

hydroxy;

a group of formula —S(O)$_n$$R_7$, in which $R_7$ is a $C_{1-6}$ alkyl group and n is 0, 1 or 2; or n is 2 and R7 is a group of formula —N($R_{17}$)$R_{18}$ in which $R_{17}$ and $R_{18}$ independently are hydrogen, a $C_{1-6}$ alkyl group, a $C_{3-6}$ cycloalkyl group or phenyl which is unsubstituted or substituted; or $R_{17}$ and $R_{18}$ together with the nitrogen atom to which they are attached form a saturated 3–7 membered heterocyclic ring, optionally containing sulphur, oxygen or an additional nitrogen atom, wherein the ring may be unsubstituted or substituted by one or more $C_{1-4}$ alkyl groups; a group of formula $-NR_{60}R_{61}$ in which $R_{60}$ is hydrogen or a $C_{1-6}$ alkyl group; and $R_{61}$ is a $C_{1-6}$ alkanoyl group, or unsubstituted or substituted benzoyl;

or $R_1$ and $R_2$ together with the phenyl ring to which they are attached form an unsubstituted or substituted or naphthyl group;

or $R_2$ is attached to a position on the phenyl ring adjacent to the position of attachment of $L_1$ on the phenyl ring and $-L_1$-$T$-$L_2-$ and $R_2$ together with the phenyl ring to which they are attached form an indane ring which is which is unsubstituted or substituted;

$L_2$ is a $C_{1-4}$ alkylene chain, a $C_{3-6}$ cycloalkylene group, or a $C_{3-6}$ cycloalkylidene group, each of which is unsubstituted or substituted by one or more unsubstituted or substituted phenyl groups; by one or more $C_{1-4}$ alkyl groups wherein the alkyl groups are substituted by one or more hydroxy groups or a $C_{2-6}$ alkoxycarbonyl group; or by one or more $C_{3-6}$ cycloalkyl groups;

$R_6$ is hydrogen, a $C_{1-4}$ alkyl group which is unsubstituted or substituted by one or more hydroxy groups or by a $C_{2-6}$ alkoxycarbonyl group;

Q is a $C_{1-9}$ alkylene chain which is unsubstituted or substituted by one or more hydroxy groups and/or by one or more $C_{1-4}$ alkyl groups which are unsubstituted or substituted by one or more hydroxy groups; and/or optionally interrupted by oxygen or a carbonyl group;

Y is an imidazole ring of formula (1), (2) or (3)

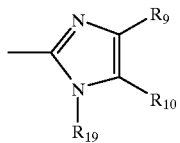
(1)

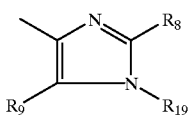
(2)

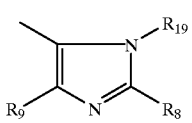
(3)

in which $R_8$ is hydrogen, a $C_{1-6}$ alkyl group, a halogenated $C_{1-6}$ alkyl group, halo, a $C_{1-4}$ alkoxy group, a halogenated $C_{1-4}$ alkoxy group, a $C_{1-4}$ hydroxyalkyl group, unsubstituted or substituted phenyl, unsubstituted or substituted benzoyl, an unsubstituted or sub benzoyl $C_{1-4}$ alkyl group, or a phenyl $C_{1-4}$ alkyl group in which the alkyl chain is unsubstituted or substituted by one or more hydroxy groups or one or more $C_{1-4}$ alkyl groups and the phenyl ring is unsubstituted or substituted;

$R_9$ and $R_{10}$ independently are hydrogen; a $C_{1-6}$ alkyl group; halo; a halogenated $C_{1-6}$ alkyl group; a $C_{1-4}$ alkoxy group; a halogenated $C_{1-4}$ alkoxy group; unsubstituted or substituted phenyl; a $C_{1-4}$ hydroxy-alkyl group; a $C_{2-6}$ alkoxycarbonyl group; nitro; an amino group of formula $NR_{30}R_{31}$ in which $R_{30}$ and $R_{31}$ are independently hydrogen or a $C_{1-4}$ alkyl group; or $R_{30}$ and $R_{31}$ together with the nitrogen atom to which they are attached form a saturated 3–7 membered heterocyclic ring, optionally containing sulphur, oxygen or an additional nitrogen atom, wherein the ring is unsubstituted or substituted by one or more $C_{1-4}$ alkyl groups; a $C_{1-6}$ alkanoyloxy $C_{1-4}$ alkyl group; a cyano $C_{1-6}$ alkyl group; or a group of formula g) or h), g) $-L5-NR_{40}R_{41}$ in which $L_5$ is a $C_{1-4}$ alkylene chain which is unsubstituted or substituted by one or more $C_{1-4}$ alkyl groups; $R_{40}$ is hydrogen or a $C_{1-6}$ alkyl group, and $R_{41}$ is hydrogen; a $C_{1-6}$ alkyl group; a group of formula $SO_2R_{42}$ in which $R_{42}$ is a $C_{1-6}$ alkyl group or unsubstituted or substituted phenyl; a group of formula $COR_{43}$ in which $R_{43}$ is a $C_{1-6}$ alkyl group; unsubstituted or substituted phenyl; unsubstituted or substituted pyridyl; unsubstituted or substituted thienyl; unsubstituted or substituted furyl; or unsubstituted or substituted pyrrolyl; a $C_1$l alkoxy group, unsubstituted or substituted phenoxy or unsubstituted or substituted arylalkyl; or $R_{41}$ is a group of formula $CONR_{44}R_{45}$ in which $R_{44}$ is hydrogen, a $C_{1-6}$ alkyl group or a $C_{3-6}$ cycloalkyl group, and $R_{45}$ is hydrogen, a $C_{1-6}$ alkyl group or unsubstituted or substituted phenyl; or $R_{44}$ and $R_{45}$ together with the nitrogen atom to which they are attached form a pyrrolidine ring, a piperidine ring or a morpholine ring; or h) $-L_7CONR_{90}R_{91}$ in which $L_7$ is a $C_{1-6}$ alkylene chain which is unsubstituted or substituted by one or more $C_{1-4}$ alkyl groups; and $R_{90}$ and $R_{91}$ are independently hydrogen, a $C_{1-6}$ alkyl group or unsubstituted or substituted phenyl; or $R_{90}$ and $R_{91}$ together with the nitrogen atom to which they are attached form a pyrrolidine ring, a piperidine ring or a morpholine ring; and $R_{19}$ is hydrogen, a $C_{1-6}$ alkyl group, an aryl group or an aryl $C_{1-6}$ alkyl group.

14. The compound of formula (IIc), as defined in claim 13, in which $R_1$ is hydrogen; halo; a $C_{1-8}$ alkyl group which is unsubstituted or substituted by one or more hydroxy groups; a $C_{1-4}$ alkoxy group; hydroxy; a carbamoyl group of formula $CONR_{11}R_{12}$ in which $R_{11}$ and $R_{12}$ are independently hydrogen, a $C_{1-6}$ alkyl group, a $C_{3-8}$ cycloalkyl group or unsubstituted or substituted phenyl; or $R_{11}$ and $R_{12}$ together with a nitrogen atom to which they are attached form a saturated 3 to 7-membered heterocyclic ring, optionally containing sulphur, oxygen or an additional nitrogen atom, wherein the ring is unsubstituted or substituted by one or more $C_{1-4}$ alkyl groups; a group of formula $-S(O)_nR_7$ in which n is 2, and $R_7$ is a group of formula $-N(R_{17})R_{18}$ in which $R_{17}$ and $R_{18}$ independently represent hydrogen, a $C_{1-6}$ alkyl group or optionally substituted phenyl; or $R_1$ is a group of formula $-L_3G$ in which $L_3$ is a $C_{1-4}$ alkylene chain which is unsubstituted or substituted by one or more $C_{1-4}$ alkyl groups, and G is a group of formula a, b or c:

a) $-NR_{22}R_{23}$ wherein $R_{22}$ is hydrogen or a $C_{1-6}$ alkyl group; and $R_{23}$ is hydrogen or unsubstituted or substituted phenylsulphonyl;

b) —S(O)$_m$R$_{26}$ in which R$_{26}$ is a C$_{1-6}$ alkyl group; and m is 0, 1 or 2;

c) —CONR$_{27}$R$_{28}$ in which R$_{27}$ is hydrogen or a C$_{1-6}$ alkyl group; and R$_{28}$ is hydrogen, a C$_{1-6}$ alkyl group or unsubstituted or substituted phenyl;

R$_2$ and R$_3$ independently are hydrogen, halo, a C$_{1-6}$ alkyl group, or a C$_{1-6}$alkoxy group;

L$_2$ is a C$_{1-4}$ alkylene chain which is unsubstituted or substituted by one or more C$_{1-4}$ alkyl groups;

Q is a C$_{2-6}$ alkylene chain;

Y is the imidazole group of formula (2), wherein where R$_9$ and R$_{10}$ are hydrogen; and R$_{19}$ is hydrogen or benzyl.

15. The compound of formula (IIc), as defined in claim 13, in which

R$_1$ is hydrogen or halo;

R$_2$ and R$_3$ are each hydrogen;

L$_2$ is —C(R$_4$)(R$_5$)— in which R$_4$ and R$_5$ independently are hydrogen, methyl or ethyl;

R$_6$ is hydrogen or a C$_{1-4}$ alkyl group;

Q is methylene, ethylene or trimethylene; and

Y is imidazol-4(5)-yl.

16. N-(5-chloroindan-1-yl)-3-(imidazol-1-yl) propylamine or a pharmaceutically acceptable salt thereof.

17. A pharmaceutical composition comprising a therapeutically effective amount of a compound of formula I according to claim 1 in combination with a pharmaceutically acceptable diluent or carrier.

18. A pharmaceutical composition comprising a therapeutically effective amount of a compound of formula II according to claim 2 in combination with a pharmaceutically acceptable diluent or carrier.

19. A pharmaceutical composition comprising a therapeutically effective amount of a compound of formula IIa according to claim 5 in combination with a pharmaceutically acceptable diluent or carrier.

20. A pharmaceutical composition comprising a therapeutically effective amount of a compound of formula IIIc according to claim 13 in combination with a pharmaceutically acceptable diluent or carrier.

21. A method of treating an inflammatory condition, an allergic condition or a disease with an immunological association, or a combination thereof, in a mammal, which method comprises administering to a mammal in need of such treatment a therapeutically effective amount of a compound of formula (1)

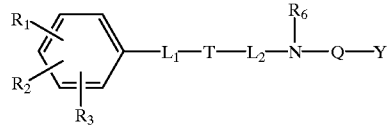

(I)

or a pharmaceutically acceptable salt thereof, in which

R$_1$ is hydrogen;
halo;
cyano;
a cyano C$_{1-6}$ alkyl group;
a C$_{1-12}$ alkyl group which is unsubstituted or substituted by one or more hydroxy groups;
a C$_{1-6}$ alkoxy group;
phenoxy which is unsubstituted or substituted;
phenyl which is unsubstituted or substituted;
a C$_{2-8}$ alkoxycarbonyl group;
an amino group of formula —NR$_{13}$R$_{14}$, in which R$_{13}$ and R$_{14}$ are independently hydrogen or a C$_{1-4}$ alkyl group; or R$_{13}$ and R$_{14}$ together with the nitrogen atom to which they are attached form a saturated 3 to 7-membered heterocyclic ring, said ring optionally containing sulphur, oxygen or an additional nitrogen atom, wherein the ring may be substituted by one or more C$_{1-4}$ alkyl groups;

a group of formula —N(R$_{15}$)SO$_2$R$_{16}$ in which R$_{15}$ is hydrogen or C$_{1-6}$ alkyl; and R$_{16}$ is hydroxy, a C$_{1-6}$ alkyl group or substituted phenyl;

a halogenated C$_{1-4}$ alkoxy group;
a halogenated C$_{1-4}$ alkyl group;
arylalkoxy which is unsubstituted or substituted;
hydroxy;
a phenyl C$_{1-6}$ alkyl group which is unsubstituted or substituted;
a (C$_{2-6}$ alkoxycarbonyl)vinyl group;
a group of formula —S(O)$_n$R$_7$, in which R$_7$ is a C$_{1-6}$ alkyl group, and n is 0, 1 or 2;
or n is 2 and R$_7$ is a group of formula —N(R$_{17}$)R$_{18}$, in which R$_{17}$ and R$_{18}$ independently are hydrogen, a C$_{1-6}$ alkyl group, a C$_{3-6}$ cycloalkyl group or phenyl which is unsubstituted or substituted; or R$_{17}$ and R$_{18}$ together with the nitrogen atom to which they are attached form a saturated 3 to 7-membered heterocyclic ring, optionally containing sulphur, oxygen or an additional nitrogen atom, wherein the ring is unsubstituted or substituted by one or more C$_{1-4}$ alkyl groups;

a C$_{2-6}$ alkoxycarbonyl C$_{1-6}$ alkyl group;
a carboxy C$_{1-6}$ alkyl group;
a carbamoyl group of formula —CONR$_{11}$R$_{12}$, in which R$_{11}$ and R$_{12}$ are independently hydrogen, a C$_{1-6}$ alkyl group, a C$_{3-8}$ cycloalkyl group or phenyl which is unsubstituted or substituted; or R$_{11}$ and R$_{12}$ together with the nitrogen atom to which they are attached form a saturated 3 to 7-membered heterocyclic ring, optionally containing sulphur, oxygen or an additional nitrogen atom, wherein the ring is unsubstituted or substituted by one or more C$_{1-4}$ alkyl groups;

a carbamoylvinyl group of formula —CH=CH—CON (R$_{11}$)R$_{12}$ in which R$_{11}$ and R$_{12}$ are as defined above;

a group of formula —OSO$_2$R$_{21}$, in which R$_{21}$ is a C$_{1-8}$ alkyl group or a phenyl group which is unsubstituted or substituted;

4,5-dihydrothiazol-2-yl, 4,4dimethyl-2-oxazolin-2-yl;

or a group of formula —NR$_{60}$R$_{61}$ in which R$_{60}$ is hydrogen or a C$_1$, alkyl group; and R$_{61}$ is a C$_{1-6}$ alkanoyl group or benzoyl which is unsubstituted or substituted;

or R$_1$ is a group of formula —(O)$_z$-L$_3$G, wherein z is 0 or 1; L$_3$ is a C$_{1-4}$ alkylene chain which is unsubstituted or substituted by one or more C$_{1-4}$ alkyl groups; and G is a group of formula a), b), c), or d):

a) —NR$_{22}$R$_{23}$ wherein R$_{22}$ is hydrogen or a C$_{1-6}$ alkyl group; and R$_{23}$ is hydrogen; a C$_{1-6}$ alkyl group; a C$_{1-6}$ alkanoyl group; phenylsulphonyl which is unsubstituted or substituted; benzoyl which is unsubstituted or substituted; a group of formula —CONR$_{24}$R$_{25}$, wherein R$_{24}$ is hydrogen, a C$_{1-6}$ alkyl group or a C$_{3-6}$ cycloalkyl group, and R$_{25}$ is hydrogen; a C$_{1-6}$ alkyl group; or phenyl which is unsubstituted or substituted; or R$_{24}$ and R$_{25}$ together with the nitrogen atom to which they are attached form a saturated 3 to 7-membered heterocyclic ring, optionally containing sulphur, oxygen or an additional nitrogen atom, wherein the ring is unsubstituted or substituted by one or more C$_{1-4}$ alkyl groups;

b) —S(O)$_m$R$_{26}$ wherein R$_{26}$ is a C$_{1-6}$ alkyl group or a phenyl group which is unsubstituted or substituted, and m is 0, 1 or 2; or m is 2 and R$_{26}$ is a group of formula —N(R$_{17}$)R$_{18}$ in which R$_{17}$ and R$_{18}$ independently are hydrogen, a C$_{1-6}$ alkyl group, a C$_{3-6}$ cycloalkyl group or phenyl which is unsubstituted or substituted; or R$_{17}$ and R$_{18}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more C$_{1-4}$ alkyl groups;

c) —CONR$_{27}$R$_{28}$ wherein R$_{27}$ is hydrogen or a C$_{1-6}$ alkyl group; and R$_{28}$ is hydrogen, a C$_{1-6}$ alkyl group, a C$_{3-8}$ cycloalkyl group, a phenyl C$_{1-6}$ alkyl group in which the phenyl ring is unsubstituted or substituted, or phenyl which is unsubstituted or substituted; or R$_{27}$ and R$_{28}$ together with the nitrogen atom to which they are attached form a saturated 3 to 7-membered heterocyclic ring, optionally containing sulphur, oxygen or an additional nitrogen atom, wherein the ring may be unsubstituted or substituted by one or more C$_{1-4}$ alkyl groups;

d) —OR$_{29}$ wherein R$_{29}$ is a C$_{1-6}$ alkyl group, phenyl which is unsubstituted or substituted, a phenyl C$_{1-6}$ alkyl group in which the phenyl ring is unsubstituted or substituted, a C$_{1-6}$ alkanoyl group, benzoyl which is unsubstituted or substituted, a C$_{1-6}$ alkylsulphonyl group, a phenylsulphonyl group which is unsubstituted or substituted; or R$_{29}$ is a group of formula —L$_4$COR$_{32}$ in which L$_4$ is a C$_{1-4}$ alkylene chain which is unsubstituted or substituted by one or more C$_{1-4}$ alkyl groups; and R$_{32}$ is hydrogen, a C$_{1-6}$ alkyl group, a C$_{1-6}$ alkoxy group, phenyl which is unsubstituted or substituted, or phenoxy which is unsubstituted or substituted;

R$_2$ and R$_3$ independently are
hydrogen;
halo;
a C$_{1-6}$ alkyl group which is unsubstituted or substituted by one or more hydroxy groups;
a C$_{1-6}$ alkoxy group;
an amino group of formula —NR$_{13}$R$_{14}$ in which R$_{13}$ and R$_{14}$ are independently hydrogen or a C$_{1-4}$ alkyl group; or R$_{13}$ and R$_{14}$ together with the nitrogen atom to which they are attached form a saturated 3 to 7-membered heterocyclic ring, optionally containing sulphur, oxygen or an additional nitrogen atom, wherein the ring is unsubstituted or substituted by one or more C$_{1-4}$ alkyl groups;
a halogenated C$_{1-4}$ alkoxy group;
a halogenated C$_{1-4}$ alkyl group;
hydroxy;
a group of formula —S(O)$_n$R$_7$ in which R$_7$ is a C$_{1-6}$ alkyl group and n is 0, 1 or 2; or n is 2 and R$_7$ is a group of formula —N(R$_{17}$)R$_{18}$ in which R$_{17}$ and R$_{18}$ independently are hydrogen, a C$_{1-6}$ alkyl group, a C$_{3-8}$ cycloalkyl group or phenyl which is unsubstituted or substituted; or R$_{17}$ and R$_{18}$ together with the nitrogen atom to which they are attached form a saturated 3–7 membered heterocyclic ring, optionally containing sulphur, oxygen or an additional nitrogen atom, wherein the ring may be unsubstituted or substituted by one or more C$_{1-4}$ alkyl groups;

a group of formula —NR$_{60}$R$_{61}$ in which R$_{60}$ is hydrogen or a C$_{1-6}$ alkyl group; and R$_{61}$ is a C$_{1-6}$ alkanoyl group, or unsubstituted or substituted benzoyl;

or R$_1$ and R$_2$ together with the phenyl ring to which they are attached form an unsubstituted or substituted or naphthyl group;

or R$_2$ is attached to a position on the phenyl ring adjacent to the position of attachment of L$_1$ on the phenyl ring and —L$_1$-T-L$_2$— and R$_2$ together with the phenyl ring to which they are attached form an indane ring which is which is unsubstituted or substituted;

L$_1$ is a bond; or
a C$_{1-4}$ alkylene chain, a C$_{3-6}$ cycloalkylene group, or a C$_{3-6}$ cycloalkylidene group, each of which is unsubstituted or substituted by a) one or more unsubstituted or substituted or phenyl groups, b) one or more C$_{1-4}$ alkyl groups wherein the alkyl groups are unsubstituted or substituted by one or more hydroxy groups or a C$_{2-6}$ alkoxycarbonyl group, or c) by one or more C$_{3-6}$ cycloalkyl groups;

T is a bond or O, S, SO, SO$_2$, a carbonyl group, or a group of formula (5)

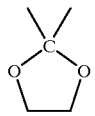

(5)

L$_2$ is a C$_{1-4}$ alkylene chain, a C$_{3-6}$ cycloalkylene group, or a C$_{3-6}$ cycloalkylidene group, each of which is unsubstituted or substituted by one or more unsubstituted or substituted phenyl groups; by one or more C$_{1-4}$ alkyl groups wherein the alkyl groups are substituted by one or more hydroxy groups or a C$_{2-6}$ alkoxycarbonyl group; or by one or more C$_{3-6}$ cycloalkyl groups;
and when T is a carbonyl group L$_2$ additionally is a C$_{1-4}$ oxyalkylene chain, a C$_{3-6}$ oxycycloalkylene group, or a C$_{3-6}$ oxycycloalkylidene group, each of which is unsubstituted or substituted by one or more unsubstituted or substituted phenyl groups; by one or more C$_{1-4}$ alkyl groups wherein the alkyl groups are unsubstituted or substituted by one or more hydroxy groups or a C$_{2-6}$ alkoxycarbonyl group; or by one or more C$_{3-6}$ cycloalkyl groups;

R$^6$ is hydrogen, a C$_{1-4}$ alkyl group which is unsubstituted or substituted by one or more hydroxy groups or by a C$_{2-6}$alkoxycarbonyl group;

Q is a C$_{1-9}$ alkylene chain which is unsubstituted or substituted by one or more hydroxy groups and/or by one or more C$_{1-4}$ alkyl groups which are unsubstituted or substituted by one or more hydroxy groups; and/or optionally interrupted by oxygen or a carbonyl group;

Y is an imidazole ring of formula (1), (2) or (3)

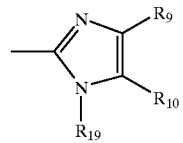

(1)

-continued

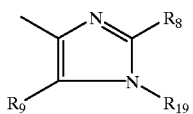

(2)

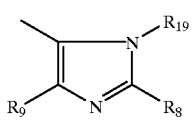

(3)

in which $R_8$ is hydrogen, a $C_{1-6}$ alkyl group, a halogenated $C_{1-6}$ alkyl group, halo, a $C_{1-4}$ alkoxy group, a halogenated $C_{1-4}$ alkoxy group, a $C_{1-4}$ hydroxyalkyl group, unsubstituted or substituted phenyl, unsubstituted or substituted benzoyl, an unsubstituted or sub benzoyl $C_{1-4}$ alkyl group, or a phenyl $C_{1-4}$ alkyl group in which the alkyl chain is unsubstituted or substituted by one or more hydroxy groups or one or more $C_{1-4}$ alkyl groups and the phenyl ring is unsubstituted or substituted;

$R_9$ and $R_{10}$ independently are hydrogen; a $C_{1-6}$ alkyl group; halo; a halogenated $C_{1-6}$ alkyl group; a $C_{1-4}$ alkoxy group; a halogenated $C_{1-4}$ alkoxy group; unsubstituted or substituted phenyl; a $C_{1-4}$ hydroxyalkyl group; a $C_{2-8}$ alkoxycarbonyl group; nitro; an amino group of formula $NR_{30}R_{31}$ in which $R_{30}$ and $R_{31}$ are independently hydrogen or a $C_{1-4}$ alkyl group; or $R_{30}$ and $R_{31}$ together with the nitrogen atom to which they are attached form a saturated 3-7 membered heterocyclic ring, optionally containing sulphur, oxygen or an additional nitrogen atom, wherein the ring is unsubstituted or substituted by one or more $C_{1-4}$ alkyl groups; a $C_{1-6}$ alkanoyloxy $C_{1-4}$ alkyl group; a cyano $C_{1-6}$ alkyl group; or a group of formula g) or h), g) —$L_5$—$NR_{40}R_{41}$ in which $L_5$ is a $C_{1-4}$ alkylene chain which is unsubstituted or substituted by one or more $C_{1-4}$ alkyl groups;

$R_{40}$ is hydrogen or a $C_{1-6}$ alkyl group, and $R_{41}$ is hydrogen; a $C_{1-6}$ alkyl group; a group of formula $SO_2R_{42}$ in which $R_{42}$ is a $C_{1-6}$ alkyl group or unsubstituted or substituted phenyl; a group of formula $COR_{43}$ in which $R_{43}$ is a $C_{1-6}$ alkyl group; unsubstituted or substituted phenyl; unsubstituted or substituted pyridyl; unsubstituted or substituted thienyl; unsubstituted or substituted furyl; or unsubstituted or substituted pyrrolyl; a $C_{1-6}$ alkoxy group, unsubstituted or substituted phenoxy or unsubstituted or substituted arylalkyl; or $R_{41}$ is a group of formula $CONR_{44}R_4$ in which $R_{44}$ is hydrogen, a $C_{1-6}$ alkyl group or a $C_{3-8}$ cycloalkyl group, and $R_{45}$ is hydrogen, a $C_{1-6}$ alkyl group or unsubstituted or substituted phenyl; or $R_{44}$ and $R_{45}$ together with the nitrogen atom to which they are attached form a saturated 3–7 membered heterocyclic ring, optionally containing sulphur, oxygen or an additional nitrogen atom, wherein the ring may be unsubstituted or substituted by one or more $C_{1-4}$ alkyl groups; or h) —$L_7CONR_{90}R_{91}$ in which $L_7$ is a $C_{1-6}$ alkylene chain which is unsubstituted or substituted by one or more $C_{1-4}$ alkyl groups; and $R_{90}$ and $R_{91}$ are independently hydrogen, a $C_{1-6}$ alkyl group or unsubstituted or substituted phenyl; or $R_{90}$ and $R_{91}$ together with the nitrogen atom to which they are attached form a saturated 3–7 membered heterocyclic ring, optionally containing sulphur, oxygen or an additional nitrogen atom, wherein the ring is unsubstituted or substituted by one or more $C_{1-4}$ alkyl groups; and $R_{19}$ is hydrogen, a $C_{1-6}$ alkyl group, an aryl group or an aryl $C_{1-6}$ alkyl group.

* * * * *

UNITED STATES PATENT AND TRADEMARK OFFICE
CERTIFICATE OF CORRECTION

PATENT NO.   : 6,215,001 B1
DATED        : April 10, 2001
INVENTOR(S)  : Calderwood et al.

It is certified that error appears in the above-identified patent and that said Letters Patent is hereby corrected as shown below:

Abstract,
Line 6, after the formula, "-CONR$_{13}$R$_{12}$" should be -- -CONR$_{11}$R$_{12}$ --.

Column 99-101, Claim 1,
Line 44, delete "which is".
Line 67, "-L$_5$NR$_{40}$R$_4$" should be -- -L$_5$NR$_{40}$R$_{41}$ --.
Line 60, "R" should be -- R$_6$ --.

Column 103-106, Claim 2,
Line 11, "R22" should be -- R$_{22}$ --.
Line 36, "C$_1$4" should be -- C$_{1-4}$ --.
Line 13, "-(O)$_n$R$_7$" should be -- -S(O)$_n$R$_7$ --.
Line 4, "CONR$_{44}$R$_4$" should be -- CONR$_{44}$R$_{45}$ --.
Line 24, "allyl" should be -- alkyl --.

Column 106-107, Claim 3,
Line 39, "-(O)$_n$R$_7$" should be -- -S(O)$_n$R7 --.
Line 61, "-(O)$_z$-L3G" should be -- -(O)$_z$-L$_3$G --.
Line 62, "L3 is a C, 4alkylene" should be -- L$_3$ is a C$_{1-4}$alkylene --.
Line 7, "R$_{28}$" should be -- R$_{26}$ --.

Column 112, Claim 5,
Line 4, "C$_{1-8}$" should be -- C$_{1-6}$ --.

Column 115-118, Claim 13,
Line 43, "C$_{1-8}$" should be -- C$_{1-6}$ --.
Line 7, "R$_{28}$" should be -- R$_{26}$ --.
Line 16, "C$_1$a" should be -- C$_{1-4}$ --.
Line 62, "R7" should be -- R$_7$ --.
Line 63, "R,$_7$ and R,$_8$" should be -- R$_{17}$ and R$_{18}$ --.
Line 15, delete "which is".
Line 12, "-L5-" should be -- -L$_5$ --.
Line 23, "C$_1$1" should be -- C$_{1-4}$ --.

Column 119, Claim 21,
Line 65, "C$_{2-8}$" should be -- C$_{2-6}$ --.

UNITED STATES PATENT AND TRADEMARK OFFICE
CERTIFICATE OF CORRECTION

PATENT NO. : 6,215,001
DATED : April 10, 2001
INVENTOR(S) : Calderwood et al.

It is certified that error appears in the above-identified patent and that said Letters Patent is hereby corrected as shown below:

<u>Column 120-124, Claim 21,</u>
Line 41 "$C_{1-8}$" should be -- $C_{1-6}$ --.
Line 46, "$C_1$," should be -- $C_{1-6}$ --.
Line 61, "$C_{3-8}$" should be -- $C_{3-6}$ --.
Line 13, delete "which is".
Line 29, "$C_{2-8}$" should be -- $C_{2-6}$ --.
Line 15, "$CONR_{44}R_4$" should be -- $CONR_{44}R_{45}$ --.
Line 16, "$C_{3-8}$" should be -- $C_{3-6}$ --.

Signed and Sealed this

Twenty-seventh Day of November, 2001

Attest:

*Nicholas P. Godici*

NICHOLAS P. GODICI
*Attesting Officer*     *Acting Director of the United States Patent and Trademark Office*